United States Patent [19]
Chen et al.

[11] Patent Number: 5,663,171
[45] Date of Patent: Sep. 2, 1997

[54] ACYCLIC COMPOUNDS PROMOTE RELEASE OF GROWTH HORMONE

[75] Inventors: Meng Hsin Chen, Westfield; Gregori J. Morriello, Belleville; Ravi Nargund, East Brunswick; Arthur A. Patchett, Westfield; Lihu Yang, Edison, all of N.J.

[73] Assignee: Merck & Co., Inc., Rahway, N.J.

[21] Appl. No.: 398,247

[22] Filed: Mar. 3, 1995

Related U.S. Application Data

[63] Continuation-in-part of PCT/US94/13596, Nov. 23, 1994 which is a continuation-in-part of Ser. No. 157,774, Nov. 24, 1993, abandoned.

[51] Int. Cl.$^6$ ............ C07D 413/14; C07D 413/12; C07D 209/20; C07D 403/12; A61K 31/405; A61K 31/535; A61K 21/455

[52] U.S. Cl. ............ 514/19; 514/419; 514/323; 514/233.5; 544/124; 544/143; 546/175; 546/268.4; 546/276.4; 546/277.4; 548/495; 548/455; 548/159; 548/253; 548/305.1

[58] Field of Search ............ 548/495, 455; 514/419, 323, 233.5; 546/273; 544/124, 143

[56] References Cited

U.S. PATENT DOCUMENTS

| | | | |
|---|---|---|---|
| 4,411,890 | 10/1983 | Momany | 424/197 |
| 4,522,824 | 6/1985 | Wagnon et al. | 514/414 |
| 4,658,038 | 4/1987 | Tamir et al. | 548/495 |
| 5,324,737 | 6/1994 | D'Ambra et al. | 514/323 |

FOREIGN PATENT DOCUMENTS

| | | |
|---|---|---|
| 0 144 230 | 6/1985 | European Pat. Off. . |
| WO94/11012 | 5/1994 | WIPO . |
| WO94/13696 | 6/1994 | WIPO . |
| WO94/19367 | 9/1994 | WIPO . |
| WO95/17423 | 6/1995 | WIPO . |
| WO95/17422 | 6/1995 | WIPO . |
| WO96/15148 | 5/1996 | WIPO . |

OTHER PUBLICATIONS

McDowell, et al., *Proc. Natl. Acad. Sci. USA*, 92, 11165–11169 (Nov. 1995) "Growth hormone secretagogues: Characterization, efficacy, and minimal bioactive conformation".

Slide of Presentation on "Genentech Growth Hormone Secretagogues" by Todd Somers, at Serano Symposium on Growth Secretagogues, in St. Petersburg, Florida, Dec. 5–8, 1994.

Smith, et al., *Science*, "A Nonpeptidyl Growth Hormone Secretagogue", vol. 260, pp. 1640–1643, Jun. 11, 1993.

Primary Examiner—David B. Springer
Attorney, Agent, or Firm—J. Eric Thies; David L. Rose

[57] ABSTRACT

The present invention is directed to certain compounds of the general structural formula:

$$R_1 \underset{*}{\overset{R_{1a}}{\underset{|}{\rule{0pt}{10pt}}}} \overset{R_{2a}}{\underset{|}{\rule{0pt}{10pt}}} \overset{O}{\underset{\|}{\rule{0pt}{10pt}}} \text{N-C-A-N} \overset{R_4}{\underset{R_5}{\rule{0pt}{10pt}}}$$

wherein $R_1$, $R_{1a}$, $R_{2a}$, $R_3$, $R_{3a}$, $R_4$, $R_5$, $R_6$, A, W, and n are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such compounds as the active ingredient thereof are also disclosed.

9 Claims, No Drawings

ACYCLIC COMPOUNDS PROMOTE RELEASE OF GROWTH HORMONE

CROSS REFERENCE TO RELATED APPLICATIONS

This application is a continuation-in-part of PCT Application No. U.S. Pat. No. 9,413,596, filed Nov. 23, 1994, which is a continuation-in-part of application Ser. No. 08/157,774, filed Nov. 24, 1993, abandoned.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones still have low oral bioavailability. The instant compounds are low molecular weight peptide analogs for promoting the release of growth hormone which have good stability in a variety of physiological environments and which may be administered parenterally, nasally or by the oral route.

SUMMARY OF THE INVENTION

The present invention is directed to certain compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food or wool production where the stimulation of growth hormone will result in a larger, more productive animal. Thus, it is an object of the instant invention to describe such compounds. It is a further object of this invention to describe procedures for the preparation of such compounds. A still further object is to describe the use of such compounds to increase the secretion of growth hormone in humans and animals. A still further object of this invention is to describe compositions containing the compounds and their analogs for the use of treating humans and animals so as to increase the level of growth hormone secretions. Further objects will become apparent from a reading of the following description.

DESCRIPTION OF THE INVENTION

The compounds of the present invention are best described in the following structural Formula I:

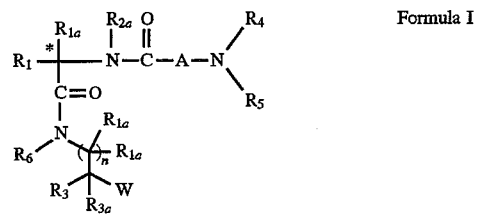

Formula I wherein:

$R_1$ is selected from the group consisting of:
$C_1$–$C_{10}$ alkyl, aryl, aryl($C_1$–$C_6$ alkyl)—, $C_3$–$C_7$ cycloalkyl ($C_1$–$C_6$ alkyl)—, ($C_1$–$C_5$ alkyl)—K—($C_1$–$C_5$ alkyl)—, aryl($C_0$–$C_5$ alkyl)—K—($C_1$–$C_5$ alkyl)—, and ($C_3$–$C_7$ cycloalkyl)($C_0$–$C_5$ alkyl)—K—($C_1$–$C_5$ alkyl)—, where K is —O—, —S(O)$_m$—, —N($R_2$)C(O)—, —C(O)N($R_2$)—, —OC(O)—, —C(O)O—, —CR$_2$=CR$_2$—, or —C≡C—, where aryl is selected from: phenyl, naphthyl, indolyl, azaindolyl, pyridyl, benzothienyl, benzofuranyl, thiazolyl, quinolinyl, and benzimidazolyl, and where $R_2$ and alkyl may be further substituted by 1 to 9 halogen, —S(O)$_m$R$_{2a}$, 1 to 3 of —OR$_{2a}$ or —C(O)OR$_{2a}$, and aryl may be further substituted by 1 to 3 of $C_1$–$C_6$ alkyl, 1 to 3 of halogen, 1 to 2 of —OR$_2$, methylenedioxy, —N($R_2$)($R_2$), —S(O)$_m$R$_2$, 1 to 2 of —CF$_3$, —OCF$_3$, —C(O)H, nitro, —N($R_2$)C(O)($R_2$), —C(O)OR$_2$, —C(O)N($R_2$)($R_2$), —1H-tetrazol-5-yl, —SO$_2$N($R_2$)($R_2$), —N($R_2$)SO$_2$ phenyl, or —N($R_2$)SO$_2$R$_2$;

$R_{1a}$ is independently hydrogen, or $C_1$–$C_6$ alkyl;

$R_2$ is selected from the group consisting of:
hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur, SO$_2$ or NR$_{2a}$;

$R_{2a}$ is hydrogen, or $C_1$–$C_6$ alkyl optionally substituted by hydroxyl;

$R_3$ is independently selected from the group consisting of:
hydrogen, —$C_1$–$C_{10}$ alkyl, —(CH$_2$)$_r$phenyl, —(CH$_2$)$_r$naphthyl, —(CH$_2$)$_r$indanyl, —(CH$_2$)$_r$dibenzocycloheptanyl, —(CH$_2$)$_r$C(O)OR$_8$, —(CH$_2$)$_r$C(O)N(R$_2$)(R$_8$), ($C_1$–$C_6$ alkyl)—K—($C_1$–$C_4$ alkyl)—, aryl($C_0$–$C_5$ alkyl)—K—($C_1$–$C_4$ alkyl)—, —(CH$_2$)$_r$—$C_3$–$C_7$ cycloalkyl, and —(CH$_2$)$_r$heteroaryl, where K is O or S(O)$_m$, and where heteroaryl is selected from: pyridyl, indolyl, imidazolyl, quinolinyl, benzothiopheneyl, benzofuranyl, dihydroindolyl, thiazolyl, benzimidazolyl, and azaindolyl, and where the phenyl, naphthyl, indanyl, dibenzocycloheptanyl, and heteroaryl may be substituted by:

$C_1$–$C_6$ alkyl, 1 to 2 of halogen, 1 to 2 of —OR$_9$, —NHSO$_2$CF$_3$, —C(O)H, —(CH$_2$)$_r$N(R$_2$)(R$_9$), —(CH$_2$)

,C(O)OR$_9$, —(CH$_2$)$_v$N(R$_2$)C(O)R$_9$, —(CH$_2$)$_v$C(O)N(R$_2$)(R$_9$), —(CH$_2$)$_v$N(R$_6$)C(O)N(R$_2$)(R$_9$), or —(CH$_2$)$_r$(R$_9$);

R$_{3a}$ is hydrogen or C$_1$–C$_6$ alkyl;

R$_4$ and R$_5$ are independently selected from:

hydrogen, C$_1$–C$_6$ alkyl, and substituted C$_1$–C$_6$ alkyl where the substituents are selected from: 1 to 5 halogen, 1 to 3 of hydroxy, 1 to 3 of C$_1$–C$_{10}$ alkanoyloxy, 1 to 3 of C$_1$–C$_6$ alkoxy, phenyl, phenoxy, 2-furyl, C$_1$–C$_6$ alkoxycarbonyl, and S(O)$_m$(C$_1$–C$_6$ alkyl); or R$_4$ and R$_5$ can be taken together to form —(CH$_2$)$_d$L$_a$(CH$_2$)$_e$— where L$_a$ is —C(R$_2$)$_2$—, —O—, —S(O)$_m$— or —N(R$_{2a}$)—, and d and e are independently 1 to 3;

R$_6$ is hydrogen or C$_1$–C$_4$ alkyl;

R$_7$ and R$_{7a}$ are independently hydrogen, C$_1$–C$_6$ alkyl, trifluoromethyl, phenyl, substituted C$_1$–C$_6$ alkyl where the substituents are selected from:

imidazolyl, phenyl, indolyl, p-hydroxyphenyl, naphthyl, halophenyl, quinolinyl, dihalophenyl, C$_1$–C$_2$ alkoxyphenyl, di (C$_1$–C$_2$ alkoxy)phenyl, C$_1$–C$_2$ alkylphenyl, di (C$_1$–C$_2$ alkyl)phenyl, —OR$_2$, —S(O)$_m$R$_2$, —C(O)O(C$_1$–C$_6$ alkyl), C$_3$–C$_7$ cycloalkyl, —N(R$_2$)(R$_2$), and —C(O)N(R$_2$)(R$_2$); or R$_7$ and R$_{7a}$ can independently be joined to one or both of R$_4$ and R$_5$ groups to form an alkylene bridge between the terminal nitrogen and the alkyl portion of the R$_7$ or R$_{7a}$ groups, wherein the bridge contains 1 to 5 carbons atoms; or R$_7$ and R$_{7a}$ can be joined to one another to form a C$_3$–C$_7$ cycloalkyl;

R$_8$ is selected from the group consisting of:

hydrogen, C$_1$–C$_6$ alkyl, aryl, and aryl—C$_1$–C$_2$ alkyl, where the alkyl groups may be substituted by a substituent selected from the group consisting of: —OR$_2$, —C(O)OR$_2$, —C(O)O—benzyl, —CON(R$_2$)(R$_2$), —N(R$_2$)C(O)N(R$_2$)(R$_2$), and 1H-tetrazol-5-yl, and where aryl is selected from the group consisting of: phenyl, naphthyl, indolyl, quinolinyl, benzothiopheneyl, benzofuranyl, azaindolyl, benzimidazolyl, pyridyl, and thiazolyl, and where the aryl may be substituted by: 1 to 2 of —OR$_2$, 1 to 2 of halogen, 1 to 2 of C$_1$–C$_3$ alkyl, —C(O)OR$_2$, —C(O)N(R$_2$)(R$_2$), or —1H-tetrazol-5-yl;

R$_9$ is hydrogen, C$_1$–C$_6$ alkyl, or (CH$_2$)$_v$aryl, wherein the alkyl and (CH$_2$)$_v$ groups may be optionally substituted by 1 to 2 of —O(R$_2$), —S(O)$_m$R$_2$, —N(R$_2$)(R$_2$), 1H-tetrazol-5-yl, —C(O)OR$_2$, —C(O)N(R$_2$)(R$_2$), —SO$_2$N(R$_2$)(R$_2$), or —N(R$_2$)C(O)N(R$_2$)(R$_2$), and where aryl is selected from:

phenyl, pyridyl, 1H-tetrazol-5-yl, triazolyl, imidazolyl, thiazolyl, oxadiazolyl, pyrazolyl, thiadiazolyl, imidazolone-1-yl, and benzimidazol-2-yl, triazolinone-yl, and where the aryl is optionally substituted with C$_1$–C$_6$ alkyl, C$_3$–C$_6$ cycloalkyl, amino, hydroxyl, or —C(O)O(R$_2$);

A is:

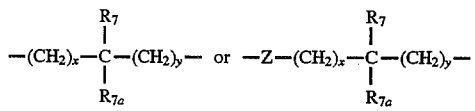

where x and y are independently 0, 1, 2 or 3;

Z is —NR$_2$ or —O—;

W is selected from the group consisting of:

hydrogen, —C(O)OR$_8$, —C(O)N(R$_2$)(R$_2$), —C(O)NH— SO$_2$(R$_2$), —C(O)N(R$_2$)(R$_8$), —CH$_2$N(R$_2$)C(O)N(R$_2$) (R$_8$), —CH$_2$N(R$_2$)C(O)R$_8$, —CH$_2$N(R$_2$)C(O)(R$_8$), —(CH$_2$)$_r$OR$_2$, —CH(OH)R$_2$, —CH$_2$SO$_2$R$_2$, —CH$_2$SO$_2$N(R$_2$)(R$_2$), 1H-tetrazol-5-yl, 5-amino-1,2, 4-oxadiazol-3-yl, 5-methyl-1,2,4-oxadiazol-3-yl, 3-amino-1,2,4-oxadiazol-5-yl, and 3-methyl-1,2,4-oxadiazol-5-yl;

m is 0, 1, or 2;

n is 0 or 1;

r is 0, 1, 2, or 3;

v is 0, 1, or 2;

and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl (Me), ethyl (Et), propyl (Pr), isopropyl (i-Pr), butyl (Bu), sec-butyl (s-Bu), tertiary butyl (t-Bu), pentyl, isopentyl, hexyl, isohexyl, allyl, propinyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propinyloxy, isobutenyloxy, hexenyloxy and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl; which may be optionally substituted by 1 to 3 of C$_1$–C$_6$ alkyl, 1 to 3 of halogen, 1 to 2 of —OR$_2$, —N(R$_2$)(R$_2$), methylenedioxy, —S(O)$_m$R$_2$, 1 to 2 of —CF$_3$, —OCF$_3$, nitro, —N(R$_2$)C(O)(R$_2$), —C(O) OR$_2$, —C(O)N(R$_2$)(R$_2$), —1H-tetrazol-5-yl, —SO$_2$N(R$_2$) (R$_2$), —N(R$_2$)SO$_2$phenyl, or —N(R$_2$)SO$_2$R$_2$, wherein R$_2$ is as defined herein.

Certain of the above defined terms may occur more than once in the above formula or definitions and upon such occurrence, each term shall be defined independently of the other.

Preferred compounds of the instant invention include those of Formula Ia:

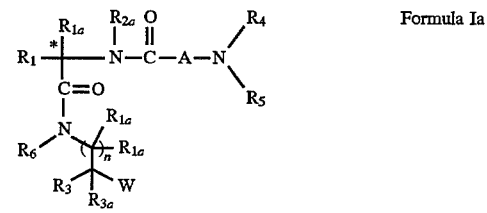

Formula Ia wherein:

R$_1$ is selected from the group consisting of:

C$_1$–C$_{10}$ alkyl, aryl, aryl(C$_1$–C$_4$ alkyl)—, C$_3$–C$_6$ cycloalkyl (C$_1$–C$_4$ alkyl)—, (C$_1$–C$_4$ alkyl)—K—(C$_1$–C$_2$ alkyl)—, aryl(C$_0$–C$_2$ alkyl)—K—(C$_1$–C$_2$ alkyl)—, and (C$_3$–C$_7$ cycloalkyl)(C$_0$–C$_2$ alkyl)—K—(C$_1$–C$_2$ alkyl)—, where K is —O—, —S(O)$_m$—, —OC(O)—, or —C(O)O—, where the alkyl groups may be further substituted by 1 to 7 halogen, —S(O)$_m$R$_{2a}$, 1 to 3 of —OR$_{2a}$ or —C(O)OR$_{2a}$, and where aryl is selected from: phenyl, naphthyl, indolyl, pyridyl, benzimidazolyl, azaindolyl, benzothienyl, and benzofuranyl, and where the aryl may be further substituted by 1 to 2 of $C_1$–$C_4$ alkyl, 1 to 2 of halogen, —C(O)H, 1 to 2 of —$OR_2$, —$S(O)_mR_2$, or —$C(O)OR_2$;

$R_{1a}$ is independently hydrogen or $C_1$–$C_3$ alkyl;

$R_2$ is selected from the group consisting of:
hydrogen, $C_1$–$C_6$ alkyl, and $C_3$–$C_7$ cycloalkyl, and where two $C_1$–$C_6$ alkyl groups are present on one atom they may be optionally joined to form a $C_4$–$C_7$ cyclic ring optionally including oxygen, sulfur or $NR_{2a}$;

$R_{2a}$ is hydrogen or $C_1$–$C_4$ alkyl;

$R_3$ is independently selected from the group consisting of:
hydrogen, —$C_1$–$C_8$ alkyl, —$(CH_2)_r$phenyl, —$(CH_2)_r$naphthyl, —$(CH_2)_r$indanyl, —$(CH_2)_r$dibenzocycloheptanyl, and —$(CH_2)_r$heteroaryl, where heteroaryl is selected from: pyridyl, indolyl, quinolinyl, benzothiopheneyl, benzofuranyl, thiazolyl, dihydroindolyl, benzimidazolyl, and azaindolyl, and where the phenyl, naphthyl, indanyl, dibenzocycloheptanyl, and heteroaryl may be substituted by:

$C_1$–$C_4$ alkyl, 1 to 2 of halogen, 1 to 2 of —$OR_2$, —$NHSO_2CF_3$, —$(CH_2)_rC(O)OR_2$, —$(CH_2)_rC(O)N(R_2)(R_2)$, —$(CH_2)_rN(R_6)C(O)N(R_2)(R_2)$, or —$(CH_2)_r(R_9)$;

$R_{3a}$ is hydrogen or $C_1$–$C_6$ alkyl;

$R_4$ and $R_5$ are independently selected from:
hydrogen, $C_1$–$C_6$ alkyl, and substituted $C_1$–$C_6$ alkyl where the substituents are selected from: 1 to 5 of halogen, 1 to 3 of hydroxyl, S(O)m ($C_1$–$C_6$ alkyl), and phenyl;

$R_6$ is hydrogen or $C_1$–$C_4$ alkyl;

$R_7$ and $R_{7a}$ are independently hydrogen, $C_1$–$C_6$ alkyl, trifluoromethyl, phenyl, substituted $C_1$–$C_6$ alkyl where the substituents are selected from:
imidazolyl, phenyl, indolyl, p-hydroxyphenyl, naphthyl, halophenyl, quinolinyl, dihalophenyl, $C_1$–$C_2$ alkoxyphenyl, di ($C_1$–$C_2$ alkoxy)phenyl, —$OR_2$, —$S(O)_mR_2$, —$C(O)O(C_1$–$C_6$ alkyl), $C_3$–$C_7$ cycloalkyl, —$N(R_2)(R_2)$, and —$C(O)N(R_2)(R_2)$; or $R_7$ and $R_{7a}$ can independently be joined to one or both of $R_4$ and $R_5$ groups to form an alkylene bridge between the terminal nitrogen and the alkyl portion of the $R_7$ or $R_{7a}$ groups, wherein the bridge contains 1 to 5 carbons atoms; or $R_7$ and $R_{7a}$ can be joined to one another to form a $C_3$–$C_7$ cycloalkyl;

$R_8$ is selected from the group consisting of:
hydrogen, $C_1$–$C_4$ alkyl, aryl, and aryl-$C_1$–$C_2$ alkyl, where the alkyl groups may be substituted by a substituent selected from the group consisting of: —$OR_2$, —$C(O)OR_2$, —$C(O)O$—benzyl, —$CON(R_2)(R_2)$, —$N(R_2)C(O)N(R_2)(R_2)$, and 1H-tetrazol-5-yl, and where aryl is selected from the group consisting of: phenyl, naphthyl, indolyl, azaindolyl, pyridyl, and thiazolyl, and where the aryl may be substituted by: 1 to 2 of —$OR_2$, 1 to 2 of halogen, or 1 to 2 of $C_1$–$C_3$ alkyl;

$R_9$ is $(CH_2)_v$aryl, where aryl is selected from:
phenyl, pyridyl, 1H-tetrazol-5-yl, or oxadiazolyl, and where the aryl is optionally substituted with $C_1$–$C_6$ alkyl, amino, hydroxyl, or —$C(O)O(R_2)$;

A is:

$$-(CH_2)_x-\underset{R_{7a}}{\underset{|}{\overset{R_7}{\overset{|}{C}}}}-(CH_2)_y- \quad \text{or} \quad -Z-(CH_2)_x-\underset{R_{7a}}{\underset{|}{\overset{R_7}{\overset{|}{C}}}}-(CH_2)_y-$$

where x and y are independently 0, 1, 2 or 3;
Z is —$NR_2$— or —O—;

W is selected from the group consisting of:
hydrogen, —$C(O)OR_8$, —$CH_2OR_2$, —$C(O)N(R_2)(R_2)$, —$C(O)N(R_2)(R_8)$, 1H-tetrazol-5-yl, —$CH_2N(R_2)C(O)R_8$, $CH_2N(R_2)C(O)N(R_2)(R_8)$, —$(CH_2)_rOR_2$, —CH(OH)$R_2$, 3-amino-1,2,4-oxadiazol-5-yl, 3-methyl-1,2,4-oxadiazol-5-yl,5-amino-1,2,4-oxadiazol-3-yl, and 5-methyl-1,2,4-oxadiazol-3-yl;

m is 0, 1, or 2;
n is 0 or 1;
r is 0, 1, 2, or 3;
v is 0, 1, or 2;

and pharmaceutically acceptable salts and individual diastereomers thereof.

More preferred compounds of the instant invention include those of Formula Ib:

$$\underset{R_3}{\underset{|}{R_6}}\underset{\underset{R_{3a}}{|}}{\overset{R_{1a}}{\underset{|}{\overset{*}{\underset{|}{\overset{|}{N}}}}}}\underset{\underset{C=O}{|}}{\overset{R_{2a}}{\underset{|}{N}}}\overset{O}{\overset{||}{C}}-A-N\diagup\overset{R_4}{\diagdown R_5} \quad \text{Formula Ib}$$

wherein:
$R_1$ is selected from the group consisting of:
$C_1$–$C_{10}$ alkyl, aryl ($C_1$–$C_3$ alkyl)—, $C_3$–$C_7$ cycloalkyl ($C_1$–$C_3$ alkyl)—, and aryl ($C_0$–$C_1$ alkyl)—K—($C_1$–$C_2$ alkyl)—, where K is —O— or —$S(O)_m$— and aryl is selected from: phenyl, pyridyl, naphthyl, indolyl, azaindolyl, and benzofuranyl, and where the aryl may be further substituted by 1 to 2 of $C_1$–$C_4$ alkyl, 1 to 2 of halogen, 1 to 2 of —$OR_2$, —$S(O)_m R_2$, or —$C(O)OR_2$;

$R_{1a}$ is independently hydrogen or $C_1$–$C_2$ alkyl;

$R_2$ is selected from the group consisting of:
hydrogen, $C_1$–$C_6$ alkyl, and $C_3$–$C_7$ cycloalkyl, and where two $C_1$–$C_6$ alkyl groups are present on one atom they may be optionally joined to form a $C_5$–$C_7$ cyclic ring optionally including oxygen, sulfur or $NR_{2a}$;

$R_{2a}$ is hydrogen or $C_1$–$C_3$ alkyl;

$R_3$ is independently selected from the group consisting of:
hydrogen, —$C_1$–$C_6$ alkyl, —$(CH_2)_r$phenyl, —$(CH_2)_r$naphthyl, and —$(CH_2)_r$heteroaryl, where heteroaryl is selected from: pyridyl, thiazolyl, indolyl, quinolinyl, benzofuranyl, and azaindolyl, and where the phenyl, naphthyl and heteroaryl may be substituted by:

$C_1$–$C_3$ alkyl, 1 to 2 of halogen, 1 to 2 of —$OR_2$, —$(CH_2)_rC(O)OR_2$, —$(CH_2)_rC(O)N(R_2)(R_2)$, —$(CH_2)_rN(R_6)C(O)N(R_2)(R_2)$, or —$(CH_2)_r(R_9)$;

$R_{3a}$ is hydrogen or $C_1$ alkyl;

$R_4$ and $R_5$ are independently hydrogen, $C_1$–$C_4$ alkyl, or substituted $C_1$–$C_3$ alkyl where the substituents are selected from:
1 to 5 of halogen, 1 to 3 of hydroxyl, S(O)m ($C_1$–$C_6$ alkyl), and phenyl;

$R_6$ is hydrogen or $C_1$–$C_3$ alkyl;

$R_7$ and $R_{7a}$ are independently hydrogen, $C_1$–$C_3$ alkyl, phenyl, substituted $C_1$–$C_6$ alkyl where the substituents are selected from:
imidazolyl, phenyl, indolyl, p-hydroxyphenyl, naphthyl, halophenyl, dihalophenyl, —$OR_2$, —$N(R_2)(R_2)$, and —$S(O)_mR_2$, or $R_7$ and $R_{7a}$ can independently be joined to one of $R_4$ and $R_5$ groups to form an alkylene bridge between the terminal nitrogen and the alkyl portion of the $R_7$ or $R_{7a}$ groups to form a 5 or 6 membered ring; or $R_7$ and $R_{7a}$ can be joined to one another to form a $C_3$ cycloalkyl;

$R_8$ is selected from the group consisting of:

hydrogen, $C_1$–$C_4$ alkyl, and aryl-$C_1$–$C_2$ alkyl, where the alkyl groups may be substituted by a substituent selected from the group consisting of: —$OR_2$, —$C(O)OR_2$, —$C(O)O$—benzyl, —$CON(R_2)(R_2)$, —$N(R_2)C(O)N(R_2)(R_2)$, and 1H-tetrazol-5-yl, and where aryl is selected from the group consisting of: phenyl, naphthyl, indolyl, 7-azaindolyl, pyridyl, and thiazolyl, and where the aryl may be substituted by: 1 to 2 of —$OR_2$, 1 to 2 of halogen, or 1 to 2 of $C_1$–$C_3$ alkyl;

$R_9$ is $(CH_2)_v$aryl, where aryl is selected from:

1H-tetrazol-5-yl, and oxadiazolyl, and where the aryl is optionally substituted with $C_1$–$C_6$ alkyl, amino, or hydroxyl;

A is:

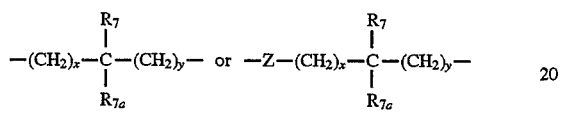

where x and y are independently 0, 1, or 2;

W is selected from the group consisting of:

hydrogen, —$C(O)OR_8$, $CH_2OR_2$, —$C(O)N(R_2)(R_2)$, —$C(O)N(R_2)(R_8)$, 1H-tetrazol-5-yl, $CH_2N(R_2)C(O)R_8$, $CH_2N(R_2)C(O)N(R_2)(R_8)$, 3-amino-1,2,4-oxadiazol-5-yl, and 3-methyl-1,2,4-oxadiazol-5-yl;

Z is —$NR_2$— or —O—;

W is selected from the group consisting of:

hydrogen, —$C(O)OR_8$, —$C_2OR_2$ —$C(O)N(R_2)(R_2)$, —$C(O)N(R_2)(R_8)$, 1H-tetrazol-5-yl, —$CH_2N(R_2)C(O)R_8$, $CH_2N(R_2)C(O)N(R_2)(R_8)$, —$(CH_2)_rOR_2$, —$CH(OH)R_2$, 3-amino-1,2,4-oxadiazol-5-yl, and 3-methyl-1,2,4-oxadiazol-5-yl;

m is 0, 1, or 2;
n is 0 or 1;
r is 0, 1, 2, or 3;
v is 0, 1, or 2;

and pharmaceutically acceptable salts and individual diastereomers thereof.

The most preferred growth hormone releasing compounds of the present invention include the following:

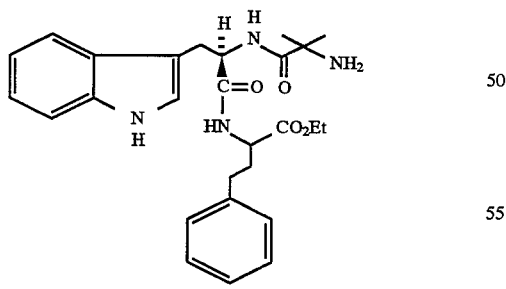

-continued

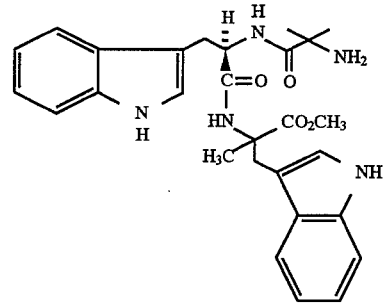

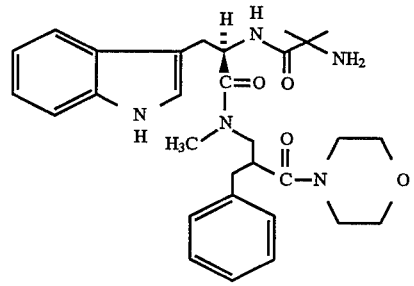

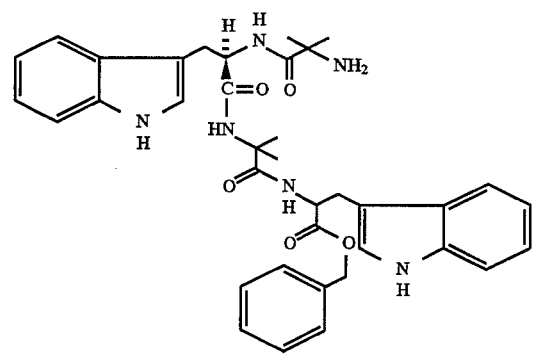

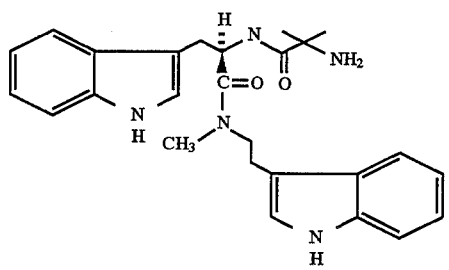

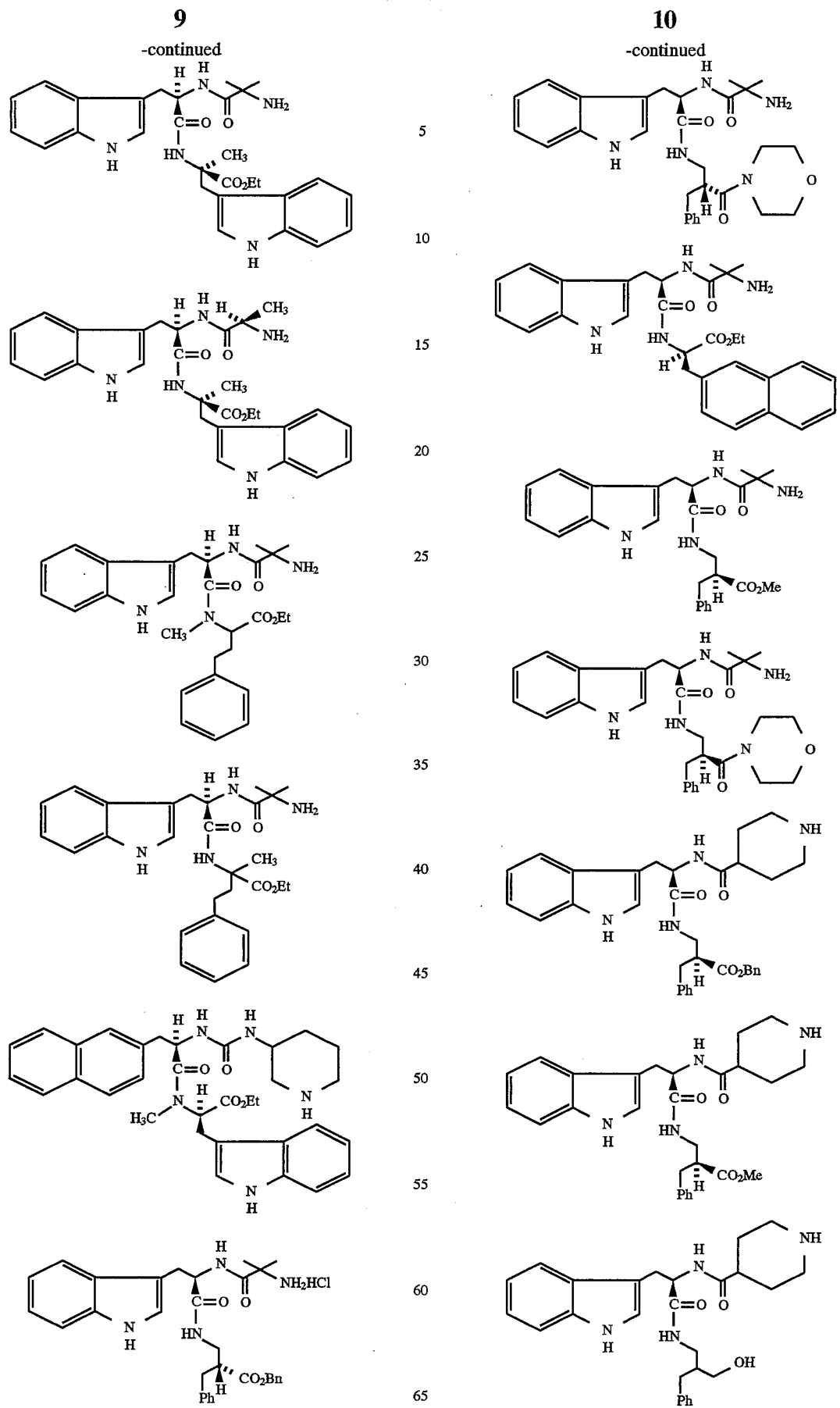

and their pharmaceutically acceptable salts and individual diasteromers thereof, where not otherwise specified.

Particularly preferred salts include the hydrochloride salts.

Throughout the instant application, the following abbreviations are used with the following meanings:
BOC t-butyloxycarbonyl
BOP Benzotriazol-1-yloxy tris/dimethylamino)-phosphonium hexafluorophosphate
CBZ Benzyloxycarbonyl
DIBAL-H diisobutylaluminum hydride
DMF N,N-dimethylformamide
EDC 1-(3-dimethylaminopropyl)-3-ethylcarbodiimide hydrochloride
FAB -MS Fast atom bombardment-mass spectroscopy
GHRP Growth hormone releasing peptide
HOBT Hydroxybenztriazole
LAH Lithium aluminum hydride
HPLC High pressure liquid chromatography
MHz Megahertz
MPLC Medium pressure liquid chromatography
NMM N-Methylmorpholine
NMR Nuclear Magnetic Resonance
PLC Preparative liquid chromatography
RPLC Reverse phase liquid chromatography
TFA Trifluoroacetic acid
THF Tetrahydrofuran
TLC Thin layer chromatography
TMS Tetramethylsilane The compounds of the instant invention all have at least one asymmetric center as noted by the asterisk in the structural Formula I above.

Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. Compounds which are more active as growth hormone secretagogues and, therefore are preferred, are those in which the nitrogen substituent is above and the $R_{1a}$ group is below the plane of the structure as represented in Formula II. An equivalent representation places $R_1$ and the N-substituent in the plane of the structure with the C=O group above the plane of the structure.

Formula II where $R_1$, $R_{1a}$, $R_{2a}$, $R_3$, $R_{3a}$, $R_4$, $R_5$, $R_6$, A, W and n are as defined above.

The configuration at the carbon atom bearing $R_1$ corresponds to that present in a D-amino acid. In most cases, this is also designated as an R-configuration although this will vary according to the value of $R_1$ used in making the R- or S- stereochemical assignments. Both absolute configurations at the carbon atom bearing W are consistent with activity when n is 1 and this is also true when n is 0, although the configuration corresponding to a (D)- amino acid is then preferred. The absolute stereochemistry of the compounds of this invention may be determined by the X-ray crystallography of crystalline products or crystalline intermediates which are derivatized, if necessary, containing an asymmetric center of known configuration.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention can be carried out in sequential or convergent synthetic routes. Syntheses detailing the preparation of the compounds of Formula I in a sequential manner are presented in the following reaction schemes. The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present are found in Greene, T; Wuts, P. G. M. *Protective Groups in Organic Synthesis*, John Wiley & Sons, Inc., New York, N.Y. (1991). CBZ and BOC were used extensively in the syntheses of this invention, and their removal conditions are known to those skilled in the art. Removal of CBZ groups can be achieved by a number of methods, for example, catalytic hydrogenation with hydrogen in the presence of palladium catalyst in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol, with a strong acid, such as trifluoroacetic acid (TFA) or hydrochloric acid (HCl).

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). The skills required in carrying out the reaction and purification of the resulting reaction products are known to those skilled in the art.

Conversion of 3 to intermediates 4 can be carried out as illustrated in Scheme 2 by removal of the protecting group L (CBZ, BOC, etc.)

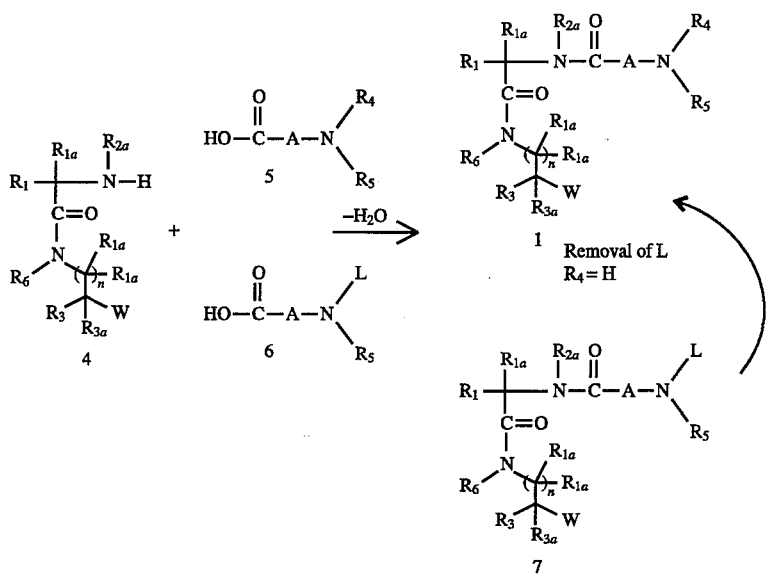

SCHEME 3

Purification procedures include crystallization, normal phase or reverse phase chromatography.

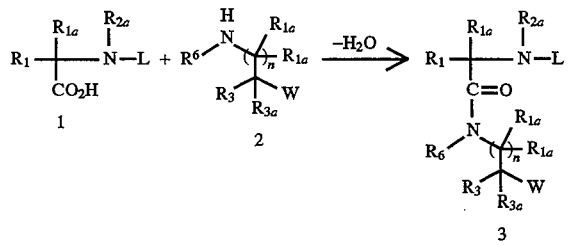

SCHEME 1

Intermediates of Formula 3 can be synthesized as described in Scheme 1. Coupling of amine of Formula 2, whose preparations are described later if they are not commercially available, to protected amino acids of Formula 1, wherein L is a suitable protecting group, is conveniently carried out under standard peptide coupling conditions.

Intermediates of Formula 5, wherein A is connected to the carbonyl by a carbon atom and thus A is —(CH$_2$)$_x$—C(R$_7$)(R$_{7a}$)—(CH$_2$)$_y$— can be coupled as shown in Scheme 3 to intermediates of Formula 4 under the standard peptide coupling reaction conditions. The amino acids 5, as amino acids 1, are either commercially available or can be synthesized. Also if R$_4$ or R$_5$ is a hydrogen then the protected amino acids 6 are employed in the coupling reaction, wherein L is a protecting group as defined above. Removal of L in 7 affords I, where R$_4$=H, can be carried out under conditions known in the art.

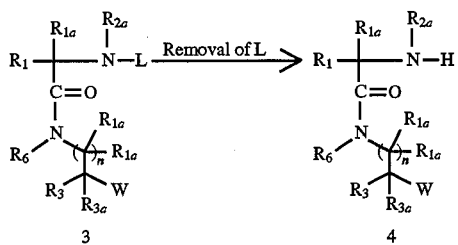

SCHEME 2

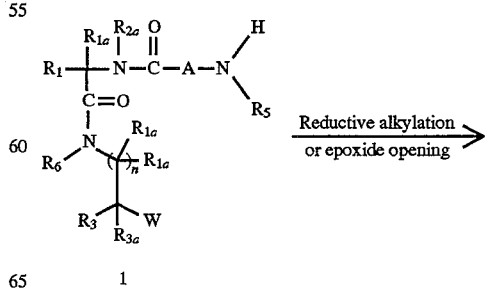

SCHEME 4

SCHEME 4

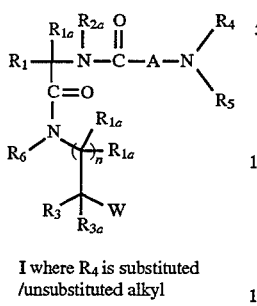

I where R$_4$ is substituted /unsubstituted alkyl

Compounds of Formula I wherein R$_4$ and/or R$_5$ is a hydrogen can be further elaborated to new compounds I (with preferred side chains R$_4$=CH$_2$—CH(OH)—CH$_2$X, wherein X=H or OH) which are substituted on the amino group as depicted in Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in an protic solvent such as methanol or ethanol in the present of catalytic amount of acid. Alternatively, a similar transformation can be accomplished via an epoxide opening reaction.

SCHEME 5

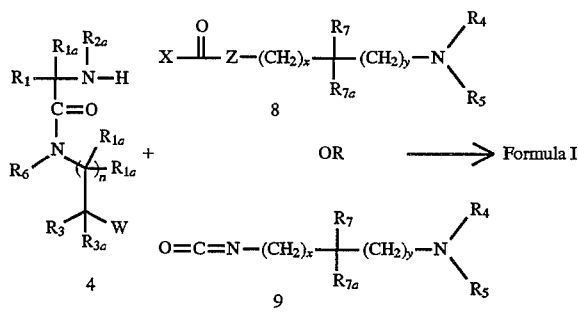

Compounds of Formula I, wherein A is Z—(CH$_2$)$_x$—C(R$_7$)(R$_{7a}$)—(CH$_2$)$_y$ and Z is N—R$_2$ or O can be prepared as shown in Scheme 5 by reacting 4 with reagents 8, wherein X is a good leaving group such as Cl, Br, I, or imidazole. Alternatively, 4 can be reacted with an isocyanate of Formula 9 in an inert solvent such as 1,2-dichloroethane results in compound of Formula I where Z is NH.

The compounds of general Formula I of the present invention can also be prepared in a convergent manner as described in reaction Schemes 6, 7 and 8.

SCHEME 6

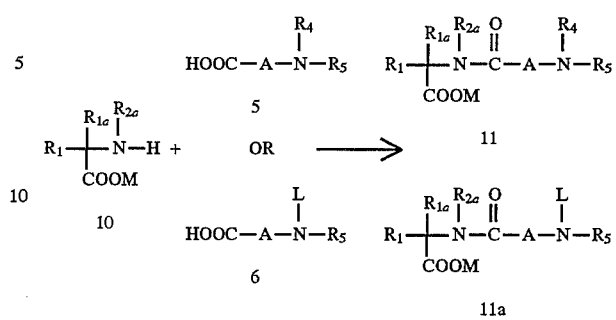

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other reactions includes the reaction of a protected amino acid with a diazoalkane, or with an alcohol and an acid activating agent such as EDC, DCC in the presence of a catalyst such as DMAP and removal of the protecting group L.

Intermediates of Formula 11 or 11a, can be prepared as shown in Scheme 6 by coupling of amino acid ester 10 to amino acids of Formula 5 or 6. When a urea or urethan linkage is present in 11 or 11a, it can be introduced as illustrated in Scheme 5.

SCHEME 7

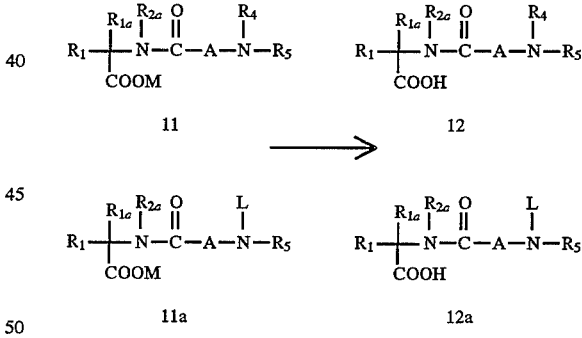

Conversion of the ester 11 or 11a to intermediate acids 12 or 12a can be achieved by a number of methods known in the art as described in Scheme 7; for example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.* 1982, 42, 587).

SCHEME 8

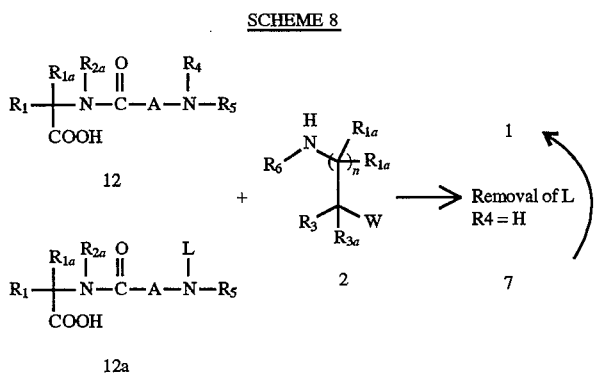

Acid 12 or 12a can then be elaborated to I or compound 7 as described in Scheme 8. Coupling amines of Formula 2 to acids of Formula 12 or 12a, wherein L is a suitable protecting group, is conveniently carried out under the standard peptide coupling reaction conditions. Transformation of 7 to I is achieved by removal of the protecting group L. When $R_4$ and/or $R_5$ is H, substituted alkyl groups may be optionally added to the nitrogen atom as described in Scheme 4.

Alternatively, the compounds of this invention can be synthesized by solid phase peptide synthesis.

Compounds of Formula 2:

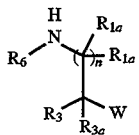

where W is carboxylic acid or derivative, are amino acids or derivatives, most of which are commercially available or known in the literature or they are simple conversion products thereof and can be prepared analogously to the known compounds. Some of the methods of synthesizing α-amino acids are noted above. The methods for the synthesis of β-amino acids are also well documented and these methods include the hydrolysis of substituted β-lactams to afford β-amino acids.

SCHEME 9

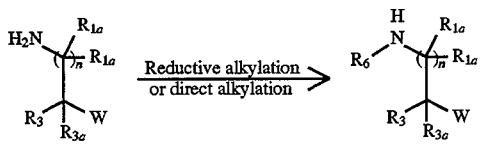

In cases where $R_6$ is not hydrogen, it can be introduced by direct alkylation with an alkylating reagent such as alkyl halide or by reductive alkylation with an aldehyde in a protic solvent such as methanol in the presence of a reducing agent such as sodium cyanoborohydride or under hydrogenation conditions in the presence of a noble metal catalyst such as palladium or its oxide. Alternatively $R_6$ can also be introduced by direct alkylation with alkyl halide of a N-protected amino acid by groups such t-BOC using a strong base such as sodium hydride in an inert solvent such as THF. The t-Boc protecting group can be conveniently removed after the alkylation.

SCHEME 10

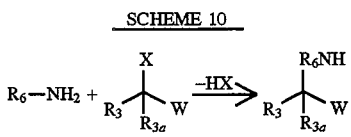

Alternatively, compounds of Formula 2 where n=0 can be prepared by reacting the amine $R_6NH_2$ with an α-halo carboxylic acid derivative in a inert solvent such as dichloromethane in the presence of a base such as diisopropylethyl amine. The amino acids or their derivatives generated by this synthetic protocols may be racemic. However, procedures for resolving RS-α-amino acid by various methods are known in the literature (Toone, E. J. and Jones, J. B. *Can. J. Chem.* 1987, 65, 2722; Okamoto, S.; Hijikato, A. *Biochem. Biophys. Res. Commun.* 1981, 101, 440; Greenstein, J. P.; Winitz, M. *Chemistry of the Amino Acids*; Wiley: New York, 1961, Vol. 1, 715–760). Therefore, the separated R- and S- isomers can be prepared by this methodology. Alternatively, the racemic derivatives can be converted directly to growth hormone secretagogues or their intermediates, and the resulting diastereomeric mixtures can be separated at the appropriate stage by chromatography to yield the enantiomerically pure compounds.

SCHEME 11

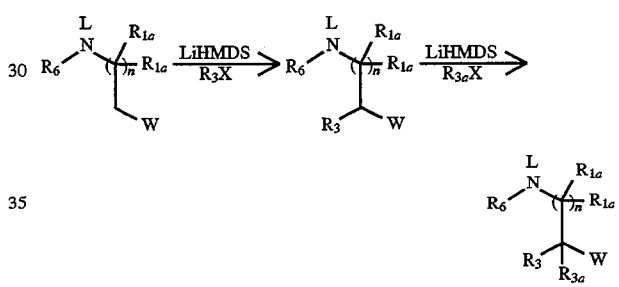

$R_3$ and $R_{3a}$ can be sequentially introduced by alkylation of the corresponding N-protected amino acid derivative where W is electron withdrawing group such as ester, amide, sulphone etc. and as shown in Scheme 11. The reaction can be carried out using LiHMDS as base in an inert solvent such as THF and HMPA and alkyl bromide.

When $W=CO_2H$ and it is desired to convert this group to ester, amide, acyl sulfonamide, and moieties as defined by W, these transformations can be made according to the conventional methods well documented in the literature and known to those skilled in the art (*The Practice of Peptide Synthesis*, by M. Bodanszky and A. Bodanszky, Springer-Verlag, 1984). For example, esters can be prepared by reacting the amino acid with an alcohol in the presence of an acid catalyst such as p-toluenesulfonic acid under azeotropic conditions. Alternatively, a removable protecting group L such as BOC or CBZ is put onto the NH to which $R_6$ is attached and the desired transformations are made of the carboxyl group. For example, a carboxyl group can be activated with reagents such as EDC, DCC and BOP in an inert solvent such as dichloromethane in the presence of a catalyst such as DMAP or HOBT and then reacted with alcohols or amines to provide esters and amides respectively.

The carboxylic acid can also be converted into its next higher homologue, or to a derivative of the homologous acid, such as amide or ester by an Arndt-Eistert reaction. Alternatively, the ester can be directly homologated by the protocol using ynolate anions described by C. J. Kowalski and R. E. Reddy in *J. Org. Chem.* 1992, 57, 7194–7208. The resulting acid and/or ester can be converted to the next higher homologue, and so on and so forth.

SCHEME 12

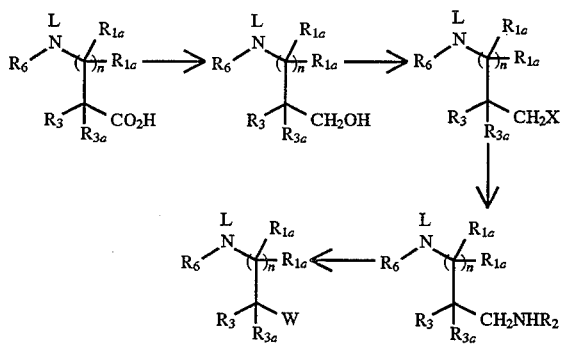

Reduction of a carboxyl group with a reducing agent such as borane or DIBALH as shown in Scheme 12 affords the corresponding alcohol which can be alkylated or esterified or converted to a reactive leaving group X using, for example, mesyl chloride. Displacement of the X group with amines or equivalents affords amino products or intermediates which may, in turn, be further reacted with sulfonyl chlorides, acyl chlorides or isocyanates to produce sulfonamides, amides or ureas as defined by W.

SCHEME 13

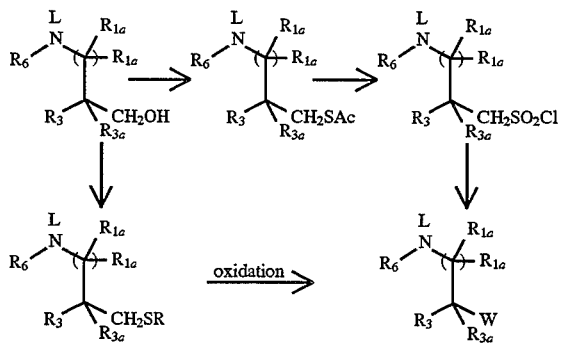

As illustrated in Scheme 13, displacement of the X group with thiols or thiocarboxylic acid affords thioether or thio ester products. Alternatively, the thioethers and thioesters can be prepared directly from the alcohol under the Mitsunobu reaction conditions (Volante, R. P. *Tetrahedron Lett.* 1981, 22, 3119–3122). Thioethers can be oxidized, for example, to sulfoxides with sodium periodate and to sulfones with OXONE®. Thioesters can be converted to thiols which can be oxidized by chlorine to afford sulfonyl chloride which can be converted to sulfonamide by reacting with amine.

Other functional group transformations which are required to generate the groups specified by W including homologation reactions and the formation of tetrazoles and oxadiazoles are well known in the art and, for example, are to be found in the annual volumes of *Theilheimer's Synthetic Methods of Organic Chemistry*. When W is hydrogen in Formula 2, most of the amines of Formula 2 are known in the literature or they can be prepared by standard methods, for example, by the reduction of nitriles or carboxamides, the reductive amination of aldehydes or ketones or by the reaction of alkyl or arylalkyl halides with ammonia or with a primary or secondary amine.

The compounds of the present invention may be prepared from a variety of substituted natural and unnatural amino acids of Formulas 31. The preparation of many of these acids is described in e.g., U.S. Pat. Nos 5,206,235, 5,283,241, 5,284,841, 5,310,737 and 5,317,017. The preparation of these intermediates in racemic form is accomplished by classical methods familiar to those skilled in the art (Williams, R. M. "*Synthesis of Optically Active α-Amino Acids*" Pergamon Press: Oxford, 1989; Vol. 7). Several methods exist to resolve (DL)-

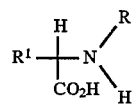 31 amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.*, 111, 6354–6364 (1989).

When it is desirable to synthesize these intermediates in optically pure form, established methods include: (1) asymmetric electrophilic amination of chiral enolates (*J. Am. Chem. Soc.*, 108, 6394–6395, 6395–6397, and 6397–6399 (1986)), (2) asymmetric nucleophilic amination of optically active carbonyl derivatives, (*J. Am. Chem. Soc.*, 114, 1906 (1992); *Tetrahedron Lett.*, 28, 32 (1987)), (3) diastereoselective alkylation of chiral glycine enolate synthons (*J. Am. Chem. Soc.*, 113, 9276 (1991); *J. Org. Chem.*, 54, 3916 (1989)), (4) diastereo-selective nucleophilic addition to a chiral electrophilic glycinate synthon (*J. Am. Chem. Soc.*, 108, 1103 (1986)), (5) asymmetric hydrogenation of prochiral dehydroamino acid derivatives (*Asymmetric Synthesis, Chiral Catalysis*; Morrison, J. D., Ed; Academic Press: Orlando, Fla.; Vol 5 (1985)), and (6) enzymatic syntheses (*Angew. Chem. Int. Ed. Engl.*, 17, 176 (1978)).

SCHEME 14

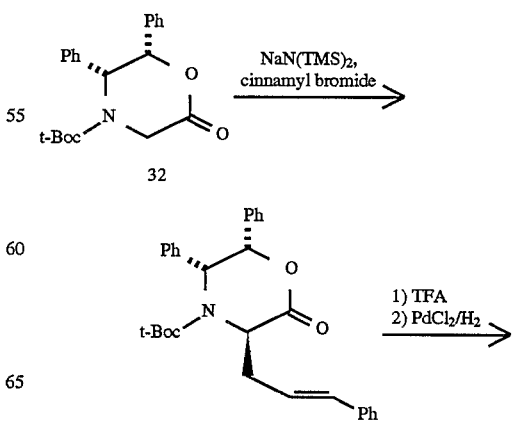

-continued
SCHEME 14

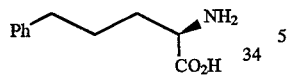

For example, alkylation of the enolate of diphenyloxazinone 32 (*J. Am. Chem. Soc.*, 113, 9276 (1991)) with cinnamyl bromide in the presence of sodium bis(trimethylsilyl) amide proceeds smoothly to afford 33 which is converted into the desired (D)-2-amino-5-phenylpentanoic acid 34 by removing the N-t-butyloxycarbonyl group with trifluoroacetic acid and hydrogenation over a PdCl₂ catalyst (Scheme 14).

SCHEME 15

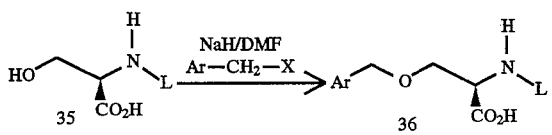

Intermediates of Formula 31 which are O-benzyl-(D)-serine derivatives 36 are conveniently prepared from suitably substituted benzyl halides and N-protected-(D)-serine 35. The protecting group L is conveniently a BOC or a CBZ group. Benzylation of 35 can be achieved by a number of methods well known in the literature including deprotonation with two equivalents of sodium hydride in an inert solvent such as DMF followed by treatment with one equivalent of a variety of benzyl halides (*Synthesis*, 36 (1989)) as shown in Scheme 15.

The O-alkyl-(D)-serine derivatives may also be prepared using an alkylation protocol. Other methods that could be utilized to prepare (D)-serine derivatives of Formula 36 include the acid catalyzed benzylation of carboxyl protected intermediates derived from 35 with reagents of formula ArCH₂OC(=NH)CCl₃ (O. Yonemitsu et al., *Chem. Pharm. Bull.*, 36, 4244 (1988)). Alternatively, alkylation of the chiral glycine enolates (*J. Am. Chem. Soc.*, 113, 9276 (1991); *J. Org. Chem.*, 54, 3916 (1989)) with ArCH₂OCH₂X where X is a leaving group affords 36. In addition D,L-O-aryl(alkyl) serines may be prepared and resolved by methods described above.

SCHEME 16

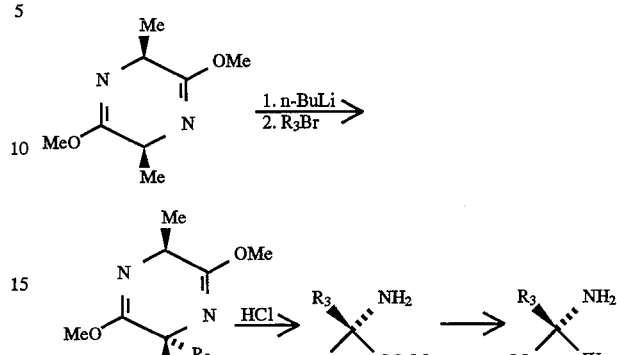

The asymmetric synthesis of α,α-disubstituted amino acids can be achieved by the bislactim chemistry developed by Schollkopf and coworkers (Schollkopf, U., *Tetrahedron*, 39, 2085 (1983)) as illustrated in Scheme 16. Thus, the readily available optically active bislactim can be alkylated with an alkyl or arylalkyl halide to obtain the intermediate shown with high asymmetric induction due to the presence the other methyl group which directs the R₃ group trans to it. Hydrolysis of this alkylated product yields the α-methyl amino acid methyl ester. The resulting methyl ester can be converted to groups as defined by W through conventional chemistry as discussed before. Shown in the scheme was the preparation of one enatiomer of the α-methyl amino acid, the other enatiomer can be prepared in a similar way from starting material of the opposite stereochemistry.

Alternatively, the asymmetric synthesis of α,α-disubstituted amino acids can be achieved by the alkylation of the Schiff base of L-alanine methyl ester and chiral auxiliary 1,2,3,4-di-O-cyclohexylidene-α-D-galacto-hexo-1,5-dialdopyranose which was also developed by Schollkopf and coworkers (*Synthesis*, 789 (1983)). The chiral auxiliary is removed by acid hydrolysis to yield the desired α-methyl amino acids.

SCHEME 17

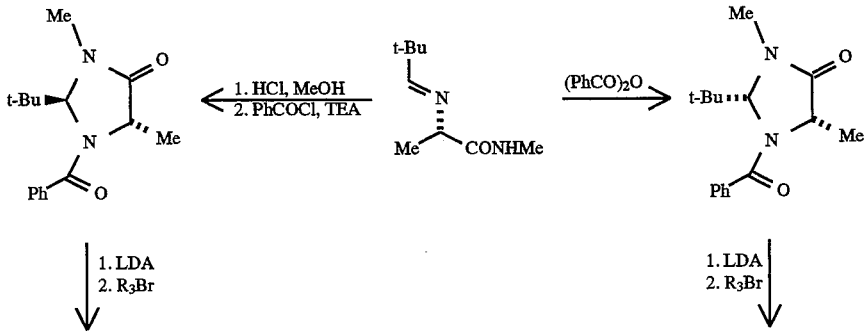

-continued
SCHEME 17

Another asymmetric synthesis of α-methyl amino acids can be achieved by the methods developed by Seebach and coworkers which involves reproduction of chirality without using a chiral auxiliary (Naef. R, and Seebach, D., Helv. Chim. Acta., 68, 135 (1985)) as shown in Scheme 17. The Schiff base of trimethylace-taldehyde and L-AlaNHMe can be converted to the two imidazolindinones as shown in the scheme under different reaction conditions. Alkylation and acid hydrolysis yields the amino acids. Thus both enatiomers of the amino acid can be prepared from the same intermediate.

The compounds of general Formula 2 (n=1) of the present invention are either commercially available or known compounds which can be prepared by literature procedures. Illustrated here are some, but by no means all the methods available for their preparation. For example, the synthesis of α-substituted β-amino acids and α,β-disubstituted β-amino acids can be prepared from the nucleophilic addition of an excess of hydroxyamine to the corresponding α- or β-substituted α, β-unsaturated acids (*Organic Syntheses*, Collect. Vol. III; Wiley: New York, 91 (1955)).

SCHEME 18

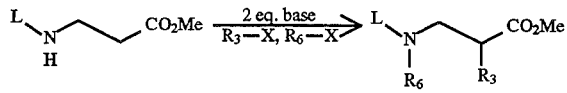

In addition, the synthesis of α-substituted-β-amino acids can be prepared from alkylation of a dianion of β-alanine as detailed in Scheme 18 involving stepwise alkylation first of the more reactive carbon anion. In these two procedures, the β-amino acids are obtained in racemic form. Several methods exist to resolve (D,L) amino acids. One of the most common methods is to resolve an amino or carboxyl protected intermediate by crystallization of salts derived from optically active acids or amines.

SCHEME 19

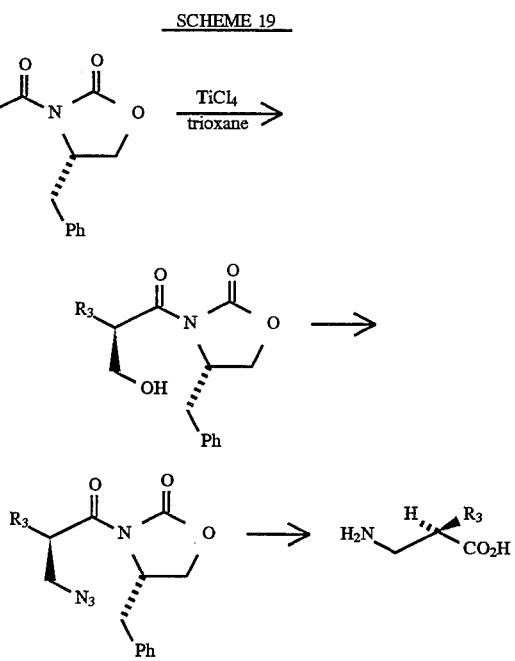

Alternatively, the asymmetric synthesis of enantiomerically pure β-amino acids is available. For example, E. Juaristi and J. Escalante (*J. Org. Chem.*, 58, 2282 (1993)) have used 1-benzoyl-3,6-(S)-dimethylperhydropyrimidin-4-one as an intermediate to synthesize in enantiomerically pure form α,β-disubstituted-β-amino acids. Specifically, the synthesis of a single enantiomer of α-substituted-β-amino acids can be achieved by 1,4-asymmetric induction in the alkylation of a titanium enolate (D. A. Evans et al., *J. Am. Chem. Soc.*, 112, 8215 (1990)) as detailed in Scheme 19. Removal of the chiral template from the alkylation product can be carried out by a number of methods familiar to those skilled in the art, including the lithium benzyloxide protocol detailed by D. A. Evans et al., *J. Am. Chem. Soc.*, 104, 1737 (1982)).

SCHEME 20

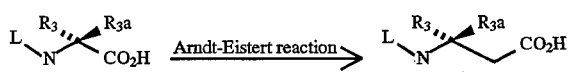

β-Substituted-β-amino acids or β, β-disubstituted-β-amino acids can be obtained from the corresponding α-amino acids or α-substituted amino acids with full retention of configuration using the Arndt-Eistert method (*Tetrahedron*, 43, 3509, (1987)) depicted in Scheme 20. The α-amino acids and α-substituted amino acids can be prepared by methods familiar to those skilled in the art, including the procedures described in Schemes 16 and 17. The protecting group L can be removed through conventional chemistry. The natural and unnatural amino acids of general Formula 2 can be elaborated to compounds of Formula I by using chemistry described above.

It is noted that in some situations the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., *Science*, 260, 1640–1643 (1993) (see text of FIG. 2 therein). In particular, the intrinsic growth horomone secretagogue activities of the compounds of the present invention may be demonstrated in this assay. The compounds of the following examples have activity in the aforementioned assay in the range of 1 nm to 5 μm.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release and that the growth hormone releasing factor (GRF) stimulates its release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox. or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. No. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia, treatment of peripheral neuropathies; replacement of growth hormone in stressed patients; treatment of osteochondrody-splasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and prevention of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock.

In particular, the instant compounds are useful in the prevention or treatment of a condition selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drag and alcohol withdrawal symptoms, drag addiction, and fertility problems.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T., "Role of Bisphosphonates in Metabolic Bone Diseases" *Trends in Endocrinol. Metab.*, 4, 19–25 (1993). Bisphosphonates with these utilities include alendronate, tiludronate, dimethyl-APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone.

The following examples are provided for the purpose of further illustration only and are not intended to be limitations on the disclosed invention.

INTERMEDIATE 1

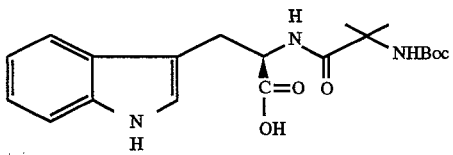

Step A:

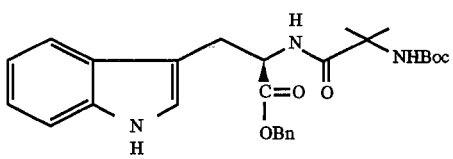

To 5.0 g (16.5 mmole) of the commercially available N-t-BOC-D-tryptophan in 100 mL of chloroform was added 1.80 mL (16.5 mmole) of benzyl alcohol, 0.20 g (1.65 mmole) of 4-N,N-dimethylamino pyridine (DMAP), and 3.20 g of EDC and stirred for 16 h. The reaction mixture was poured into 100 mL of water and the organic layer was separated. The aqueous was further extracted with 2×100 mL of chloroform. The combined organic solution was washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organic solution were washed with brine (100 mL), dried over potassium carbonate, filtered, and concentrated to give 5.46 g of the amine as a brown oil which was used without purification.

To 5.46 g of the above product in 100 mL of chloroform was added 3.40 g (22.2 mmole) of HOBT, 4.60 g (22.2 mmole) of N-BOC-α-methyl alanine, and 5.32 g (28.0 mmole) of EDC and stirred for 16 h. The reaction mixture was poured into 100 mL of water and the organic layer was separated. The aqueous was further extracted with 2×100 mL of chloroform. The combined organic solution were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g SiO$_2$; hexane-ethyl acetate as eluent) gave 4.75 g of the desired material as a colorless foam.

$^1$H NMR (CDCl$_3$, 200 MHz) δ 8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H).

Step B:

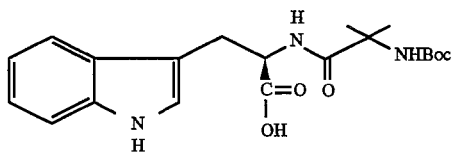

To a solution of 4.75 g of the material from Step A in 100 mL of ethanol was added 1.0 g of 10% Pd/C and stirred at RT under a H$_2$ balloon for 18 h. The catalyst was filtered off through a pad of celite and washed with ethyl acetate. The filtrate was concentrated to give 2.96 g of the acid as a colorless foam.

$^1$H NMR (CDCl$_3$, 200 MHz) δ 8.60 (bs, 1H), 7.55 (d, 1H), 7.26–6.90 (m, 3H), 6.88 (bd, 1H), 4.80 (m, 1H), 3.32 (2dd, 2H), 1.37 (s, 3H), 1.35 (s, 12H).

INTERMEDIATE 2

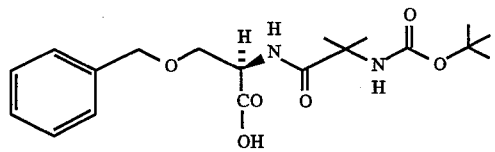

Step A:

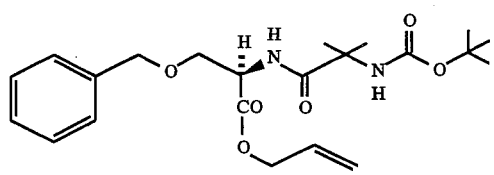

Prepared from N-tBOC-O-benzyl-D-serine and allyl alcohol by the procedure described in Intermediate 1, Step A and subsequent coupling to N-BOC-α-methylalanine to give the desired compound.

$^1$H NMR (400 MHz, CDCl$_3$) δ 7.25 (s, 5H), 5.8 (m, 1H), 5.2 (dd, 2H), 5.0 (bs, 1H), 4.7 (m, 1H), 4.6 (m, 2H), 4.4 (dd, 2H), 3.9 (dd, 1H), 3.6 (dd, 1H), 1.45 (d, 6H), 1.39 (s, 9H).

Step B:

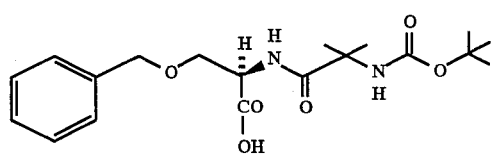

To a stirred solution of the crude intermediate obtained in Step A (6.7 g, 15.9 mmol), tetrakis (triphenylphosphine)-palladium (1.8 g, 0.1 eq) and, triphenyl phosphine (1.25 g, 0.3 eq) was added a solution of potassium-2-ethyl hexanoate (35 mL, 0.5M solution in EtOAc). The reaction mixture was stirred at room temperature under nitrogen atmosphere for 1 h and then diluted with ether (100 mL) and poured into ice-water. The organic layer was separated and the aqueous fraction was acidified with citric acid (20%), then extracted with EtOAc. The EtOAc extracts were washed with brine, dried over magnesium sulfate, filtered and evaporated to give the title compound as a solid.

$^1$H NMR (400 Hz, CD$_3$OD) δ 7.3 (s, 5H), 4.7 (m, 1H), 4.5 (s, 2H), 4.0 (m, 1H), 3.6 (m, 1H), 1.4 (d, 6H), 1.3 (s, 9H).

INTERMEDIATE 3

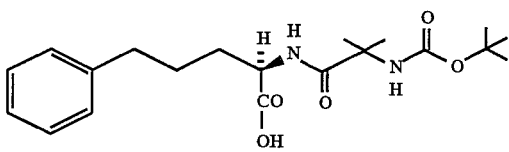

This intermediate was synthesized as described in Step A and B of Intermediate 1, but (2R)-N-t-BOC-5-phenylpentanoic acid (H. K. Chenault et al., *J. Am. Chem. Soc.*, 111, 6354–6364 (1989)) was used in place of N-t-BOC-(D)-Tryptophan.

$^1$H NMR (CDCl$_3$, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

EXAMPLE 1

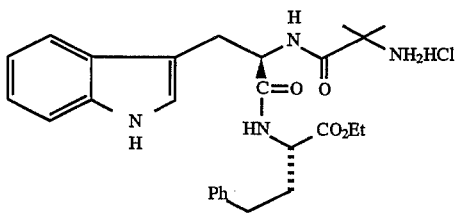

Step A

L-HomoPhe Ethyl Ester Hydrochloride

Thionyl chloride (0.41 mL, 5.58 mmol) was added slowly into stirred ethanol (20 mL) at 0°, the mixture was stirred for 10 min., and to which was added L-HomoPheOH (1 g, 5.58 mmol). The mixture was refluxed for 2 hours and then allowed to cool to room temperature. The material was then concentrated and taken to dryness in vacuo to give the title compound (1.35 g).

Step B:

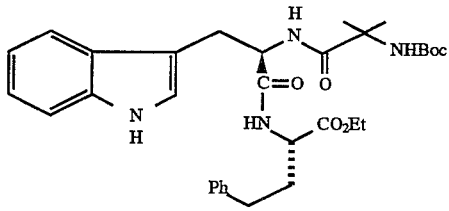

To a solution of L-HomoPhe ethyl ester hydrochloride (75 mg, 0.255 mmol), Intermediate 1 (100 mg, 0.255 mmol), HOBT (34 mg), N-methylmorpholine (0.033 mL) in dichloromethane (15 mL) was added EDC (100 mg). The reaction mixture was stirred at room temperature overnight. The solution was diluted with ethyl acetate and washed subsequently with water, saturated sodium bicarbonate solution, and saturated sodium chloride solution, dried over anhydrous magnesium sulfate; then filtered and concentrated. Purification by MPLC eluting with 60% ethyl acetate in hexane provided the desired compound (120.6 mg).

FAB-MS calc. for C$_{32}$H$_{42}$N$_4$O$_6$: 578; found: 579 (M+H).

Step C:

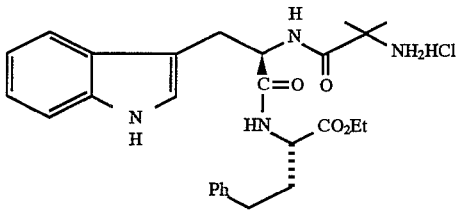

A solution of the intermediate from previous step (120 mg) in ethyl acetate (5 mL) was cooled to 0° C. While stirring, hydrogen chloride gas was bubbled into the mixture until saturation occurred. The reaction was stirred for 15 minutes, until TLC analysis indicated that the reaction was complete. The solution was then concentrated to remove the ethyl acetate. The residue was then redissolved in dichloromethane and hexane was added followed by evaporation in vacuo to afford the product as a solid (100 mg).

FAB-MS calc. for C$_{27}$H$_{34}$N$_4$O$_4$: 478; found: 479 (M+H).
$^1$HNMR (400 MHz, CD$_3$OD): 8.29, 8.05 (2d, 1H), 7.64 (d, J=7.5 Hz, 1H), 7.30–7.00 (m, 9H), 4.85 (m, 1H), 4.23–4.17 (m, 1H), 4.11 (q, J=7.1 Hz, 2H), 3.34–3.10 (dd, J1=7.1 Hz, 1H), 3.16 (dd, J=8.2 Hz, 14.2 Hz, 1H), 2.34–2.29 (m, 2H), 1.95–1.89 (m, 1H), 1.79–1.74 (m, 1H), 1.56 (s, 3H), 1.39 (s, 3H),1.22 (t, J=7 Hz, 3H).

EXAMPLE 2

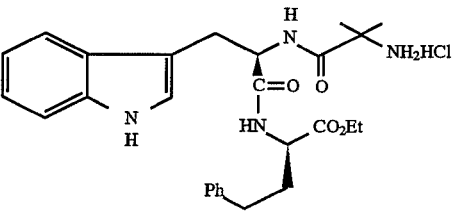

Step A:

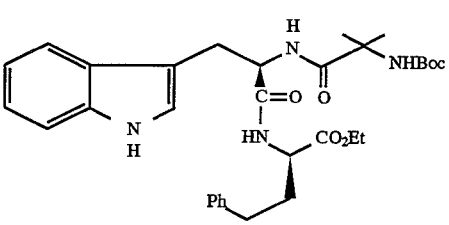

Prepared by the procedure described in Example 1, Step B from D-HomoPhe ethyl ester hydrochloride (75 mg, 0.255 mmol), Intermediate 1 (100 mg, 0.255 mmol), HOBT (34 mg.), N-methyl morpholine(0.033 mL; 0.255 mmol), and EDC (100 mg). Product: 108 mg. FAB-MS calc. for C$_{32}$H$_{42}$N$_4$O$_6$: 578; found: 579 (M+H).

Step B:

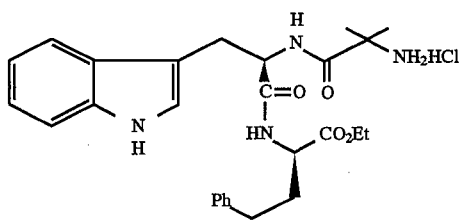

Prepared by the procedure described in Example 1, Step C from the intermediate from previous step (106 mg) and HCl gas in ethyl acetate (3 mL) at 0° C. Reaction time: 1 hour. Product: 94.5 mg.

FAB-MS calc. for $C_{27}H_{34}N_4O_4$: 478; found: 479 (M+H). $^1$HNMR (400 MHz, $CD_3OD$): 8.54, 7.98 (2d, 1H), 7.67 (d, J-7.7 Hz, 1H), 7.32 (d, J=8.1 Hz, 1H), 7.27–7.14 (m, 6H), 7.08 (t, J=7.1 Hz, 1H), 7.01 (t, J=7.1 Hz, 1H), 4.85 (m, 1H), 4.38–4.33 (m, 1H), 4.13 (q, J=7.1 Hz, 2H), 3.36 (dd, J=5.4 Hz, 14.5 Hz, 1H), 3.16 (dd, J=9.5 Hz, 14.5 Hz, 1H), 2.73–2.59 (m, 2H), 2.13–2.07 (m, 1H), 2.03–1.96 (m, 1H), 1.54 (s, 3H), 1.31 (s, 3H),1.24 (t, J=7.1 Hz, 3H).

The additional products shown in Table I were prepared according to Example 1 Steps A, B and C from the corresponding α-methyl amino acid instead of L-homoPheOH.

TABLE I
ADDITIONAL EXAMPLES

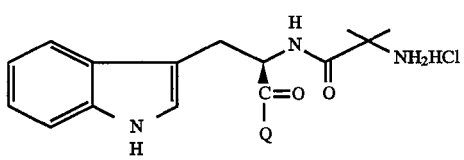

| entry | Q | MF FAB-MS (M + 1) |
|---|---|---|
| 1 | ![](HN-CO2Et, Me, CH2CH2Ph) | $C_{28}H_{36}N_4O_4$ 493 |
| 2 | ![](HO-C6H4-CH2CH2-, HN-CO2Et, Me) | $C_{28}H_{36}N_4O_5$ 509 |
| 3 | ![](MeO-C6H4-CH2CH2-, HN-CO2Et, Me) | $C_{29}H_{38}N_4O_5$ 523 |
| 4 | ![](MeO, MeO-C6H3-CH2CH2-, HN-CO2Et, Me) | $C_{30}H_{40}N_4O_6$ 553 |

The additional products shown in Table IA were prepared according to Example 1 Steps B and C, or Example 2 Steps A and B, using Intermediate 2 and Intermediate 3 and D or L-homophenyl-alanine ethyl ester.

TABLE IA
ADDITIONAL EXAMPLES

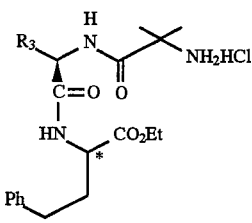

| entry | $R_3$ | * | MF FAB-MS (M + 1) |
|---|---|---|---|
| 1 | $PhCH_2CH_2CH_2$— | D | $C_{27}H_{37}N_3O_4$ 468 |
| 2 | $PhCH_2CH_2CH_2$— | L | $C_{27}H_{37}N_3O_4$ 468 |
| 3 | $PhCH_2OCH_2$— | D | $C_{26}H_{35}N_3O_5$ 470 |
| 4 | $PhCH_2OCH_2$— | L | $C_{26}H_{35}N_3O_5$ 470 |

EXAMPLE 2A

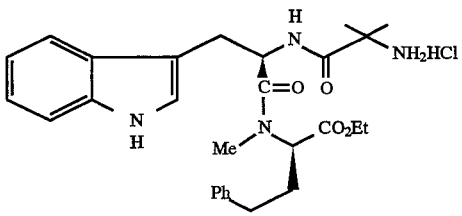

Step A

N-Me-D-homoPheOEt

To a suspension of sodium hydride (60%, 458 mg, washed with hexane) in THF (3 mL) at room temperature under Ar, was added D-Boc-homoPhOH (533 mg, 1.9 mmol) in THF (2 mL) via a syringe. After stirring for 5 minutes, iodomethane (1.43 mL) was added and the resulting mixture was stirred at room temperature overnight. The reaction mixture was slowly added to 1N sodium bisulfate solution then it was extracted with ethyl acetate twice. The combined organic solution was dried over magnesium sulfate, evaporated to give a brown solid (700 mg, crude) which was used without further purification. The solid obtained was dissolved in ethyl acetate (3 mL). HCl gas was bubbled through the solution until it was saturated at 0° C. The reaction mixture was stirred for additional 15 minutes, and it was evaporated to dryness to give N-Me-D-homophenylalanine. The resulting amino acid was dissolved in 20 mL of acidic ethanol and refluxed for two hours. The solution was evaporated to give the desired product.

Step B:

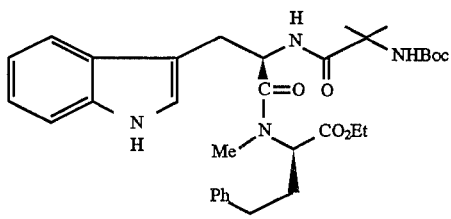

Prepared by the procedure described in Example 1, Step B from the intermediate from the previous step (200 mg), Intermediate 1 (200 mg, 0.514 mmol), HOBT (68 mg.), N-methyl morpholine(0.066 mL; 0.514 mmol), and EDC (200 mg). Product: 235.2 mg.

FAB-MS calc. for $C_{33}H_{44}N_4O_6$: 592; found: 593 (M+H).

Step C:

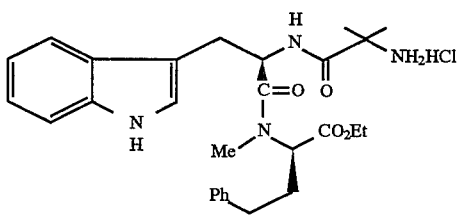

Prepared by the procedure described in Example 1, Step C from the intermediate from previous step (204 mg) and HCl gas in ethyl acetate (3 mL) at 0° C. Reaction time: 30 minutes. Product: 186 mg.

FAB-MS calc. for $C_{28}H_{36}N_4O_4$: 492; found: 493 (M+H).

EXAMPLE 3

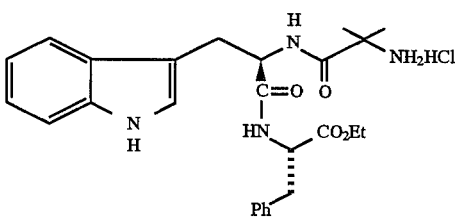

Step A:

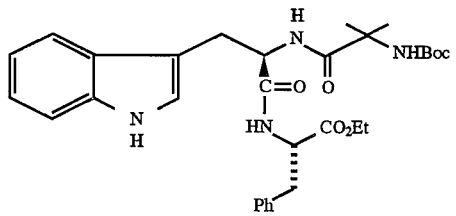

Prepared by the procedure described in Example 1, Step B from L-Phe ethyl ester hydrochloride (176 mg, 0.771 mmol), Intermediate 1 (200 mg, 0.514 mmol), HOBT (64), N-methyl morpholine(0.068 mL, 0.514 mmol), and EDC (200 mg, 1.03 mmol).

Product: 246 mg. FAB-MS calc. for $C_{31}H_{40}N_4O_4$: 464; found: 465 (M+H). ¹HNMR (400 MHz, CD₃OD): 8.73 (br. s., 1 H), 7.57 (d, J=2.3 Hz, 1H), 7.40–7.00 (m, 9H), 6.97 (s, 1H), 6.71 (br. d, 1H), 4.86 (s, 1H), 4.68 (dd, J=6 Hz, 14 Hz, 1H), 4.59 (dd, J=7.3 Hz, 14.3 Hz, 1H), 4.0 (q, 2H), 3.36 (dd, J=5.5 Hz, 14.7 Hz, 1H), 3.20 (dd, J=5.5 Hz, 14.6 Hz, 1H), 2.97 (br. d., J=6.5 Hz, 1H), 1.38 (s, 3H), 1.29 (s, 9H), 1.18 (s, 3H), 1.08 (t, J=7 Hz, 3H).

Step B:

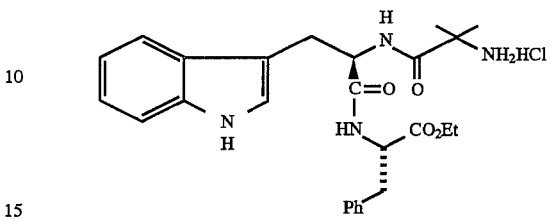

Prepared by the procedure described in Example 1, Step C from the intermediate from previous step (240 mg) and HCl gas in ethyl acetate (5 mL) at 0° C. Reaction time: 20 minutes. product: 152.5 mg.

FAB-MS calc. for $C_{26}H_{32}N_4O_4$: 464; found: 465 (M+H). ¹HNMR (400 MHz, CD₃OD): 8.24–6.94 (m, 11H), 4.79–4.74 (m, 1H), 4.64–4.59 (m, 1H), 4.10 (q, J=7.1 Hz, 2H), 3.11 (dd, J=6 Hz, 14.6 Hz, 1H), 3.01–2.92 (m, 2H), 2.81(dd, J=8.4 Hz, 13.8 Hz, 1H), 1.49 (s, 3H), 1.29 (s, 3H), 1.18 (t, J=7 Hz, 3H).

EXAMPLE 4

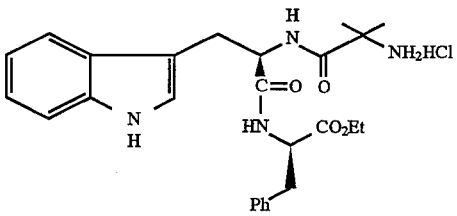

Step A:

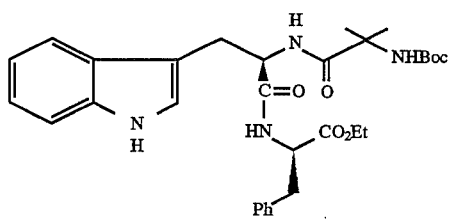

Prepared by the procedure described in Example 1, Step B from D-phenylalanine ethyl ester hydrochloride (176 mg, 0.771 mmol), Intermediate 1 (200 mg, 0.514 mmol), HOBT (1 eq.), N-methyl morpholine(0.068 mL, 0.514 mmol), and EDC (200 mg, 1.03 mmol).

Product: 287 mg. FAB-MS calc. for $C_{31}H_{40}N_4O_4$: 464; found: 465 (M+H).

Step B:

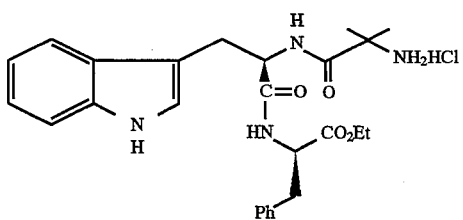

Prepared by the procedure described in Example 1, Step C from the intermediate from previous step (280 mg) and HCl gas in ethyl acetate (10 mL) at 0° C. Reaction time: 20 minutes. Product: 231.7 mg.

FAB-MS calc. for $C_{26}H_{32}N_4O_4$: 464; found: 465 (M+H). $^1$HNMR (400 MHz, $CD_3OD$): 8.29–6.94 (m, 11H), 4.79–4.75 (m, 1H), 4.64–4.59 (m, 1 H), 4.10–4.05 (m, 2H), 3.27–2.96 (m, 4H), 1.49 (s, 3H), 1.28 (s, 3H), 1.19–1.15 (m, 3H).

The additional examples shown in Table II were prepared according to Example 1 Steps B and C, using Intermediate 1 and commercially available intermediates. The intermediate for entry 6 was prepared by removing the BOC group from Intermediate 1, Step A using HCl gas in ethyl acetate at 0° C.

TABLE II

ADDITIONAL EXAMPLES

| entry | Q | MF FAB-MS (M + 1) |
|---|---|---|
| 1 | HN—CH₂—CO₂Et | $C_{19}H_{26}N_4O_4$ 375 |
| 2 | Me-N(—CO₂Et)— | $C_{20}H_{28}N_4O_4$ 389 |
| 3 | Ph(CH₂)₃NH— | $C_{24}H_{30}N_4O_2$ 407 |
| 4 | HN—CH(CO₂Et)—CH₂—C₆H₄F | $C_{26}H_{31}N_4O_4F$ 483 |
| 5 | HN—CH(CO₂Et)—CH₂—CO₂Et | $C_{23}H_{32}N_4O_6$ 461 |

TABLE II-continued

ADDITIONAL EXAMPLES

| entry | Q | MF FAB-MS (M + 1) |
|---|---|---|
| 6 | (benzyl ester of tryptophan linked through amide) | $C_{37}H_{42}N_6O_5$ 651 |

EXAMPLE 5

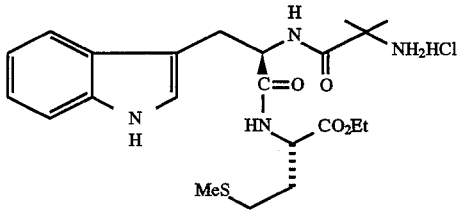

Step A:

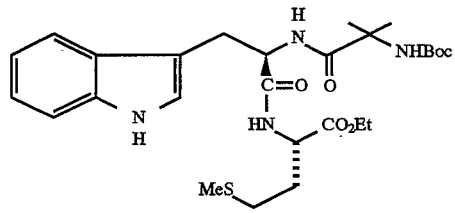

Prepared by the procedure described in Example 1, Step B from L-methionine ethyl ester hydrochloride (165 mg, 0.771 mmol), Intermediate 1 (200 mg, 0.514 mmol), HOBT (1 eq.), N-methyl morpholine(0.068 mL, 0.514 mmol), and EDC (200 mg, 1.03 mmol).

Product: 262 mg. FAB-MS calc. for $C_{27}H_{40}N_4O_6S$: 548; found: 549 (M+H).

Step B:

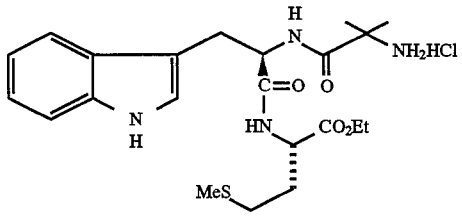

Prepared by the procedure described in Example 1, Step C from the intermediate from previous step (250 mg) and HCl gas in ethyl acetate (10 mL) at 0° C. Reaction time: 20 minutes. Product: 209.4 mg.

FAB-MS calc. for $C_{22}H_{32}N_4O_4S$: 448; found: 449 (M+H). $^1$HNMR (400 MHz, $CD_3OD$): 8.26–6.99(m, 6H), 4.82–4.78 (m, 1H), 4.42–4.37 (m, 1 H), 4.14 (q, J=7 Hz, 2H), 3.31–3.26(dd, 2H), 3.14 (dd, J=8.0 Hz, 2H), 2.20–2.10 (m, 2H), 1.98 (s, 3H), 1.96–1.87 (m, 1H), 1.81–1.73 (m, 1H), 1.56 (s, 3H), 1.39 (s, 3H), 1.24 (t, J=7 Hz, 3H).

EXAMPLE 6

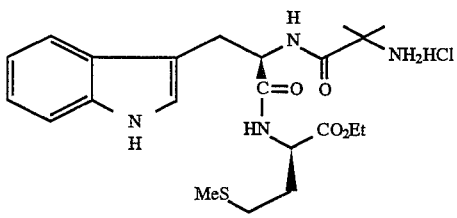

Step A:

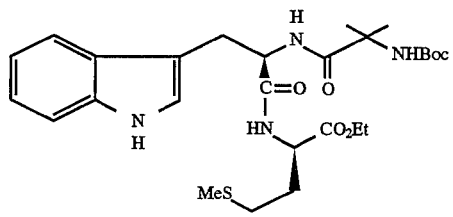

Prepared by the procedure described in Example 1, Step B from D-methionine ethyl ester hydrochloride (165 mg, 0.771 mmol), Intermediate 1 (200 mg, 0.514 mmol), HOBT (1 eq.), N-methyl morpholine (0.068 mL, 0.514 mmol), and EDC (200 mg, 1.03 mmol).

Product: 243 mg. FAB-MS calc. for $C_{27}H_{40}N_4O_6S$: 548; found: 549 (M+H).

Step B:

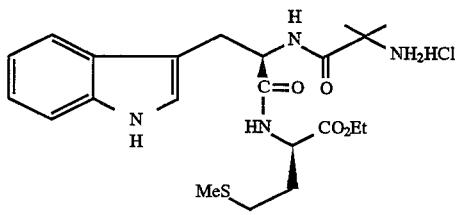

Prepared by the procedure described in Example 1, Step C from the intermediate from previous step (240 mg) and HCl gas in ethyl acetate (10 mL) at 0° C. Reaction time: 20 minutes. Product: 200 mg.

FAB-MS calc. for $C_{22}H_{32}N_4O_4S$: 448; found: 449 (M+H). $^1$HNMR (400 MHz, $CD_3OD$): 8.48, 8.00 (2d, 1H), 7.65 (d, J=7.8 Hz, 1H), 7.32 (d, J=8.0 Hz, 1H), 7.15 (s, 1H) 7.07 (t, 1H), 7.00 (t, 1H), 4.80–4.78 (m, 1H), 4.59–4.54 (m, 1 H), 4.15 (q, J=7.1 Hz, 2H), 3.34 (dd, J=5.4 Hz, 14.9 Hz, 1H), 3.15 (dd, J=9.5 Hz, 14.7 Hz, 1H), 2.59–2.44 (m, 2H), 2.14–2.08 (m, 1H), 2.06 (s, 3H), 2.02–1.94 (m, 3H), 1.54 (s, 3H), 1.31 (s, 3H), 1.25 (t, J=7.1 Hz, 3H).

EXAMPLE 7

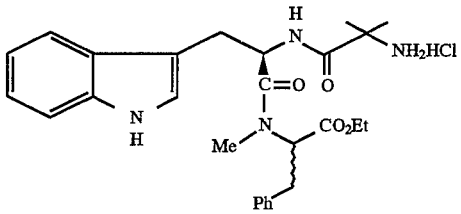

Step A:

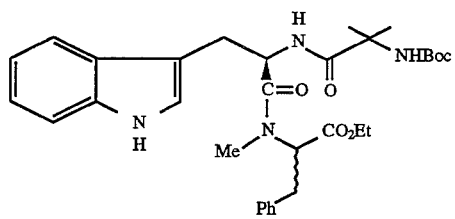

Prepared by the procedure described in Example 1, Step B from N-methyl-DL-phenylalanine ethyl ester hydrochloride (125 mg, 0.514 mmol), Intermediate 1 (200 mg, 0.514 mmol), HOBT (1 eq.), N-methyl morpholine(0.068 mL, 0.514 mmol), and EDC (200 mg, 1.03 mmol).

Product: 141 mg. FAB-MS calc. for $C_{32}H_{42}N_4O_6$: 578; found: 579 (M+H).

Step B:

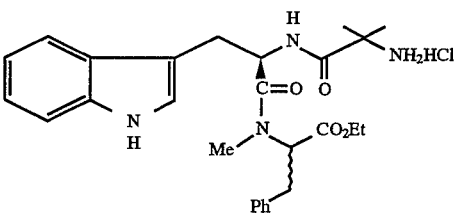

Prepared by the procedure described in Example 1, Step C. The intermediate from previous step (90 mg) and HCl gas in ethyl acetate (5 mL) at 0° C. Product: 78 mg.

FAB-MS calc. for $C_{27}H_{34}N_4O_4$: 478; found: 479 (M+H).

EXAMPLE 8

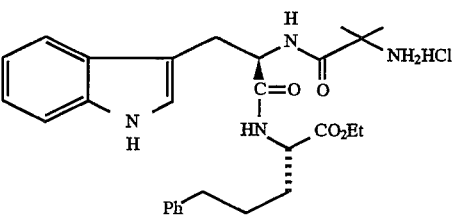

Step A:

-continued

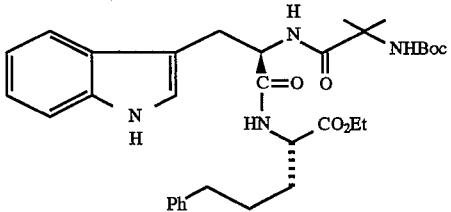

Prepared by the procedure described in Example 1, Step B from L-2-amino-5-phenylpentanoic acid ethyl ester hydrochloride (Chenault et al., *J. Am. Chem. Soc.*, 111, 6354–6364 (1989)) (200 mg, 0.776 mmol), Intermediate 1 (200 mg, 0.514 mmol), HOBT (1 eq.), N-methyl morpholine (0.068 mL, 0.514 mmol), and EDC (200 mg, 1.02 mmol).

Product: 265.4 mg. FAB-MS calc. for $C_{33}H_{44}N_4O_6$: 592; found: 593 (M+H).

Step B:

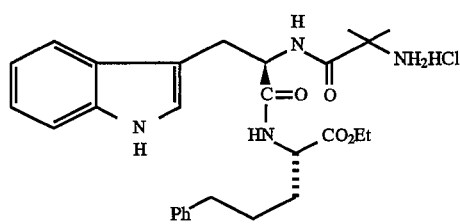

Prepared by the procedure described in Example 1, Step C from the intermediate from previous step (235 mg) and HCl gas in ethyl acetate (5 mL) at 0° C.

Product: 210 mg. FAB-MS calc. for $C_{28}H_{36}N_4O_4$: 492; found: 493 (M+H). $^1$HNMR (400 MHz, $CD_3OD$): 7.61 (d, J=8.7 Hz, 1H), 7.29–6.99 (m, 9H), 4.79 (t, J=7.5 Hz, 1H), 4.23 (dd, J=5 Hz, 8.3 Hz, 1H), 4.13–4.08 (m, 2 H), 3.27 (dd, J=7 Hz, 14 Hz, 1H), 3.12 (dd, J=8 Hz, 14 Hz, 1H), 2.51–2.46 (m, 2H), 1.63–1.54 (m, 1H), 1.54 (s, 3H), 1.50–1.40 (m, 1H), 1.37 (s, 3H), 1.40–1.20 (m, 2H), 1.20 (t, J=7.1 Hz, 3H).

EXAMPLE 9

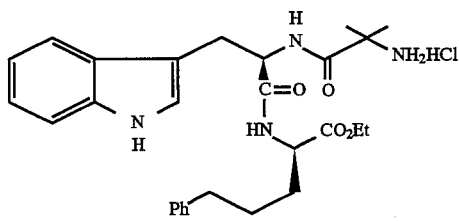

Step A:

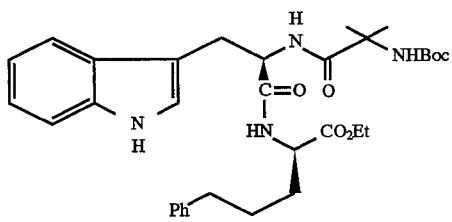

Prepared by the procedure described in Example 1, Step B from D-2-amino-5-phenylpentanoic acid ethyl ester hydrochloride (Chenault et al., *J. Am. Chem. Soc.*, 111, 6354–6364 (1989)) (200 mg, 0.776 mmol), Intermediate 1 (200 mg, 0.514 mmol), HOBT (1 eq.), N-methyl morpholine (0.068 mL, 0.514 mmol), and EDC (200 mg, 1.02 mmol).

Product: 260.0 mg. FAB-MS calc. for $C_{33}H_{44}N_4O_6$: 592; found: 593 (M+H).

Step B:

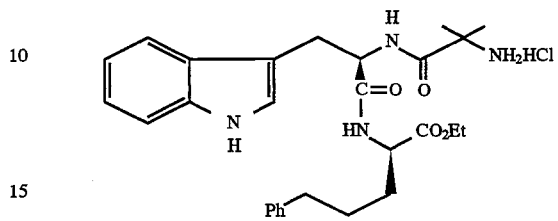

Prepared by the procedure described in Example 1, Step C. The intermediate from previous step (230 mg) and HCl gas in ethyl acetate (5 mL) at 0° C. Reaction time: 30 minutes.

Yield: 201 mg FAB-MS calc. for $C_{28}H_{36}N_4O_4$: 492; found: 493 (M+H). $^1$HNMR (400 MHz, $CD_3OD$): 7.65 (d, J=7.8 Hz, 1H), 7.32–6.98 (m, 9H), 4.84–4.80 (m, 1H), 4.39 (dd, J=5 Hz, 8 Hz, 1H), 4.13 (q, J=7.1 Hz, 2H), 3.33 (dd, J=5.4 Hz, 15 Hz, 1H), 3.12 (dd, J=9.6 Hz, 14.5 Hz, 1H), 2.70–2.60 (m, 2H), 1.90–1.80 (m, 1H), 1.75–1.60 (m, 3H), 1.50 (s, 3H), 1.27 (s, 3H), 1.23 (t, J=7.1 Hz, 3H).

EXAMPLE 10

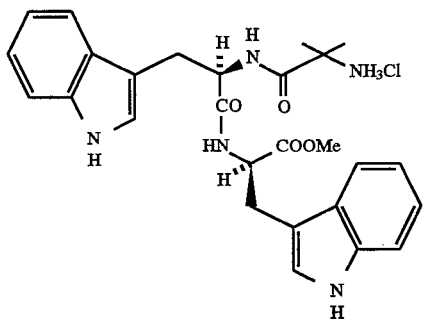

Step A:

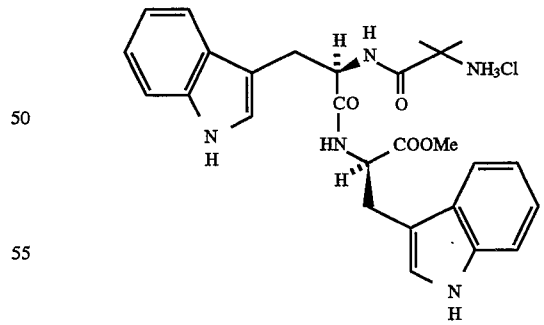

To a solution of 0.10 g of Intermediate 1 in 5 mL of $CH_2Cl_2$ was added 0.10 g of D-TRP methyl ester, 64 mg of HOBT, 0.052 mL of NMM, and 0.10 g of EDC and stirred at RT for 18 h. The reaction mixture was diluted with 10 mL of $CH_2Cl_2$ and washed with 0.10N HCl (10 mL), saturated $NaHCO_3$ (10 mL), dried over $MgSO_4$ and concentrated. Flash chromatography of the residue with $CH_2Cl_2$-acetone (1:1) as the eluent gave 0.134 g of the desired material.

To a solution of this above intermediate in 5 mL of ethyl acetate at 0° C was bubbled in HCl gas for 30 seconds. The flask was capped and stirred for 30 minutes. Ether was added and the precipitate was faltered under an $N_2$ atmosphere. This gave 89 mg of the title compound as a yellow solid.

$^1$H NMR (CD$_3$OD, 400 MHz) δ 7.60 (d, 1H), 7.42 (d, 1H), 7.33 (s, 1H), 7.30 (s, 1H), 6.97–7.10 (m, 6H), 4.78 (dd, 1H), 4.70 (dd, 1H), 3.68 (s, 3H), 3.30–3.10 (m, 4H), 1.40 (s, 3H), 1.28 (s, 3H).

EXAMPLE 10A

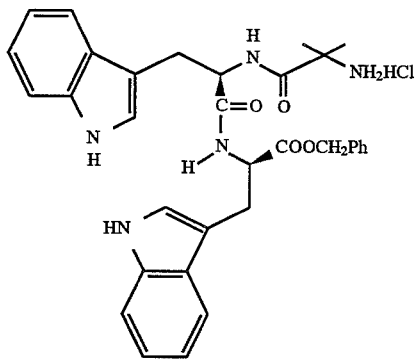

Step A:

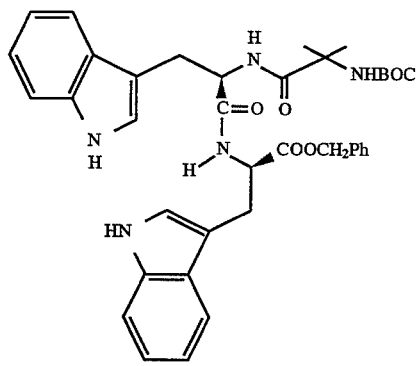

The above intermediate was synthesized as described in Example 10 but D-Tryptophan benzyl ester was used in place of the methyl ester.

Step B:

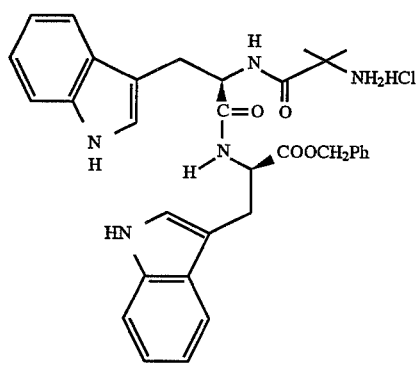

A solution of 0.075 g of the intermediate synthesized in Step A in ethyl acetate was treated with HCl (gas) at 0° C. for a few seconds. After 30 min. ether was added and the precipitate was filtered under a nitrogen atmosphere and dried to give 0.060 g of the title compound as a pale yellow solid.

$^1$H NMR (400 MHz; CD$_3$OD) 8.15, 7.83, 7.60, 7.47 (4 doublets, 2H), 7.38–6.90 (m, 13H), 5.00 (ABq, 2H), 4.80–4.65 (m, 2H), 3.30–3.06 (m, 4H), 1.40 (s, 3H), 1.22 (s, 3H).

EXAMPLE 10B

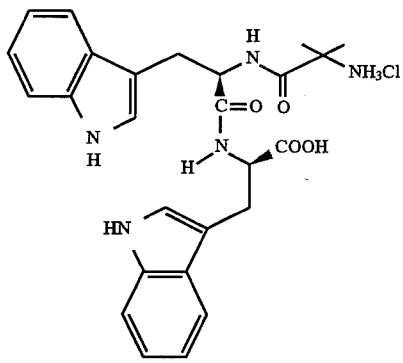

Step A:

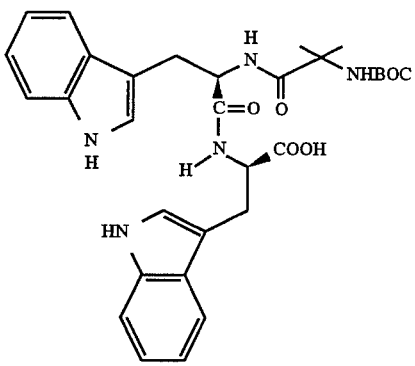

A solution of 0.70 g of the compound prepared in Step A of Example 10A was hydrogenated with 10% Pd/C in methanol for 3 h. The catalyst was filtered off through a pad of celite. The filtrate was concentrated to give the desired acid as a white foam.

Step B:

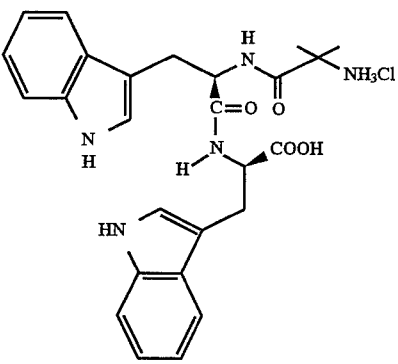

The intermediate prepared in Step A was deprotected with the HCl/EtOAc protocol as described above to give the title compound as an off-white solid.

$^1$H NMR (400 MHz; CD$_3$OD) 7.92, 7.74, 7.60, 7.30 (4 doublets, 2H), 7.30 (d, 2H), 7.16–6.90 (m, 8H), 4.81–4.65 (m, 2H), 3.34–3.06 (m, 4H), 1.38 (s, 3H), 1.22 (s, 3H).

EXAMPLE 10C

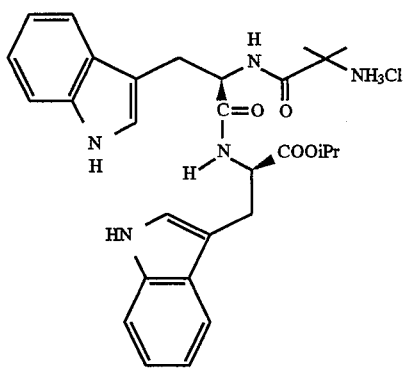

A solution of 0.10 g of the intermediate prepared in Step A of Example 10B in isopropanol was treated with HCl (gas) at 0° C. for 10 seconds. The reaction mixture was allowed to warm up to room temperature and stirred overnight. The solvent was removed under reduced pressure and the crude precipitate was washed with EtOAc-CH₂Cl₂-MeOH-ether (2:1:0.10:2) and the remaining solid was collected and dried to give the title compound.

$^1$H NMR (400 MHz; CD$_3$OD) 8.15, 7.80, 7.62, 7.45 (4 doublets, 2H), 7.30 (d, 2H), 7.16–6.95 (m, 8H), 4.90 (m, 1H), 4.80–4.60 (m, 2H), 3.30–3.06 (m, 4H), 1.40 (s, 3H), 1.25 (s, 3H), 1.20 and 1.05 (2 doublets, 6H).

EXAMPLE 10D

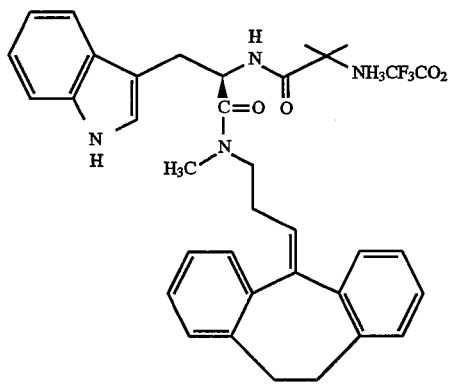

Step A:

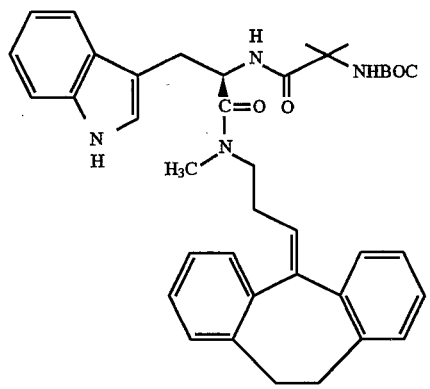

To a solution of 0.10 g of N-tBOC-D-Tryptophan in 10 mL of chloroform was added 0.090 g of the monomethylamine derivative of amitryptyline, 0.055 g of HOBT and 0.086 g of EDC and stirred at RT for 2 h. The reaction was diluted with 15 mL of ether and washed with water (5 mL), 10% aqueous citric acid (10 mL), and saturated aqueous NaHCO3 (5 mL), dried over anhrdrous MgSO4 and concentrated to provide a crude product that was used without purification.

A solution of crude product from above was treated with 3 mL of TFA and 4 drops of anisole for 1 h at RT. The reaction mixture was evaporated to dryness and azeotroped with toluene. The residue was dissolved in 5 mL of chloroform and reacted with 0.076 g of N-BOC-a-methylalanine in the presence of 0.055 g of HOBT, 0.15 mL of N-methylmorpholine, and 0.086 g of EDC for 2 h. The reaction mixture was worked-up as described above and the crude product was separated by flash chromatography (10 g silica gel; hexane-EtOAc (2:1) as eluent) gave 0.069 g of the desired product.

Step B:

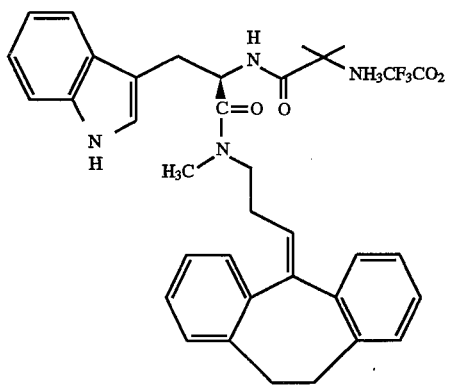

The compound prepared in Step A (0.069 g) was treated with 1.0 mL of TFA for 1 h. The reaction mixture was evaporated to dryness to give 0.052 g of the desired product after trituration with ether.

EXAMPLE 11

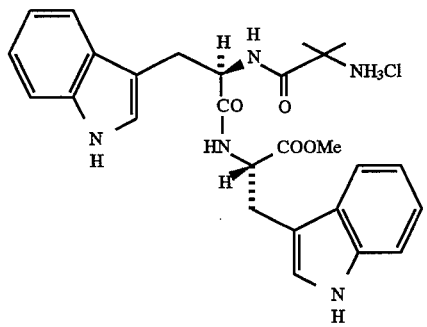

Step A:

-continued

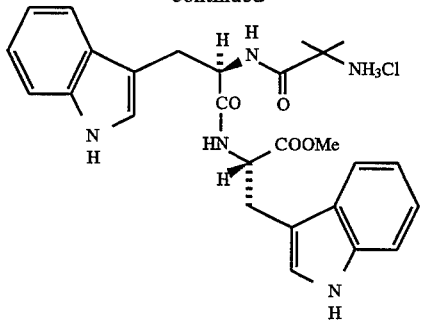

This compound was made in a similar manner to the compound reported in Example 10 but L-TRP methyl ester was used in place of D-TRP methyl ester.

¹H NMR (CD₃OD, 400 MHz) δ7.60 (d, 1H), 7.42 (d, 1H), 7.33 (s, 1H), 7.30 (s, 1H), 6.97–7.10 (m, 6H), 4.78 (dd, 1H), 4.70 (dd, 1H), 3.68 (s, 3H), 3.30–3.10 (m, 4H), 1.40 (s, 3H), 1.28 (s, 3H).

EXAMPLE 12

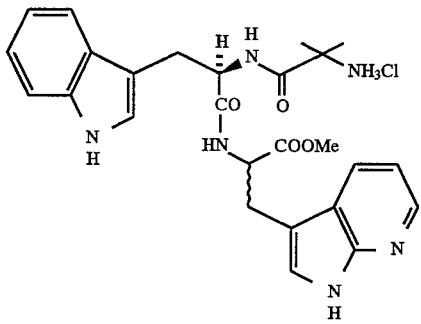

Step A:

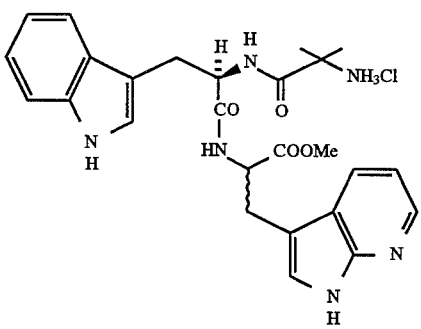

To 0.40 g of commercially available (DL)-7-aza-TRP in 10 mL of dry ethanol at 0° C. was bubbled in HCl gas for 15 seconds. The reaction mixture was heated to reflux for 18 h. The reaction mixture was neutralized with aqueous Na₂CO₃ solution, and extracted with CH₂Cl₂. The combined organic extracts were washed with brine, dried over K₂CO₃, and concentrated.

To 0.10 g of the above ethyl ester in 4 mL of CH₂Cl₂ was added 0.10 g of Intermediate 1, 0.069 g of HOBT, 0.12 g of EDC and stirred at RT for 2 days. The reaction mixture was poured in saturated aqueous NaHCO₃ solution and extracted with CH₂Cl₂. The combined organic extracts were washed with brine, dried over Na₂SO₄, filtered, and concentrated. Flash chromatography of the residue with CH₂Cl₂-acetone-ether (3:2:1) as the eluent gave 75 mg of the title compound.

To 75 mg of the above intermediate in 2 mL of ethyl acetate was bubbled in HCl gas for 15 seconds. The flask was capped and stirred for 30 minutes. Ether was added and the precipitate was filtered under an N₂ atmosphere to give the title compound as a yellow solid.

¹H NMR (CD₃OD, 400 MHz) δ8.75 (d, 1H), 8.40 (d, 1H), 7.70–7.55 (m, 3H), 7.30 (d, 1H), 7.15–6.93 (m, 3H), 4.80–4.66 (m, 2H), 4.10 (2q, 2H), 3.30–3.10 (m, 4H), 1.52 (s, 3H), 1.36 (s, 3H), 1.18 (2t, 3H).

EXAMPLE 13

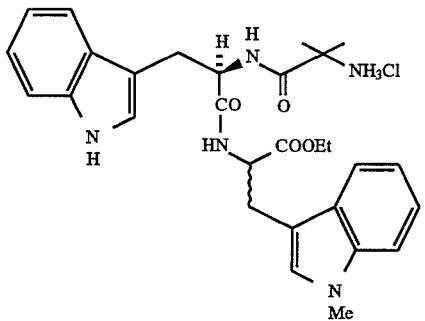

Step A:

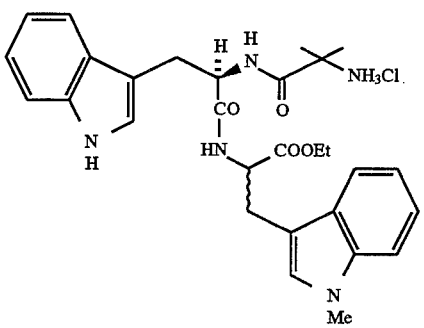

This compound was made as described in Step A of Example 11 but (DL)-1-methyl TRP was used in place of (DL)-7-aza TRP. The compound exists as a mixture of rotamers.

¹H NMR (CD₃OD, 400 MHz) δ8.10–8.00 (2d, 1H), 7.60 (d, 1H), 7.45 (d, 1H), 7.33 (d, 1H), 7.31 (d, 1H), 7.18–7.05 (m, 3H), 7.03–6.95 (m, 3H), 4.80–4.70 (m, 1H), 4.70–4.60 (m, 1H), 4.05 (2q, 2H), 3.70 (s, 3H), 3.28–3.00 (m, 4H), 1.44 (s, 3H), 1.26 (s, 3H), 1.13 (t, 3H).

EXAMPLE 14

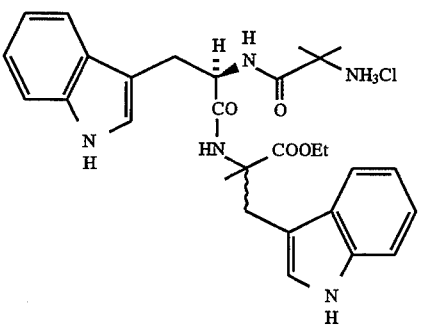

Step A:

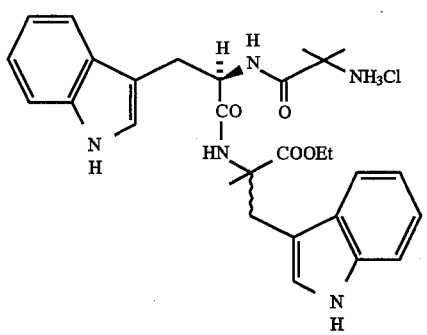

This compound was made as described in Step A of Example 11 but (DL)-α-methyl TRP was used in place of (DL)-7-aza TRP. The compound exists as a mixture of rotamers.

$^1$H NMR (CD$_3$OD, 400 MHz) δ8.05 (s, ½H), 7.98 (d, ½H), 7.90 (d, ½H), 7.85 (s, ½H), 7.63 (t, 1H), 7.48 (t, 1H), 7.33 (d, 2H), 7.13–6.98 (m, 4H), 4.82–4.70 (m, 1H), 4.10 (2q, 2H), 3.43–2.20 (m, 3H), 3.15–3.00 (m, 1H), 1.50 and 1.49 (2s, 6H), 1.41 (s, 1H), 1.30–1.14 (m, 5H).

EXAMPLE 15

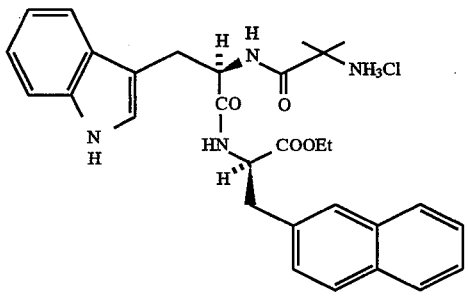

Step A:

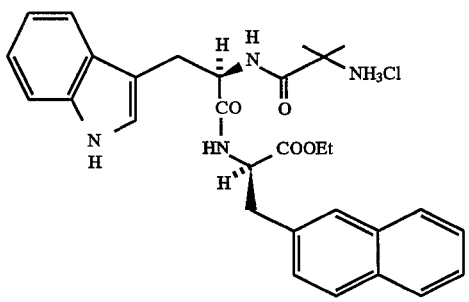

This compound was made as described in Step A of Example 11 but (D)-2-naphthyl alanine was used in place of (DL)-7-aza TRP.

The compound exists as a mixture of rotamers.

$^1$H NMR (CD$_3$OD, 400 MHz) δ8.33 (d, 1H), 7.80 7.75 (m, 3H), 7.66 (s, 1H), 7.60 (d, 1H), 7.48–7.39 (m, 2H), 7.35 (dd, 1H), 7.31 (d, 1H), 7.08 (t, 1H), 6.98 (t, 1H), 5.50 (s, 1H), 4.80–4.70 (m, 1H), 4.10 (q, 1H), 3.15–3.08 (m, 4H), 1.40 (s, 1H), 1.28 (s, 3H), 1.15 (t, 3H).

EXAMPLE 16

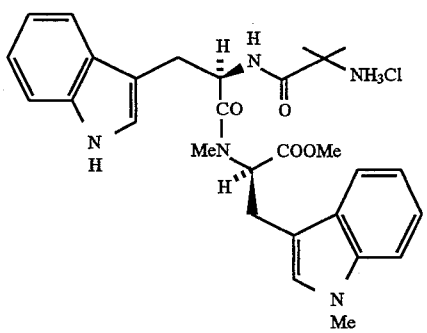

Step A:

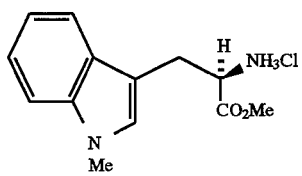

To a suspension of 0.55 g of 60% sodium hydride in mineral oil in 40 mL of dry DMF at 0° C. was added a solution of 1.0 g of N-t-BOC-D-TRP in 10 mL of DMF and stirred for 30 min. Methyl iodide (1 mL) was added and stirred at RT for 1 h. The reaction mixture was poured into ice-water and extracted with CHCl$_3$. The combined organic extracts were washed with brine, dried over Na$_2$SO$_4$, filtered and concentrated. This material was dissolved in 5 mL of methanol and 0.50 mL of concentrated HCl was added and heated at reflux for 24 h. The reaction mixture was concentrated. The residue was dissolved in CH$_2$Cl$_2$ and washed with aqueous NaHCO$_3$. The aqueous layers were back extracted with CH$_2$Cl$_2$. The combined organic extracts were washed with brine, dried over K$_2$CO$_3$, and concentrated.

$^1$H NMR (CDCl$_3$, 400 MHz) δ7.60 (d, 1H), 7.28 (d, 1H), 7.22 (t, 1H), 7.10 (t, 1H), 6.89 (s, 1H), 3.71 (s, 3H), 3.66 (s, 3H), 3.53 (t, 1H), 3.16 (dd, 1H), 3.09 (dd, 1H), 2.37 (s, 3H).

Step B:

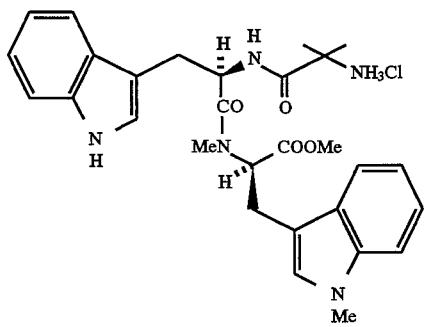

The above intermediate was transformed to the title compound as described in Step A of Example RN-3 but the intermediate from Step A was used in place of (DL)-7-aza TRP.

$^1$H NMR (CD$_3$OD, 400 MHz) δ7.58 (d, 1H), 7.35 (d, 1H), 7.32–7.25 (m, 2H), 7.15 (t, 1H), 7.10–6.95 (m, 4H), 6.88 (s, 1H), 5.34 (dd, 1H), 5.03 (t, 1H), 3.72 (s, 3H), 3.68 (s, 3H), 3.38 (dd, 1H), 3.22–3.10 (m, 2H), 2.96 (s, 3H), 2.58 (bd, 1H), 1.50 (s, 3H), 1.28 (s, 3H).

EXAMPLE 17

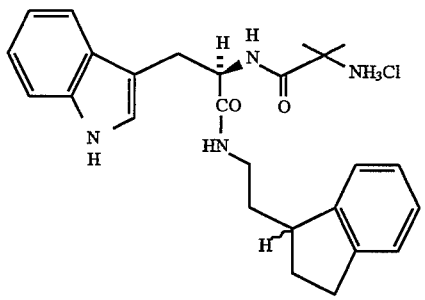

Step A:

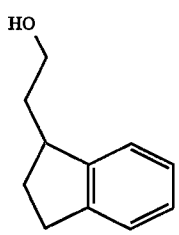

To 1.0 g of indene in 10 mL of dry THF at −78° C. was added 10.3 mL of 1.6M n-BuLi in hexane and stirred for 45 minutes. A solution of 2.50 g of 2-t-butyldimethylsilyloxy-1-bromoethane in 10 mL of THF was added and allowed to warm up to 0° C. and stir for 6 h. The reaction mixture was poured into 50 mL of water and extracted with ether (3×50 mL). The combined organic extracts were washed with brine, dried over $MgSO_4$, and concentrated to 8.6 g of a product. This material was stirred overnight in 50 mL of THF and 50 mL of 5% aqueous HCl. The reaction was extracted with ether (2×50 mL). The combined organic extracts were washed with brine (50 mL), dried over $MgSO_4$ and concentrated to yield 4.6 g of the crude product. Flash chromatography of this residue with hexane-ether (1:1) as eluent gave 4.6 g of product.

This material was dissolved in 25 mL of ethanol and 1.0 g of 10% Pd/C was added and hydrogenated for 3 h. The catalyst was filtered off through a pad of celite and washed with ether, and concentrated to give a colorless oil. This material was used without purification.

Step B:

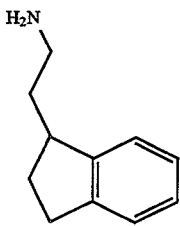

To 0.471 g of the above intermediate in 10 mL of THF at 0° C. was added 0.61 mL of triethylamine and 0.27 mL of mesyl chloride and stirred for 1 h. The reaction mixture was poured into 10 mL of saturated aqueous $NaHCO_3$ and extracted with ether (2×10 mL). The combined organic extracts were washed with brine (10 mL), dried over $MgSO_4$, and concentrated. To this crude product in 5 mL of DMSO was added 0.50 g of sodium azide and stirred at 60° C. overnight. The reaction mixture was poured into 15 mL of water and extracted with ether (2×15 mL). The combined organic extracts were washed with brine (10 mL), dried over $MgSO_4$, and concentrated to give a the azido-material as a brown oil.

Nickel/aluminum alloy was added to a solution of the above intermediate in 10 mL of ethanol and 10 mL of 20% aqueous NaOH solution and stirred at 60° C. for 1 h. The reaction mixture was cooled to RT, the solids were filtered and washed with $CHCl_3$. The filtrate was concentrated, and then diluted with 10 mL of brine, and extracted with $CHCl_3$ (2×10 mL). The combined organic extracts were washed with brine (10 mL), dried over $K_2CO_3$, and concentrated. This gave 0.150 g of the amine.

Step C:

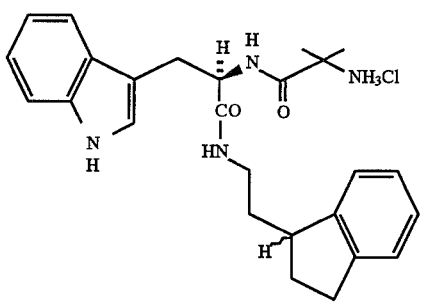

To a solution of 0.150 g of the amine intermediate from Step B in 10 mL of $CHCl_3$ was added 0.28 g of N-t-BOC-D-TRP, 0.142 g of HOBT, and 0.220 g of EDC and stirred at RT for 3 h. The reaction mixture was poured into 10 mL of water and extracted with ether (2×15 mL). The combined organic extracts were extracted with 20% aqueous citric acid (10 mL), saturated $NaHCO_3$ (10 mL), dried over $MgSO_4$, and concentrated. The residue was treated with 3 mL of $CH_2Cl_2$, 3 mL of TFA, and 0.10 mL of anisole for 1 h. The reaction mixture was evaporated to dryness and the residue was azeotroped with toluene, dried under vacuum, and used without purification. To a solution of this material in 10 mL of $CHCl_3$ was added 0.70 mL of NMM, 0.142 g of HOBT, 0.212 g of N-t-BOC-α-methylalanine, and stirred at RT for 3 h. The reaction was worked-up as described above. Flash chromatography of the residue with hexane-ethyl acetate (1:1) as the eluent gave 86 mg of the desired product.

Deprotection of the intermediate with TFA (2 mL), in $CH_2Cl_2$ (2 mL), with 0.020 mL of anisole, gave the title compound as a solid. This material is a mixture of diastereomers.

$^1$H NMR ($CD_3OD$, 400 MHz) δ7.60 (d, 1H), 7.55–7.50 (m, 1H), 7.29 (dd, 1H), 7.18–6.95 (m, 6H), 4.60 (t, 1H), 3.30–3.10 (m, 4H), 2.95–2.70 (m, 3H), 2.20 (q, 1H), 1.81 (q, 1H), 1.66–1.53 (m, 1H), 1.50 (s, 3H), 1.42–1.30 (m, 1H), 1.33 (s, 3H).

EXAMPLE 18

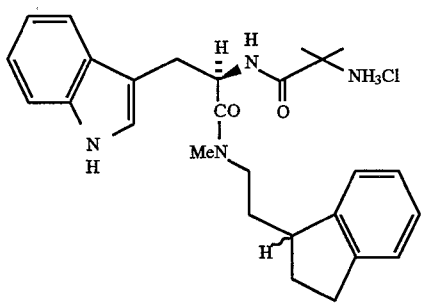

Step A:

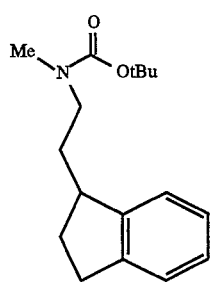

To 80 mg of the amine intermediate prepared in Step B of Example 17 in 5 mL of CH₂Cl₂ and 0.10 mL of triethylamine was added 0.104 g of di-t-butyl dicarbonate and stirred for 2 h. The reaction mixture poured into 5 mL of 20% aqueous citric acid and extracted with ether (2×10 mL). The combined organic extracts were washed with saturated aqueous NaHCO₃, brine (10 mL), dried over MgSO₄, and concentrated. This gave 0.123 g of the desired product.

To a solution of the above intermediate in 5 mL of THF was added 1.50 mL of 1M solution of sodium bis(trimethylsilyl)amide in THF at 0° C., and stirred for 30 minutes. Methyl iodide (0.10 mL) was added and stirred at RT overnight. The reaction mixture was poured into water (10 mL), and extracted with ether (3×10 mL). The combined organic extracts were washed with brine (10 mL), dried over MgSO₄, and concentrated to give 0.108 g of the methylated product.

¹H NMR (CDCl₃, 400 MHz) δ7.30–7.05 (m, 4H), 3.45–3.20 (m, 2H), 3.20–3.00 (m, 1H), 3.00–2.75 (m, 1H), 2.88 (s, 1H), 2.33 (q, 1H), 2.10 (q, 1H), 1.80–1.55 (m, 2H), 1.48 (s, 9H), 1.50–1.35 (m, 1H).

Step B:

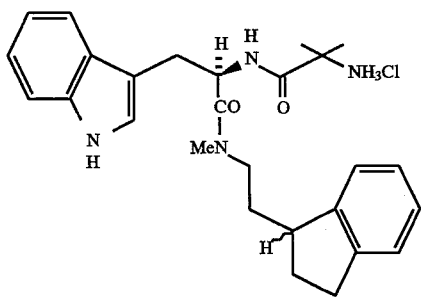

The intermediate was deprotected with TFA and then transformed to the title compound as described in Step C of Example 17. This compound is a mixture of diastereomers.

¹H NMR (CD₃OD, 400 MHz) δ7.65–7.50 (m, 1H), 7.40–7.20 (m, 1H), 7.20–6.5 (m, 7H), 5.20–5.05 (m, 1H), 3.40–3.00 (m, 4H), 3.00–2.60 (m, 5H), 2.25 (q, ½H), 2.10–1.95 (m, ½H), 1.90–1.78 (m, 1H), 1.75–1.30 (m, 10H).

EXAMPLE 19

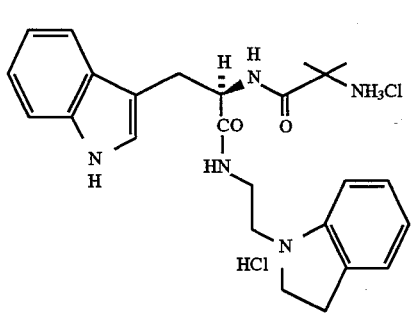

Step A:

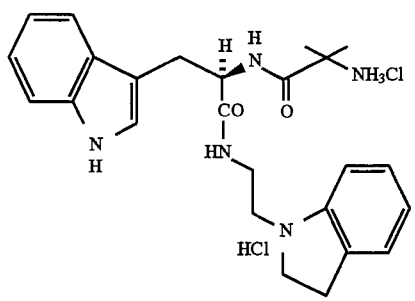

The indoline ethanol was convened to the indoline ethyl amine as described in Step B of Example 17. The amine derivative thereby synthesized was converted to the title compound as described in Step C of Example 17 with one minor modification. The final deprotection was carried out in methanol with concentrated HCl to give the dihydrochloride salt.

¹H NMR (CD₃OD, 400 MHz) δ8.20 (d, 1H), 7.60 (d, 1H), 7.55–7.40 (m, 4H), 7.28 (d, 1H), 7.17 (s, 1H), 7.00–6.90 (m, 2H), 4.70–4.60 (m, 1H), 3.95–3.85 (m, 1H), 3.82–3.70 (m, 1H), 3.60–3.45 (m, 2H), 4.40–3.15 (m, 4H), 1.60 (m, 3H), 1.36 (m, 3H).

EXAMPLE 20

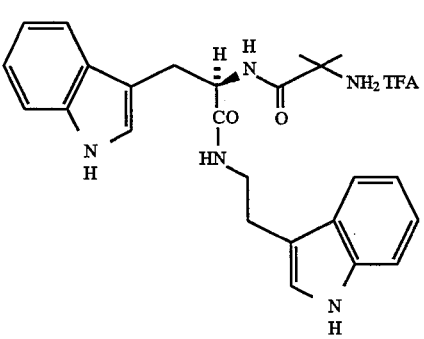

Step A:

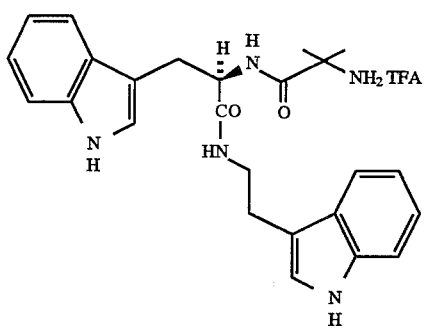

The title compound was prepared from commercially available N-t-BOC-D-tryptophan and tryptamine as described in Step C of Example 17. The title compound was isolated as a free base after NaHCO₃ work-up of the final trifluoroacetic acid salt.

¹H NMR (CD$_3$OD, 400 MHz) δ7.60 (d, 1H), 7.40 (d, 1H), 7.32 (d, 1H), 7.27 (d, 1H), 7.10–6.90 (m, 6H), 4.52 (t, 1H), 3.50–3.30 (m, 2H), 3.18 (t, 2H), 2.70 (t, 3H), 1.13 (s, 6H).

EXAMPLE 21

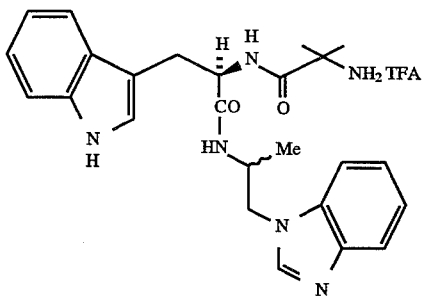

Step A:

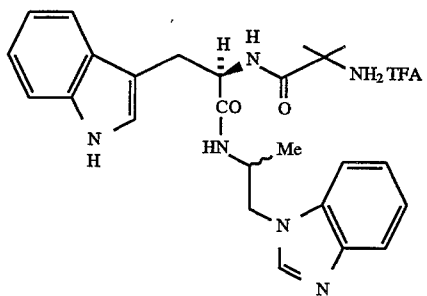

The title compound was synthesized from 1-(benzimidazolyl)-2-propylamine and N-t-BOC-D-TRP as described in Step C, Example 17. This compound is a mixture of diastereomers.

¹H NMR (CD$_3$OD, 400 MHz) δ7.60–9.22 and 9.15 (2s, 1H), 8.30 and 8.10 (2d, 1H), 8.00–7.80 (m, 2H), 7.70–7.60 (m, 2H), 7.50 (dd, 1H), 7.31 (t, 1H), 7.15–6.93 (m, 4H), 4.60–4.10 (m, 3H), 3.10 (d, 1H), 2.88 (d, 1H), 2.83–2.67 (m, 1H), 1.55 (s, 3H), 1.48 (s, 3H), 1.30 and 0.75 (2d, 3H).

EXAMPLE 22

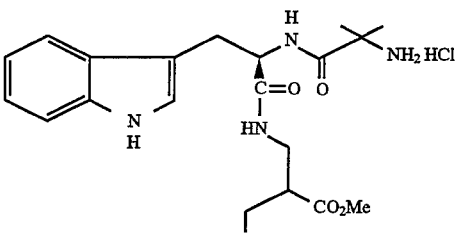

Step A:

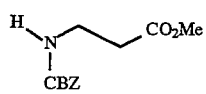

N-CBZ-β-alanine methyl ester

Prepared by the procedure described in Example 1, Step A from N-CBZ-β-alanine (5 g, 22.4 mmole), methanol and thionyl chloride to give the title compound.

Step B:

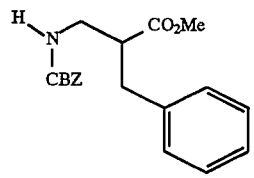

To a stirred solution of the intermediate (330 mg) from the previous step in THF (3 mL) was added potassium bis (trimethylsilyl)amide (3 mL, 0.5M in toluene) at –78° C. followed by the addition of hexamethylphosphoramide (5 mL). This mixture was warmed to room temperature to give a clear solution and then re-cooled to –78° C. To this solution was added another portion of potassium bis (trimethylsilyl)amide (3 mL, 0.5N in toluene). After 1 hour at –78° C., benzyl bromide (193 µL) was added to reaction mixture. The solution was stirred at –78° C. for 3 hours and poured into 0.5N HCl, extracted with ether three times. The combined organic layers were washed with water (five times), brine, dried over magnesium sulfate, and concentrated. The residue was purified by Pre-TLC (hexanes/ethyl acetate=4/1) to give the desired compound (164 mg, 35% yield).

Step C:

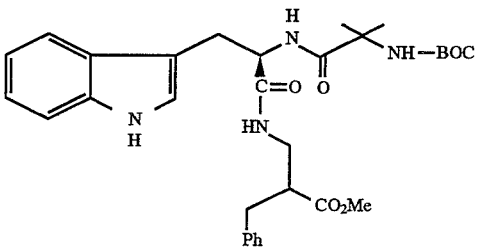

To a solution of the intermediate (154 mg) obtained from the previous step in methanol was added Pd(OH)$_2$ and hydrogenated under H$_2$ balloon for ½ hour. The mixture was filtered through Celite. The filtrate was concentrated. The residue was coupled to the Intermediate 1 by the procedure described in Example 1, Step B (without NMM) to give desired compound (240 mg, 87%).

Step D:

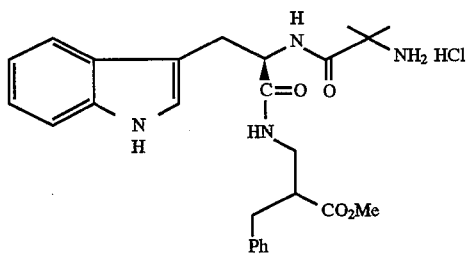

Prepared from the intermediate obtained from the previous step (31 mg) HCl gas in ethyl acetate at 0° C. by the procedure described in Example 1, Step C to give the title compound (27 mg).

$^1$H NMR (400 MHz, CD$_3$OD, mixture of two diastereomers): 7.61 (m, 1H), 7.32–6.99 (m, 9H), 4,70 (m, 1H), 3.56 (s, 3/2H), 3.54 (s, 3/2H), 3.37 (m, 1H), 3.26 (m, 2H), 3.10 (m, 1H), 2.74 (m, 3H), 1.54 (s, 3H), 1.34 (s, 3/2H), 1.32 (s, 3/2H).

EXAMPLE 23

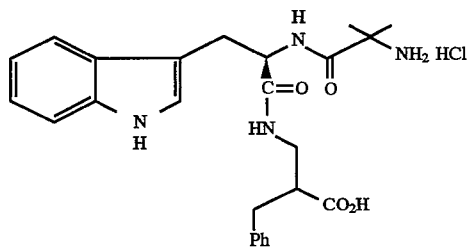

Step A:

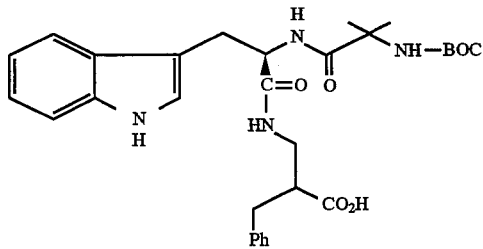

To a stirred solution of the intermediate from Example 22, Step C (66 mg) in 1 mL of methanol was added lithium hydroxide (25 mg) in 1 mL of water. The reaction was stirred at room temperature for 16 hours and evaporated in vacuo. The residue was diluted with water and acidified with 1N hydrochloric acid and then exacted with ether. The organic layer was dried over sodium sulfate, filtered and concentrated to give the desired compound (44 mg).

Step B:

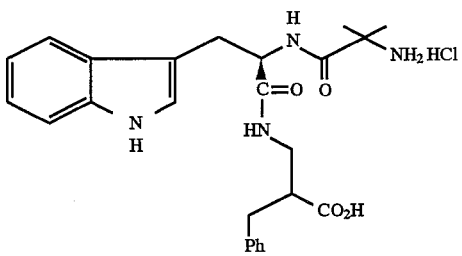

Prepared from the intermediate obtained from the previous step (7 mg) and HCl gas in ethyl acetate at 0° C. by the procedure described in Example 1, Step C to give the desired compound (5 mg).

$^1$H NMR (400 MHz, CD$_3$OD, mixture of two diastereomers): 7.62 (d, 8 Hz, 1H), 7.31–6.99 (m, 9H), 4.71 (m, 1H), 3.37 (m, 1H), 3.28 (m, 2H), 3.12 (m, 1H), 2.77 (m, 3H), 1.53 (s, 3H), 1.30 (s, 3H). FAB-MS: 451.2 (M+1).

EXAMPLE 24

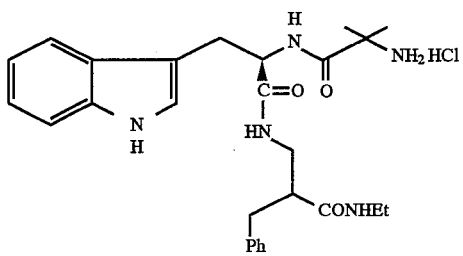

Step A:

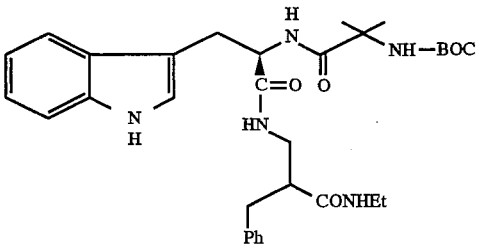

Prepared from the intermediate from Example 23, Step A (37 mg) and ethylamine hydrochloride (16 mg) by the procedure described in Example 1, Step C using triethylamine instead of NMM to give the coupling product.

Step B:

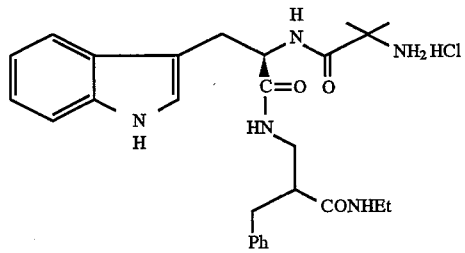

Prepared from the intermediate from the previous step and HCl gas at 0° C. by the procedure described in Example 1, Step C to give the desired compound (24 mg).

¹H NMR (400 MHz, CD₃OD, mixture of two diastereomers): 7.62 (d, 8 Hz, 1H), 7.31–6.99 (m, 9H), 4.68 (m, 1H), 3.37–3.23 (m, 3H), 3.15–2.91 (m, 3H), 2.65 (m, 3H), 1.55 (s, 3H), 1.32 (s, 3H), 0.90 (m, 3H). FAB-MS: 478.3 (M+1).

EXAMPLE 25

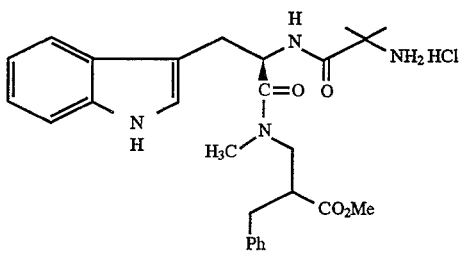

Step A:

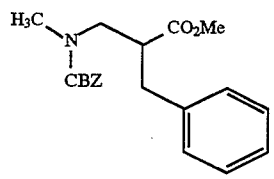

To a solution of the intermediate obtained from Example 22, Step A (1.15 g) in 10 mL of THF was added potassium bis(trimethylsilyl)amide (10.7 mL, 0.5N in toluene) at –78° C. and then warmed to room temperature. To this reaction mixture was added hexamethylphosphoramide (10 mL) to give a clear solution and then re-cooled to –78° C. This solution was added another portion of potassium bis(trimethylsilyl)amide (10.7 mL, 0.5N in toluene). After 1 hour at –78° C., benzyl bromide (577 μL) was added to reaction mixture. The solution was stirred at –78° C. for 4 hours and quenched with 1 mL of methyl iodide. The mixture was poured into 1N HCl, extracted with ether three times. The combined organic layers were washed with water (five times), brine, dried over magnesium sulfate, and concentrated. The residue was purified on silica gel to give the desired compound (1.43 g, 90%).

Step B:

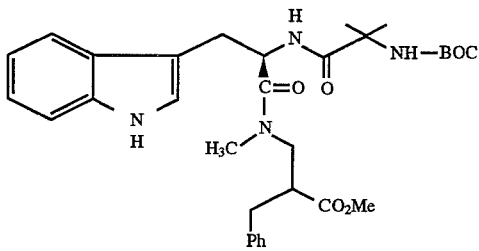

Prepared from the intermediate from the previous step (757 mg) by the procedure described in Example 22, Step C to give the coupling product (806 mg, 60%).

Step C:

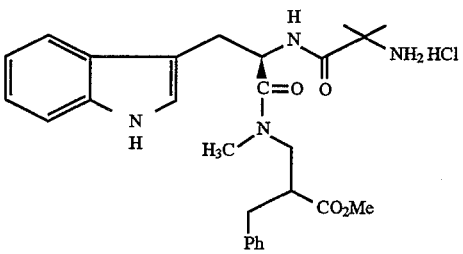

Prepared from the intermediate from the previous step (30 mg) by the procedure described in Example 1, Step C to give the desired compound 24 mg.

¹H NMR (400 MHz, CD₃OD, mixture of two diastereomers): 7.56 (m, 1H), 7.32–6.89 (m, 9H), 5.12 (m, 1H), 3.53 (s, 3/2H), 3.48 (s, 3/2H), 3.42 (m, 1H), 3.18 (m, 2H), 2.99 (m, 1H), 2.85 (s, 3H), 2.70 (m, 3H), 1.55 (s, 3H), 1.45 (s, 3/2H), 1.42 (s, 3/2H). FAB-MS: 479.3 (M+1).

EXAMPLE 26

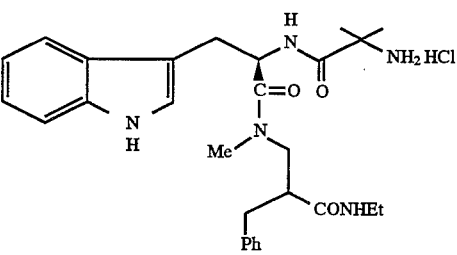

Step A:

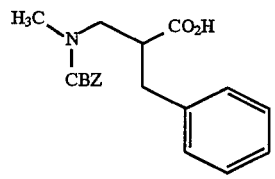

To a solution of the intermediate obtained from Example 25, Step A (304 mg) in 2 ml of methanol was added 2 ml 6N sodium hydroxide. The reaction was stirred at room temperature for 2 hours. This basic mixture was washed with ether three times. The ether layer was then washed with 1N sodium hydroxide three times. The combined basic aqueous layers were cooled to 0° C. and acidified with conc. HCl until a precipitate formed. Litmus paper trims blue to red. This solution was extracted with ethyl acetate three times. The combined organic layers were dried over sodium sulfate, faltered and concentrated to give the desired compound (225 mg, 75%).

Step B:

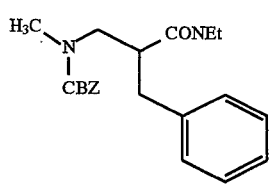

Prepared from the intermediate from the previous step (32 mg) and ethyl amine hydrochloride by the procedure described in Example 1, Step B using triethyl amine instead of NMM to give the coupling product (24 mg, 67%).

Step C:

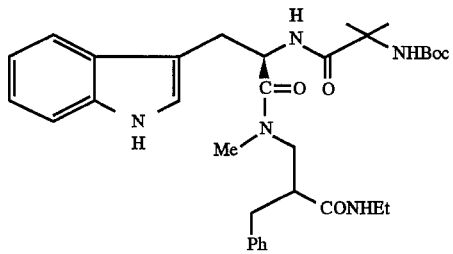

Prepared from the intermediate from the previous step (24 mg) by the procedure described in Example 22, Step C to give the coupling product. The residue was purified (chromatatron, methylene chloride/methanol=20/1) to give the desired compound (17 mg, 48%). Diastereomers separated during purification where applicable.

Step D:

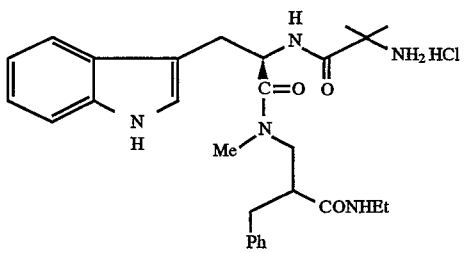

Prepared from the intermediate from the previous step (17 mg) and HCl gas in ethyl acetate at 0° C. by the procedure described in Example 1, Step C to give the desired compound (15 mg). FAB-MS: 492.0 (M+1).

TABLE III

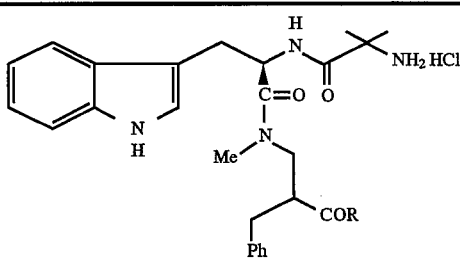

| | R | | FAB-MS (M + 1) |
|---|---|---|---|
| 1 | d1 + d2 | morpholine | 534.1 |
| 2 | d1 | N-methyl piperazine | 547.3 |
| 3 | d2 | N-methyl piperazine | 547.3 |
| 4 | d1 + d2 | dimethyl amine | 492.1 |

The additional final products shown in table were prepared to the above established procedure (with different amines) as exemplified in Example 26.

EXAMPLE 27

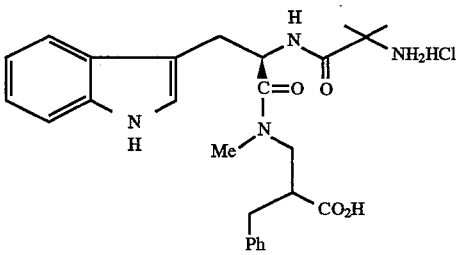

Step A:

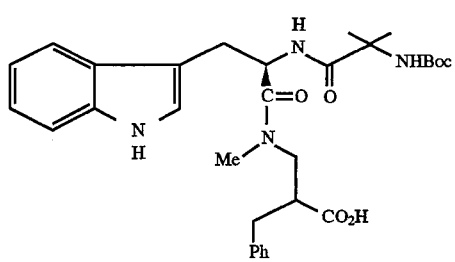

To a stirred solution of the intermediate from Example 25, Step B (110 mg) in 5 mL of methanol was added 5 mL of 6N sodium hydroxide. This reaction was stirred at room temperature for 16 hours and evaporated in vacuo. The residue was diluted with water and acidified with 1N hydrochloric acid and then extracted with ethyl acetate. The organic layer was dried over sodium sulfate, filtered and concentrated to give the desired compound (64 mg, 60%).

Step B:

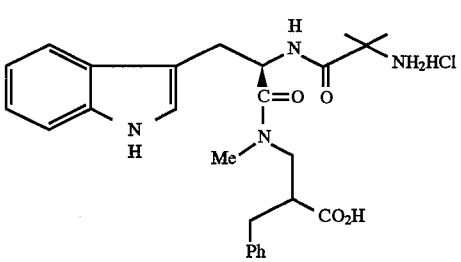

Prepared from the intermediate obtained from the previous step (20 mg) and HCl gas in ethyl acetate at 0° C. by the procedure described in Example 1, Step C to give the desired compound (13 mg). FAB-MS: 465.0 (M+1).

EXAMPLE 28

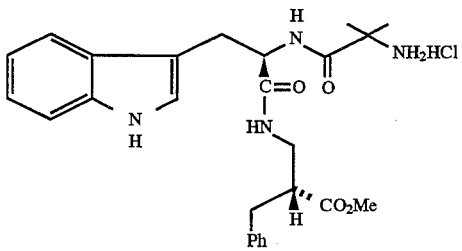

Step A:

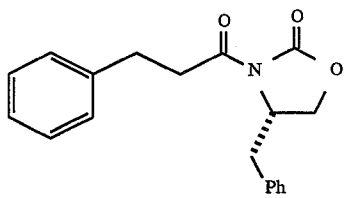

To a solution of (4S)-benzyl oxazolidinone (1.77 g) in THF (40 ml) was added n-butyllithium (1.6M, 8 ml) at −78° C. After 30 minutes, to the reaction mixture was added hydrocinnamoyl chloride (1 eq) and the mixture was warmed to room temperature for 5 minutes. The mixture was poured into water and extracted with ether. The organic layer was washed with brine, dried over MgSO$_4$, and concentrated. The residue was purified by chromatatron (hexanes/ethyl acetate=5/1) to give the desired product 2.06 g.

Step B:

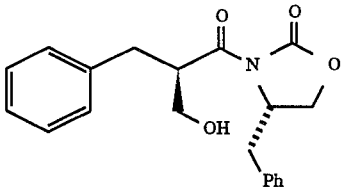

A solution of the intermediate (1.24 g) obtained from Step A in methylene chloride (20 ml) was cooled to 0° C. and treated dropwise with TiCl$_4$ (0.46 ml). After 5 minutes, diisopropylethylamine (0.74 ml) was added slowly and the resultant deep red solution was stirred at 0° C. for 1 hour. To this deep red solution was added trioxane (400 mg) in methylene chloride (4 ml) and the resulting mixture was stirred for additional 5 minutes. Then, another portion of TiCl$_4$ (0.46 ml) was added. After stirring 2.5 hour at 0° C., this clear solution was quenched with saturated aqueous ammonium chloride. This mixture was extracted with methylene chloride, washed with sodium bicarbonate, brine and dried over sodium sulfate. Concentration and purification (hexanes/ethyl acetate=4/1) gave the desired product 0.79 g.

Step C:

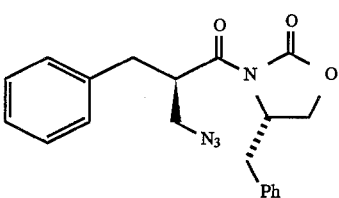

To a solution of the intermediate (0.7 g) obtained from Step B in THF (20 ml) was added triphenylphosphine (0.595 g) and diethylazodicarboxylate (0.357 ml) and then added diphenylphosphorylazide (0.488 ml) was added slowly. After stirring for 60 hours, the mixture was concentrated. The resulting residue was filtered through a plug of silica gel (100% ether) and concentrated. The material was purified by chromatatron (hexanes/ethyl acetate=10/1) to give the desired product (189 mg) and unreacted starting material (463 mg).

$^1$H NMR (400 MHz, CDCl$_3$): 7.21 (m, 10H), 4.50 (m, 1H), 4.35 (m, 1H), 4.06 (dd, 9 Hz, 3 Hz, 1H), 3.92 (t, 8 Hz, 1H), 3.68 (dd, 12 Hz, 8 Hz, 1H), 3.42 (dd, 12 Hz, 5 Hz, 1H), 3.22 (dd, 13 Hz, 3 Hz, 1H), 2.95 (dd, 13 Hz, 7 Hz, 1H), 2.78 (t, 9 Hz, 1H), 2.74 (t, 9 Hz, 1H). FAB-MS: 365.2 (M+1).

Step D:

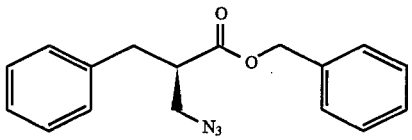

To a solution of benzyl alcohol (0.16 ml) in THF (5 ml) was added n-butyllithium (0.65 ml, 1.6M) at 0° C. After stirring 10 minutes, the intermediate (189 mg) obtained from Step C in THF (2 ml) was added to the reaction mixture. The resulting solution was stirred for an hour at 0° C. and quenched with 1N HCl. The mixture was extracted with ether, washed with brine and dried over MgSO$_4$. Concentration and purification (PLC, hexanes/ethyl acetate=20/1) to give the desired product (87 mg).

Step E:

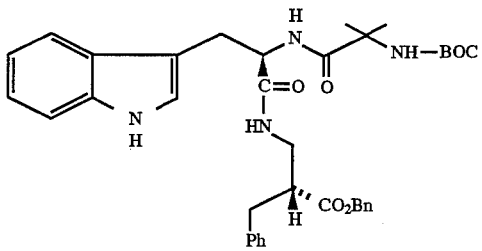

To a solution of the intermediate (87 mg) obtained from Step D in methanol was added Raney nickel and under 1 atmosphere of hydrogen for 2 hours. The mixture was filtered through Celite and the filtrate was concentrated. The residue was coupled to the Intermediate 1 by the procedure described in Example 1, Step B (without NMM) to give desired compound (101 mg).

Step F:

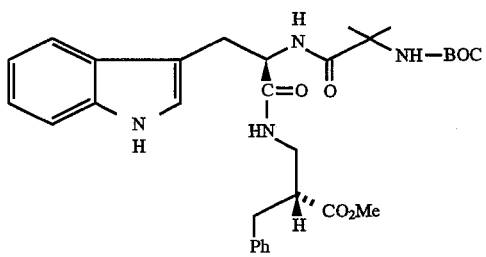

To a solution of the intermediate (101 mg) obtained from Step E in methanol was added Pd(OH)$_2$ and hydrogenated under hydrogen (1 atmosphere) for an hour. The mixture was filtered through Celite. The filtrate was concentrated to give corresponding acid (88 mg). The acid (17 mg) in ether was added diazomethane (prepared from N-methyl N-nitroso urea) at 0° C. until the solution turned yellow. The yellowish solution was stirred for a couple of hours at room temperature and concentrated. The residue was purified by PLC (hexanes/ethyl acetate=½) to give the desired product (11 mg).

Step G:

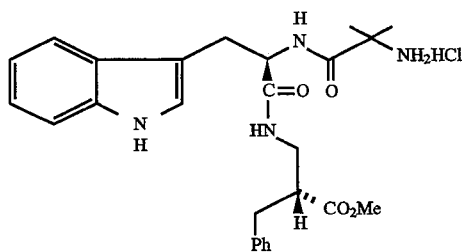

Prepared from the intermediate obtained from Step F and HCl gas in ethyl acetate at 0° C. by the procedure described in Example 1, Step C to give the desired compound (9 mg).

$^1$H NMR (400 MHz, CD3OD): 7.62 (d, 8 Hz, 1H), 7.31 (d, 8 Hz, 1H), 7.26–7.06 (m, 7H), 7.01 (t, 7 Hz), 4.70 (dd, 9 Hz, 2 Hz, 1H), 3.56 (s, 3H), 3.39–3.24 (m, 3H), 3.10 (dd, 14 Hz, 9 Hz, 1H), 2.85 (m, 1H), 2.74 (m, 2H), 1.54 (s, 3H), 1.32 (s, 3H). FAB-MS: 465.1 (M+1).

EXAMPLE 29

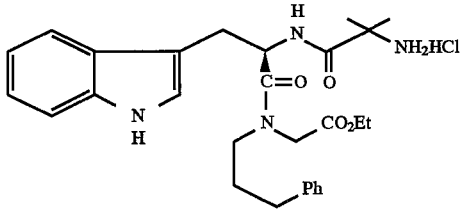

Step A: N-(3-phenyl-1-propyl)glycine ethyl ester

To a stirred solution of 3-phenyl-1-propylamine (5 mL, 35.2 mmol) in THF (20 mL), was added ethyl bromoacetate (3.9 mL, 35.2 mmol) and diisopropyl ethyl amine (6.13 mL). The reaction was stirred at room temperature overnight. The solid formed was filtered off and the solution was evaporated and purified by flash column to yield the desired material (2 g).

$^1$H NMR (400 MHz, CD3OD): δ(ppM) 7.28–7.13 (m, 5H), 4.13 (q, J=7.2 Hz, 3H), 3.37 (s, 2H), 2.68–2.60 (m, 4H), 1.88–1.76 (m, 2H), 1.25 (t, J=7.2 Hz, 3H).

Step B:

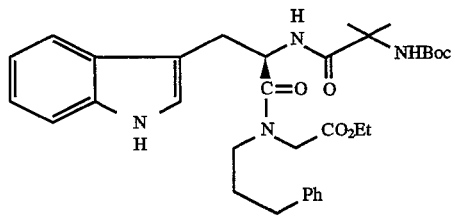

Prepared by the procedure described in Example 1, Step B from the intermediate from the previous step (170 mg), Intermediate 1 (200 mg, 0.514 mmol), HOBT (68 mg), and EDC (200 mg). Product: 254.8 mg. FAB-MS calc. for C$_{33}$H$_{44}$N$_4$O$_6$: 592; found: 593 (M+H).

Step C:

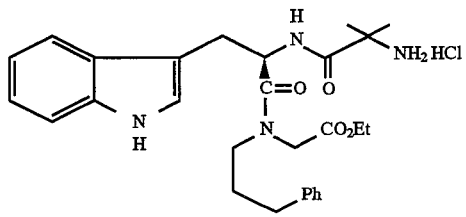

Prepared by the procedure described in Example 1, Step C from the intermediate from previous step (228.8 mg) and HCl gas in ethyl acetate (3 mL) at 0° C. Reaction time: 30 minutes. Product: 210 mg. FAB-MS calc. for C$_{28}$H$_{36}$N$_4$O$_4$: 492; found: 493 (M+H).

EXAMPLE 30

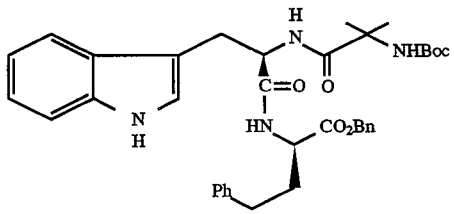

Step A:

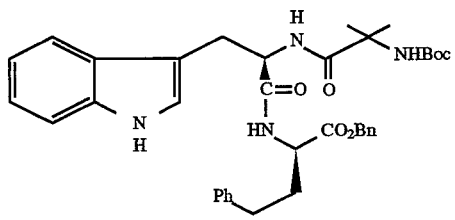

Prepared by the procedure described in Example 1, Step B from D-HomoPhe benzyl ester (1.38 g, 5.13 mmol), Intermediate 1 (2 g, 5.13 mmol), HOBT (694 mg), and EDC (1.53 g). Product: 2.90 g, (88%).

FAB-MS calc. for $C_{37}H_{44}N_4O_6$: 640; found: 641 (M+H).

Step B:

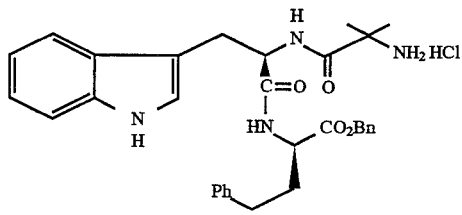

Prepared by the procedure described in Example 1, Step C from the intermediate from previous step (106 mg) and HCl gas in ethyl acetate (3 mL) at 0° C. Reaction time: 1 hour. Product: 94.5 mg. FAB-MS calc. for $C_{32}H_{36}N_4O_4$: 540; found: 541 (M+H).

EXAMPLE 31

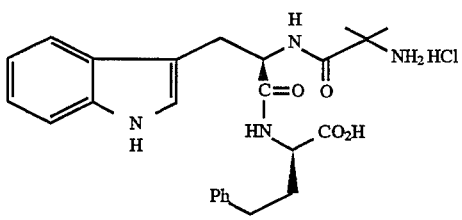

Step A:

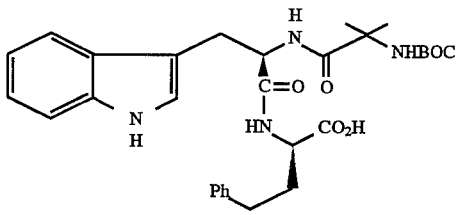

A solution of the material from Step A (2.74 g) of the previous example in 20 mL of ethanol was stirred at RT under a $H_2$ balloon for 20 minutes in the presence of 10% palladium on carbon (150 mg). The catalyst was filtered off through a pad of celite and washed with ethyl acetate. The filtrate was concentrated to give the acid as a foam (2.19 g, 93%).

FAB-MS calc. for $C_{30}H_{38}N_4O_6$: 550; Found 551 (M+H).

Step B:

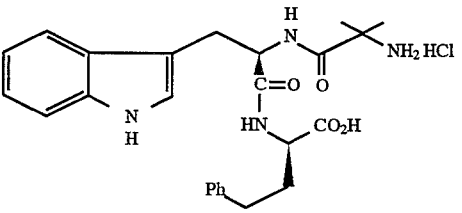

Prepared by the procedure described in Example 1, Step C from the intermediate from previous step (150 mg) and HCl gas in ethyl acetate (3 mL) at 0° C. Reaction time: 15 minutes. Product: 128 mg (96.5%).

FAB-MS calc. for $C_{25}H_{30}N_4O_4$: 450; Found 451 (M+H).

$^1$H NMR (400 MHz, CD3OD): δ(ppM) 8.50 (d, J=8 Hz, 1H), 7.69 (d, J=8 Hz, 1H), 7.31–7.00 (m, 8H), 4.89–4.85 (m, 1H), 4.39–4.35 (m, 1H), 3.38 (dd, J=4, 14 Hz, 1H), 3.16 (dd, J=10, 14 Hz, 1H), 2.72–2.64 (m, 2H), 2.21–2.12 (m, 1H), 2.08–1.98 (m, 1H), 1.53 (s, 3H), 1.27 (s, 3H).

EXAMPLE 32

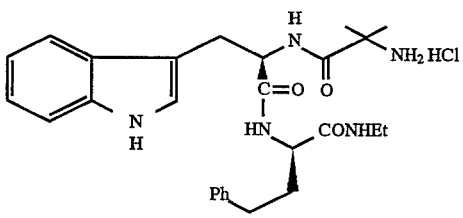

Step A:

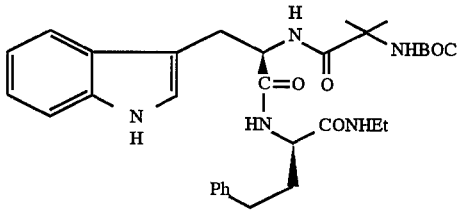

Prepared by the procedure described in Example 1, Step B from the intermediate from Step A of the previous example (150 mg, 0.272 mmol), ethyl amine hydrochloride (25 mg, 0.544 mmol), HOBT (37 mg), N-methyl morpholine (0.06 mL; 0.544 mmol), and EDC (100 mg). Product: 139 mg. FAB-MS calc. for $C_{32}H_{43}N_5O_5$: 577; Found 578 (M+H).

Step B:

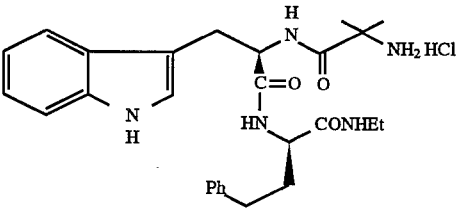

Prepared by the procedure described in Example 1, Step B from the intermediate from previous step (125 mg) and HCl gas in ethyl acetate (3 mL) at 0° C. Reaction time: 15 minutes. Product: 90.9 mg (82%).

FAB-MS calc. for $C_{27}H_{35}N_5O_3$: 477; Found: 478 (M+H).
$^1$H NMR (400 MHz, CD3OD): δ(ppM) 8.19 (d, J=7.5 Hz, 1H), 7.66–7.00 (m, 10H), 4.85–4.79 (m, 1H), 4.29–4.26 (m, 1H), 3.57 (dd, J=6, 14 Hz, 1H), 3.16 (dd, J=9, 14 Hz, 1H), 3.15–3.08 (m, 2H), 2.68–2.55 (2 m, 2H), 2.10–1.98 (m, 1H), 1.95–1.86 (m, 1H), 1.55 (s, 3H), 1.34 (s, 3H), 1.05 (t, J=7.2 Hz).

EXAMPLE 33

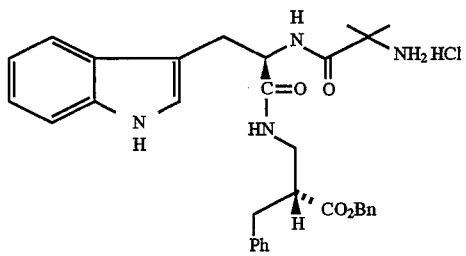

Prepared from the intermediate obtained from Example 28, Step E (10 mg) and HCl gas in ethyl acetate at 0° C. by the procedure described in Example 1, Step C to give the desired compound (9 mg). $^1$H NMR (400 MHz, CD3OD): 7.61 (d, 8 Hz, 1H), 7.28 (m, 4H), 7.18 (m, 5H), 7.06 (m, 5H), 5.02 (d, 12 Hz, 1H), 4.95 (d, 12 Hz, 1H), 4.69 (m, 1H), 3.45 (m, 1H), 3.34–3.22 (m, 2H), 3.09 (dd, 14 Hz, 9 Hz, 1H), 2.89 (m, 1H), 2.74 (d, 7 Hz, 2H), 1.53 (s, 3H), 1.33 (s, 3H). FAB-MS: 541.1 (M+1).

EXAMPLE 34

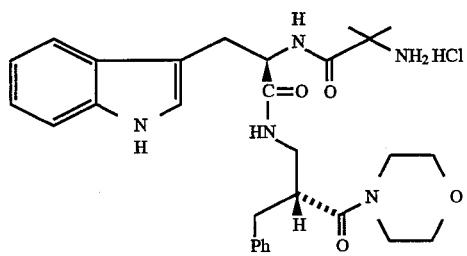

Step A:

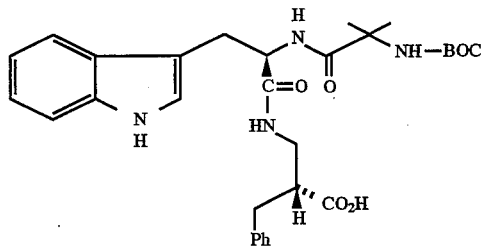

To a solution of the intermediate (101 mg) obtained from Example 28, Step E in methanol was added Pd(OH)$_2$ and hydrogenated under hydrogen (1 atmosphere) for an hour. The mixture was filtered through Celite. The filtrate was concentrated to give corresponding acid (88 mg).

Step B:

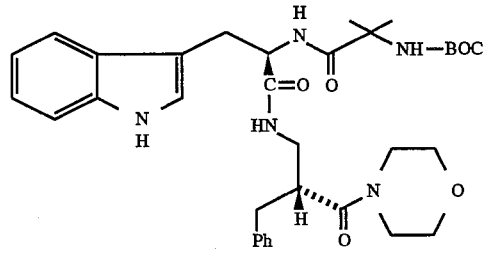

Prepared from the intermediate obtained from Step A (11 mg) and morpholine by the procedure described in Example 1, Step B (without NMM) to give the coupling product. The crude product was purified by PLC (hexanes/ethyl acetate= 1/3) to give the desired compound (11 mg).

Step C:

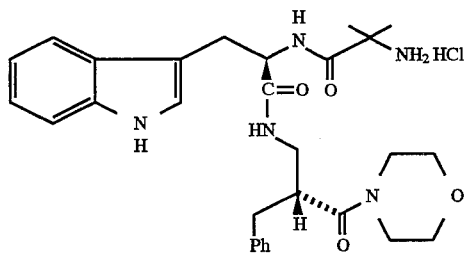

Prepared from the intermediate obtained from Step B (11 mg) and HCl gas in ethyl acetate at 0° C. by the procedure described in Example 1, Step C to give the desired compound (8.8 mg).

$^1$H NMR (400 MHz, CD3OD): 7.62 (d, 8 Hz, 1H), 7.33–6.99 (m, 9H), 4.67 (t, 7 Hz, 1H), 3.66–3.49 (m, 2H), 3.27–3.09 (m, 8H), 2.97 (m, 1H), 2.67 (m, 4H), 1.55 (s, 3H), 1.35 (s, 3H). FAB-MS: 520.1 (M+1).

EXAMPLE 35

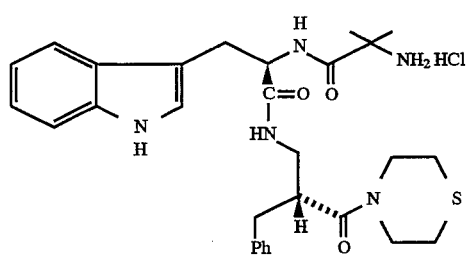

Prepared from the intermediate obtained from Example 34, Step A and thiomorpholine by the procedure described in Example 34, Step B and C to give the desired product.

$^1$H NMR (400 MHz, CD3OD): 7.63 (dd, 8 Hz, 1 Hz, 1H), 7.32 (d, 8 Hz, 1H), 7.31–6.99 (m, 8H), 4.67 (dd, 9 Hz, 8 Hz, 1H), 4.09 (m, 1H), 3.50 (m, 1H), 3.35–3.09 (m, 7H), 2.67 (m, 2H), 2.38 (m, 1H), 2.30 (m, 1H), 2.16 (m, 1H), 1.57 (m, 1H), 1.55 (s, 3H), 1.35 (s, 3H). FAB-MS: 536.2 (M+1).

EXAMPLE 36

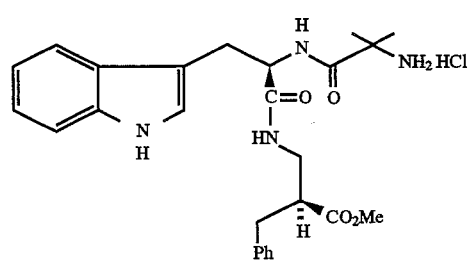

EXAMPLE 37

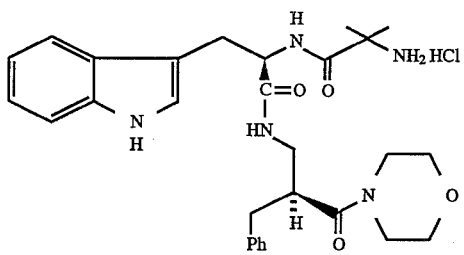

Prepared from the intermediate obtained from Example 36, Step B (21 mg) and morpholine by the procedure described in Example 1, Step B (without NMM) to give the coupling product. The crude product was purified by PLC (hexanes/ethyl acetate=1/2) and to the resulting product in methanol there was bubbled HCl gas at 0° C. for 15 seconds. The reaction was stirred for 15 minutes, when TLC analysis indicated that the reaction was complete. The solution was then concentrated to give the desired product (17 mg).

$^1$H NMR (400 MHz, CD3OD): 7.62 (dd, 8 Hz, 1 Hz, 1H), 7.31–7.19 (m, 4H), 7.14–7.07 (m, 4H), 7.02 (td, 7 Hz, 1 Hz, 1H), 4.67 (dd, 9 Hz, 7 Hz, 1H), 3.62 (m, 1H), 3.49 (m, 1H), 3.40–3.07 (m, 7H), 3.00 (m, 1H), 2.85 (m, 1H), 2.71 (m, 3H), 2.55 (m 1H), 1.56 (s, 3H), 1.36 (s, 3H). FAB-MS: 520.2 (M+1).

EXAMPLE 38

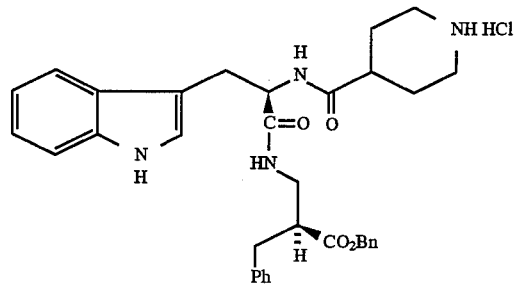

Step A:

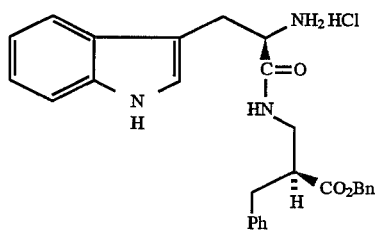

The coupling reaction was prepared from N-t-BOC-D-tryptophan (86 mg) and the intermediate obtained from Example 36, Step A (70 mg) by the procedure described in Example 1, Step B (without NMM). The coupling product was purified by chromatatron (hexanes/ethyl acetate=2/1) and then the Boc group was removed by the procedure described in Example 1, Step C to give the desired compound (70 mg).

Step A:

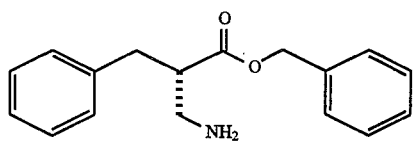

Prepared from (4R)-benzyl oxazolidinone (1.77 g) and hydrocinnamoyl chloride (1.5 ml) by the procedure described in Example 28, Step A, B, C and D to give the azido product. To this azido intermediate in methanol was added Raney nickel and hydrogenated under 1 atmosphere of hydrogen for 2 hours. The mixture was filtered through Celite and the filtrate was concentrated to give the title compound (160 mg).

Step B:

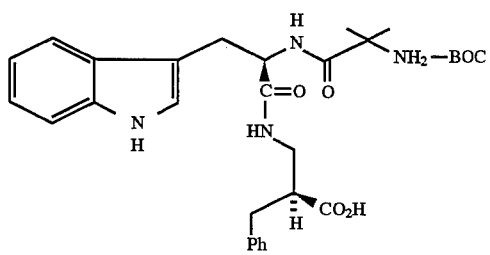

Prepared from the intermediate obtained from Step A (27 mg) and Intermediate 1 by the procedure described in Example 1, Step B (without NMM) to give coupling product (38 mg). To this coupling intermediate in methanol was added Pd(OH)2 and hydrogenated under 1 atmosphere of hydrogen for 1 hour. The mixture was filtered through Celite.

Step C:

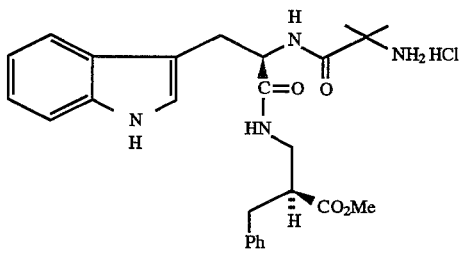

Prepared from the intermediate obtained from Step B (10 mg) and HCl gas in methanol at 0° C. by the procedure described in Example 1, Step C to give the desired compound (8 mg).

$^1$H NMR (400 MHz, CD3OD): 7.62 (dd, 8 Hz, 1 Hz, 1H), 7.30 (d, 8 Hz, 1H), 7.28–7.06 (m, 7H), 7.00 (t, 7 Hz, 1H), 4.69 (m, 1H), 3.54 (s, 3H), 3.39 (m, 1H), 3.26 (m, 2H), 3.10 (dd, 14 Hz, 9 Hz, 1H), 2.81–2.72 (m, 3H), 1.54 (s, 3H), 1.34 (s, 3H). FAB-MS: 465.1 (M+1).

Step B:

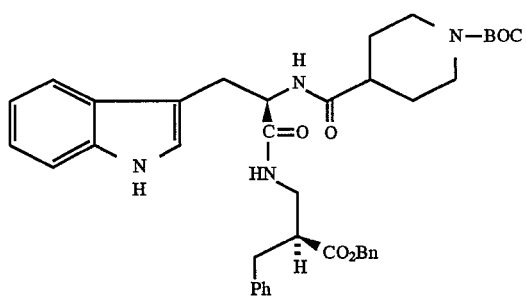

Prepared from the intermediate obtained from Step A (70 mg) and N-BOC-isonipecotic acid (44 mg) by the procedure described in Example 1, Step B using triethylamine instead of NMM to give the coupling product (86 mg).

Step C:

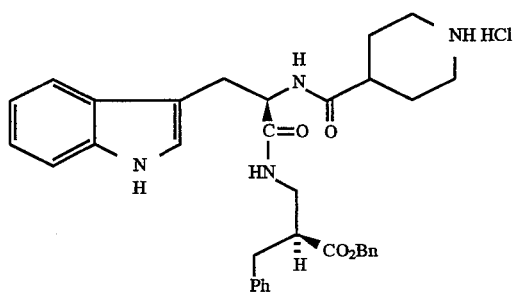

Prepared from the intermediate obtained from Step B (13 mg) by the procedure described in Example 1, Step C to give the desired compound (11 mg).

$^1$H NMR (400 MHz, CD3OD): 7.58 (dd, 8 Hz, 1 Hz, 1H), 7.30–6.98 (m, 14H), 5.00 (d, 12 Hz, 1H), 4.93 (d, 12 Hz, 1H), 4.63 (dd, 8 Hz, 7 Hz, 1H), 3.35 (m, 2H), 3.21 (m, 2H), 3.05–2.68 (m, 7H), 2.50 (m, 1H), 1.92 (m, 1H), 1.84–1.55 (m, 3H). FAB-MS: 567.3 (M+1).

EXAMPLE 39

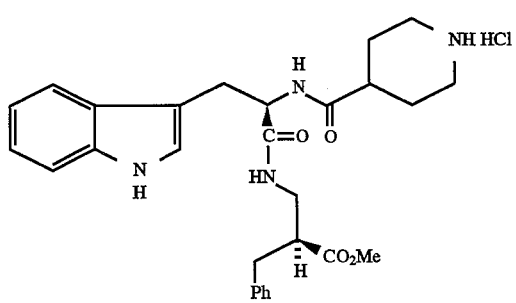

Step A:

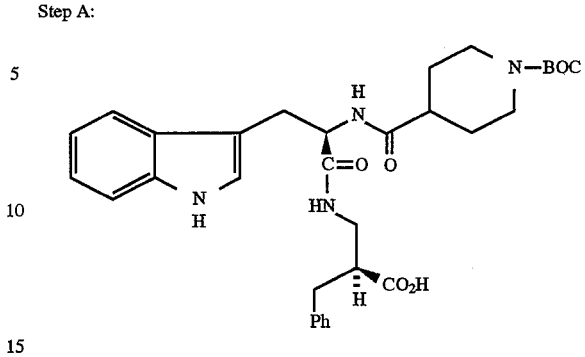

Prepared from the intermediate obtained from Example 38, Step B (71 mg) by the procedure described in Example 34, Step A to give the desired product (60 mg).

Step B:

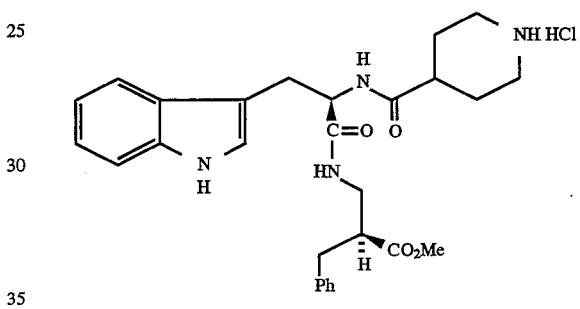

Prepared from the intermediate obtained from Step A (4 mg) and HCl gas in methanol at 0° C. by the procedure described in Example 1, Step C to give the desired compound (2.7 mg).

$^1$H NMR (400 MHz, CD3OD): 7.59 (d, 8 Hz, 1H), 7.30 (d, 8 Hz, 1H), 7.26–7.06 (m, 7H), 7.02 (t, 7 Hz, 1H), 4.63 (dd, 8 Hz, 1 Hz, 1H), 3.52 (s, 3H), 3.37 (m, 2H), 3.24 (m, 2H), 3.08–2.68 (m, 7H), 2.52 (m, 1H), 1.94 (m, 1H), 1.82–1.60 (m, 3H). FAB-MS: 491.2 (M+1).

EXAMPLE 40

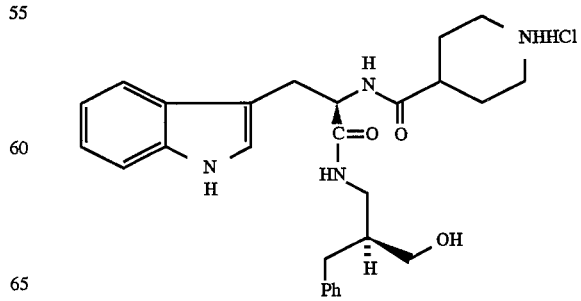

Step A:

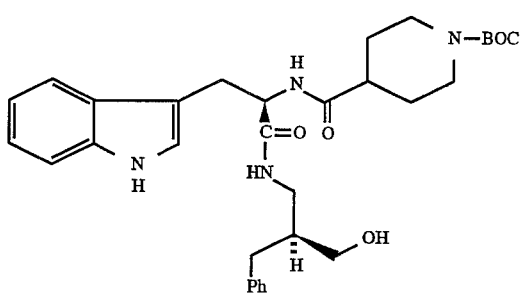

To a solution of the intermediate (12 mg) obtained from Example 39, Step A in THF (1 ml) was added borane-THF complex (0.05 ml, 1.0M solution in THF) at room temperature. After stirring for 12 hours, the reaction was quenched with water and then extracted with ethyl acetate. The organic layer was washed with 1N NaOH, brine, and dried over sodium sulfate. Concentration and purification (PLC, hexanes/ethyl acetate=1/2) gave the desired product (7 mg).

Step B:

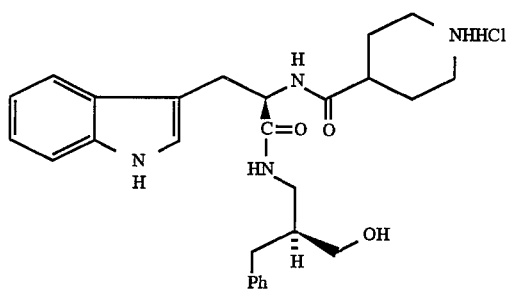

Prepared from the intermediate obtained from Step A (7 mg) and HCl gas in methanol at 0° C. by the procedure described in Example 1, Step C to give the desired compound (5 mg).

$^1$H NMR (400 MHz, CD3OD): 7.60 (d, 8 Hz, 1H), 7.29 (d, 8 Hz, 1H), 7.25–6.99 (m, 8H), 4.64 (t, 8 Hz, 1H), 3.37 (m, 1H), 3.27–2.88 (m, 9H), 2.55 (m, 1H), 2.40 (m, 2H), 1.96 (m, 1H), 1.84–1.64 (m, 4H). FAB-MS: 463.3 (M+1).

EXAMPLE 41

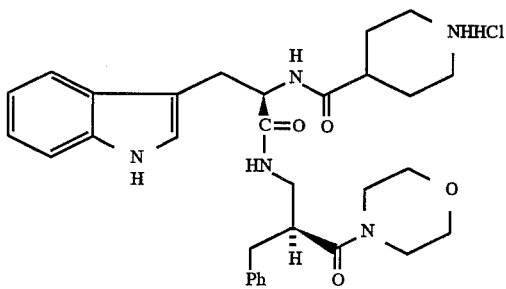

Prepared from the intermediate obtained from Example 39, Step A (12 mg) and morpholine by the procedure described in Example 1, Step B (without NMM) to give the coupling product. The crude product was purified by PLC (hexanes/ethyl acetate=1/4) to give the coupling product.

To this coupling intermediate was bubbled though HCl gas in methanol at 0° C. for 15 seconds. The reaction was stirred for 15 minutes, when TLC analysis indicated that the reaction was complete. The solution was then concentrated to give the desired product (7 mg).

$^1$H NMR (400 MHz, CD3OD): 7.60 (dd, 8 Hz, 1 Hz, 1H), 7.31–7.18 (m, 4H), 7.143–7.7 (m, 4H), 7.02 (td, 7 Hz, 1 Hz, 1H), 4.61 (t, 7 Hz, 1H), 3.60 (m, 1H), 3.49 (m, 1H), 3.40 (m, 2H), 3.28–2.85 (m, 12H), 2.69 (m, 2H), 2.54 (m, 2H), 1.95 (m, 1H), 1.83 (m, 1H), 1.74 (m, 1H), 1.64 (m, 1H). FAB-MS: 546.2 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

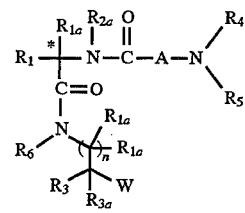

wherein:

$R_1$ is selected from the group consisting of: indolyl, indolyl($C_1$–$C_6$ alkyl)-, and indolyl($C_0$–$C_5$ alkyl)-K-($C_1$–$C_5$ alkyl)-, where K is —O—, —S(O)$_m$—, —N(R$_2$)C(O)—, —C(O)N(R$_2$)—, —OC(O)—, —C(O)O—, —CR$_2$=CR$_2$—, or —C≡C—, and where R$_2$ and alkyl may be further substituted by 1 to 9 halogen, —S(O)$_m$R$_{2a}$, 1 to 3 of —OR$_{2a}$ or —C(O)OR$_{2a}$, and indolyl may be further substituted by 1 to 3 of $C_1$–$C_6$ alkyl, 1 to 3 of halogen, 1 to 2 of —OR$_2$, methylenedioxy, —N(R$_2$)(R$_2$), —S(O)$_m$R$_2$, 1 to 2 of —CF$_3$, —OCF$_3$, —C(O)H, nitro, —N(R$_2$)C(O)(R$_2$), —C(O)OR$_2$, —C(O)N(R$_2$)(R$_2$), —1H-tetrazol-5-yl, —SO$_2$N(R$_2$)(R$_2$), —N(R$_2$)SO$_2$ phenyl, or —N(R$_2$)SO$_2$R$_2$;

$R_{1a}$ is independently hydrogen, or $C_1$–$C_6$ alkyl;

$R_2$ is selected from the group consisting of: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur, SO$_2$ or NR$_{2a}$;

$R_{2a}$ is hydrogen, or $C_1$–$C_6$ alkyl optionally substituted by hydroxyl;

$R_3$ is independently selected from the group consisting of: hydrogen, —$C_1$–$C_{10}$ alkyl, —(CH$_2$)$_r$phenyl, —(CH$_2$)

,naphthyl, —(CH₂),indanyl, —(CH₂),dibenzocycloheptanyl, —(CH₂),C(O)OR₈, —(CH₂),C(O)N(R₂)(R₈), (C₁–C₆ alkyl)-K-(C₁–C₄ alkyl)-, aryl (C₀–C₅ alkyl)-K-(C₁–C₄ alkyl)-, —(CH₂),—C₃–C₇ cycloalkyl, and —(CH₂),heteroaryl, where K is O or S(O)ₘ, and where heteroaryl is selected from: pyridyl, indolyl, imidazolyl, quinolinyl, benzothiopheneyl, benzofuranyl, dihydroindolyl, thiazolyl, benzimidazolyl, and azaindolyl, and where the phenyl, naphthyl, indanyl, dibenzocycloheptanyl, and heteroaryl may be substituted by: C₁–C₆ alkyl, 1 to 2 of halogen, 1 to 2 of —OR₉, —NHSO₂CF₃, —C(O)H, —(CH₂),N(R₂)(R₉), —(CH₂),C(O)OR₉, —(CH₂),N(R₂)C(O)R₉, —(CH₂),C(O)N(R₂)(R₉), —(CH₂),N(R₆)C(O)N(R₂)(R₉), or —(CH₂),(R₉);

R$_{3a}$ is hydrogen or C₁–C₆ alkyl;

R₄ and R₅ are independently selected from: hydrogen, C₁–C₆ alkyl, and substituted C₁–C₆ alkyl where the substituents are selected from: 1 to 5 halogen, 1 to 3 of hydroxy, 1 to 3 of C₁–C₁₀ alkanoyloxy, 1 to 3 of C₁–C₆ alkoxy, phenyl, phenoxy, 2-furyl, C₁–C₆ alkoxycarbonyl, and S(O)ₘ(C₁–C₆ alkyl); or R₄ and R₅ can be taken together to form —(CH₂)$_d$L$_a$(CH₂)$_e$— where L$_a$ is —C(R₂)₂—, —O—, —S(O)ₘ— or —N(R$_{2a}$)—, and d and e are independently 1 to 3;

R₆ is hydrogen or C₁–C₄ alkyl;

R₇ and R$_{7a}$ are independently hydrogen, C₁–C₆ alkyl, trifluoromethyl, phenyl, substituted C₁–C₆ alkyl where the substituents are selected from: imidazolyl, phenyl, indolyl, p-hydroxyphenyl, naphthyl, halophenyl, quinolinyl, dihalophenyl, C₁–C₂ alkoxyphenyl, di (C₁–C₂ alkoxy)phenyl, C₁–C₂ alkylphenyl, di (C₁–C₂ alkyl)phenyl, —OR₂, —S(O)ₘR₂, —C(O)O(C₁–C₆ alkyl), C₃–C₇ cycloalkyl, —N(R₂)(R₂), and —C(O)N(R₂)(R₂); or R₇ and R$_{7a}$ can independently be joined to one or both of R₄ and R₅ groups to form an alkylene bridge between the terminal nitrogen and the alkyl portion of the R₇ or R$_{7a}$ groups, wherein the bridge contains 1 to 5 carbons atoms; or R₇ and R$_{7a}$ can be joined to one another to form a C₃–C₇ cycloalkyl;

R₈ is selected from the group consisting of: hydrogen, C₁–C₆ alkyl, aryl, and aryl-C₁–C₂ alkyl, where the alkyl groups may be substituted by a substituent selected from the group consisting of: —OR₂, —C(O)OR₂, —C(O)O-benzyl, —CON(R₂)(R₂), —N(R₂)C(O)N(R₂)(R₂), and 1H-tetrazol-5-yl, and where aryl is selected from the group consisting of: phenyl, naphthyl, indolyl, quinolinyl, benzothiopheneyl, benzofuranyl, azaindolyl, benzimidazolyl, pyridyl, and thiazolyl, and where the aryl may be substituted by: 1 to 2 of —OR₂, 1 to 2 of halogen, 1 to 2 of C₁–C₃ alkyl, —C(O)OR₂, —C(O)N(R₂)(R₂), or —1H-tetrazol-5-yl;

R₉ is hydrogen, C₁–C₆ alkyl, or (CH₂)ᵥaryl, wherein the alkyl and (CH₂)ᵥ groups may be optionally substituted by 1 to 2 of —O(R₂), —S(O)ₘR₂, —N(R₂)(R₂), 1H-tetrazol-5-yl, —C(O)OR₂, —C(O)N(R₂)(R₂), —SO₂N(R₂)(R₂), or —N(R₂)C(O)N(R₂)(R₂), and where aryl is selected from: phenyl, pyridyl, 1H-tetrazol-5-yl, triazolyl, imidazolyl, thiazolyl, oxadiazolyl, pyrazolyl, thiadiazolyl, imidazolone-1-yl, and benzimidazol-2-yl, triazolinone-yl, and where the aryl is optionally substituted with C₁–C₆ alkyl, C₃–C₆ cycloalkyl, amino, hydroxyl, or —C(O)O(R₂);

A is:

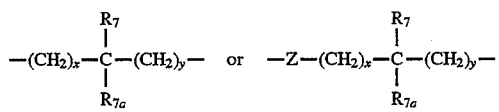

where x and y are independently 0, 1, 2 or 3;

Z is —NR₂ or -O-;

W is selected from the group consisting of: hydrogen, —C(O)OR₈, —C(O)N(R₂)(R₂), —C(O)NH—SO₂(R₂), —C(O)N(R₂)(R₈), —CH₂N(R₂)C(O)N(R₂)(R₈), —CH₂N(R₂)C(O)R₈, —CH₂N(R₂)C(O)(R₈), —(CH₂),OR₂, —CH(OH)R₂, —CH₂SO₂R₂, —CH₂SO₂N(R₂)(R₂), 1H-tetrazol-5-yl, 5-amino-1,2,4-oxadiazol-3-yl, 5-methyl-1,2,4-oxadiazol-3-yl, 3-amino-1,2,4-oxadiazol-5-yl, and 3-methyl-1,2,4-oxadiazol-5-yl;

m is 0, 1, or 2;

n is 0 or 1;

r is 0, 1, 2, or 3;

v is 0, 1, or 2;

and pharmaceutically acceptable salts and individual diastereomers thereof.

2. The compound of claim 1 of the Formula Ia:

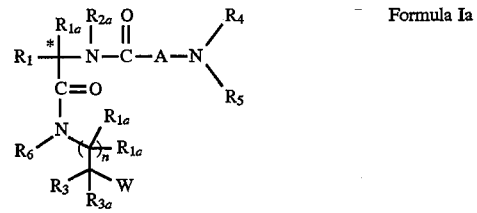

Formula Ia wherein:

R₁ is selected from the group consisting of: indolyl, indolyl(C₁–C₄ alkyl)-, and indolyl(C₀–C₂ alkyl)-K-(C₁–C₂ alkyl)-, where K is —O—, —S(O)ₘ—, —OC(O)—, or —C(O)O—, where the alkyl groups may be further substituted by 1 to 7 halogen, —S(O)ₘR$_{2a}$, 1 to 3 of —OR$_{2a}$ or —C(O)OR$_{2a}$, and where the indolyl may be further substituted by 1 to 2 of C₁–C₄ alkyl, 1 to 2 of halogen, —C(O)H, 1 to 2 of —OR₂, —S(O)ₘR₂, or —C(O)OR₂;

R$_{1a}$ is independently hydrogen or C₁–C₃ alkyl;

R₂ is selected from the group consisting of: hydrogen, C₁–C₆ alkyl, and C₃–C₇ cycloalkyl, and where two C₁–C₆ alkyl groups are present on one atom they may be optionally joined to form a C₄–C₇ cyclic ring optionally including oxygen, sulfur or NR$_{2a}$;

R$_{2a}$ is hydrogen or C₁–C₄ alkyl;

R₃ is independently selected from the group consisting of: hydrogen, —C₁–C₈ alkyl, —(CH₂),phenyl, —(CH₂),naphthyl, —(CH₂),indanyl, —(CH₂),dibenzocycloheptanyl, and —(CH₂),heteroaryl, where heteroaryl is selected from: pyridyl, indolyl, quinolinyl, benzothiopheneyl, benzofuranyl, thiazolyl, dihydroindolyl, benzimidazolyl, and azaindolyl, and where the phenyl, naphthyl, indanyl, dibenzocycloheptanyl, and heteroaryl may be substituted by: C₁–C₄ alkyl, 1 to 2 of halogen, 1 to 2 of —OR₂, —NHSO₂CF₃, —(CH₂),C(O)OR₂, —(CH₂),C(O)N(R₂)(R₂), —(CH₂),N(R₆)C(O)N(R₂)(R₂), or —(CH₂),(R₉);

R$_{3a}$ is hydrogen or C₁–C₆ alkyl;

$R_4$ and $R_5$ are independently selected from: hydrogen, $C_1$–$C_6$ alkyl, and substituted $C_1$–$C_6$ alkyl where the substituents are selected from: 1 to 5 of halogen, 1 to 3 of hydroxyl, $S(O)m(C_1$–$C_6$ alkyl), and phenyl;

$R_6$ is hydrogen or $C_1$–$C_4$ alkyl;

$R_7$ and $R_{7a}$ are independently hydrogen, $C_1$–$C_6$ alkyl, trifluoromethyl, phenyl, substituted $C_1$–$C_6$ alkyl where the substituents are selected from: imidazolyl, phenyl, indolyl, p-hydroxyphenyl, naphthyl, halophenyl, quinolinyl, dihalophenyl, $C_1$–$C_2$ alkoxyphenyl, di($C_1$–$C_2$ alkoxy)phenyl, —$OR_2$, —$S(O)_mR_2$, —$C(O)O$ ($C_1$–$C_6$ alkyl), $C_3$–$C_7$ cycloalkyl, —$N(R_2)(R_2)$, and —$C(O)N(R_2)(R_2)$; or $R_7$ and $R_{7a}$ can independently be joined to one or both of $R_4$ and $R_5$ groups to form an alkylene bridge between the terminal nitrogen and the alkyl portion of the $R_7$ or $R_{7a}$ groups, wherein the bridge contains 1 to 5 carbons atoms; or $R_7$ and $R_{7a}$ can be joined to one another to form a $C_3$–$C_7$ cycloalkyl;

$R_8$ is selected from the group consisting of: hydrogen, $C_1$–$C_4$ alkyl, aryl, and aryl-$C_1$–$C_2$ alkyl, where the alkyl groups may be substituted by a substituent selected from the group consisting of: —$OR_2$, —$C(O)OR_2$, —$C(O)O$-benzyl, —$CON(R_2)(R_2)$, —$N(R_2)C(O)N(R_2)(R_2)$, and 1H-tetrazol-5-yl, and where aryl is selected from the group consisting of: phenyl, naphthyl, indolyl, azaindolyl, pyridyl, and thiazolyl, and where the aryl may be substituted by: 1 to 2 of —$OR_2$, 1 to 2 of halogen, or 1 to 2 of $C_1$–$C_3$ alkyl;

$R_9$ is $(CH_2)_v$aryl, where aryl is selected from: phenyl, pyridyl, 1H-tetrazol-5-yl, or oxadiazolyl, and where the aryl is optionally substituted with $C_1$–$C_6$ alkyl, amino, hydroxyl, or —$C(O)O(R_2)$;

A is:

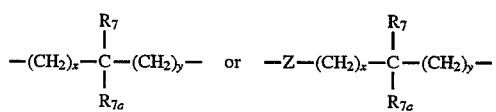

where x and y are independently 0, 1, 2 or 3;

Z is —$NR_2$— or —O—;

W is selected from the group consisting of: hydrogen, —$C(O)OR_8$, —$CH_2OR_2$, —$C(O)N(R_2)(R_2)$, —$C(O)N(R_2)(R_8)$, 1H-tetrazol-5-yl, —$CH_2N(R_2)C(O)R_8$, $CH_2N(R_2)C(O)N(R_2)(R_8)$, —$(CH_2)_rOR_2$, —CH(OH)$R_2$, 3-amino-1,2,4-oxadiazol-5-yl, 3-methyl-1,2,4-oxadiazol-5-yl,5-amino-1,2,4-oxadiazol-3-yl, and 5-methyl-1,2,4-oxadiazol-3-yl;

m is 0, 1, or 2;

n is 0 or 1;

r is 0, 1, 2, or 3;

v is 0, 1, or 2;

and pharmaceutically acceptable salts and individual diastereomers thereof.

3. The compound of claim 1 of the formula:

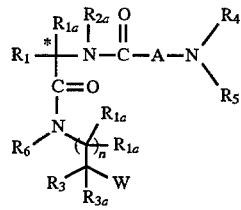

Formula Ib wherein:

$R_1$ is selected from the group consisting of: indolyl($C_1$–$C_3$ alkyl)-, and indolyl ($C_0$–$C_1$ alkyl)-K-($C_1$–$C_2$ alkyl)-, where K is —O— or —$S(O)_m$— and where the indolyl may be further substituted by 1 to 2 of $C_1$–$C_4$ alkyl, 1 to 2 of halogen, 1 to 2 of —$OR_2$, —$S(O)_mR_2$, or —$C(O)OR_2$;

$R_{1a}$ is independently hydrogen or $C_1$–$C_2$ alkyl;

$R_2$ is selected from the group consisting of: hydrogen, $C_1$–$C_6$ alkyl, and $C_3$–$C_7$ cycloalkyl, and where two $C_1$–$C_6$ alkyl groups are present on one atom they may be optionally joined to form a $C_5$–$C_7$ cyclic ring optionally including oxygen, sulfur or $NR_{2a}$;

$R_{2a}$ is hydrogen or $C_1$–$C_3$ alkyl;

$R_3$ is independently selected from the group consisting of: hydrogen, —$C_1$–$C_6$ alkyl, —$(CH_2)_t$phenyl, —$(CH_2)_t$naphthyl, and —$(CH_2)_t$heteroaryl, where heteroaryl is selected from: pyridyl, thiazolyl, indolyl, quinolinyl, benzofuranyl, and azaindolyl, and where the phenyl, naphthyl and heteroaryl may be substituted by: $C_1$–$C_3$ alkyl, 1 to 2 of halogen, 1 to 2 of —$OR_2$, —$(CH_2)_tC(O)OR_2$, —$(CH_2)_tC(O)N(R_2)(R_2)$, —$(CH_2)_tN(R_6)C(O)N(R_2)(R_2)$, or —$(CH_2)_t(R_9)$;

$R_{3a}$ is hydrogen or $C_1$ alkyl;

$R_4$ and $R_5$ are independently hydrogen, $C_1$–$C_4$ alkyl, or substituted $C_1$–$C_3$ alkyl where the substituents are selected from: 1 to 5 of halogen, 1 to 3 of hydroxyl, $S(O)m$ ($C_1$–$C_6$ alkyl), and phenyl;

$R_6$ is hydrogen or $C_1$–$C_3$ alkyl;

$R_7$ and $R_{7a}$ are independently hydrogen, $C_1$–$C_3$ alkyl, phenyl, substituted $C_1$–$C_6$ alkyl where the substituents are selected from: imidazolyl, phenyl, indolyl, p-hydroxyphenyl, naphthyl, halophenyl, dihalophenyl, —$OR_2$, —$N(R_2)(R_2)$, and —$S(O)_mR_2$, or $R_7$ and $R_{7a}$ can independently be joined to one of $R_4$ and $R_5$ groups to form an alkylene bridge between the terminal nitrogen and the alkyl portion of the $R_7$ or $R_{7a}$ groups to form a 5 or 6 membered ring; or $R_7$ and $R_{7a}$ can be joined to one another to form a $C_3$ cycloalkyl;

$R_8$ is selected from the group consisting of: hydrogen, $C_1$–$C_4$ alkyl, and aryl-$C_1$–$C_2$ alkyl, where the alkyl groups may be substituted by a substituent selected from the group consisting of: —$OR_2$, —$C(O)OR_2$, —$C(O)O$-benzyl, —$CON(R_2)(R_2)$, —$N(R_2)C(O)N(R_2)(R_2)$, and 1H-tetrazol-5-yl, and where aryl is selected from the group consisting of: phenyl, naphthyl, indolyl, 7-azaindolyl, pyridyl, and thiazolyl, and where the aryl may be substituted by: 1 to 2 of —$OR_2$, 1 to 2 of halogen, or 1 to 2 of $C_1$–$C_3$ alkyl;

$R_9$ is $(CH_2)_v$aryl, where aryl is selected from: 1H-tetrazol-5-yl, and oxadiazolyl, and where the aryl is optionally substituted with $C_1$–$C_6$ alkyl, amino, or hydroxyl;

A is:

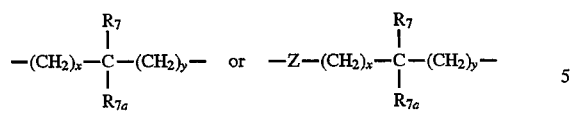

where x and y are independently 0, 1, or 2;

W is selected from the group consisting of: hydrogen, —C(O)OR$_8$, CH$_2$OR$_2$, —C(O)N(R$_2$)(R$_2$), —C(O)N(R$_2$)(R$_8$), 1H-tetrazol-5-yl, CH$_2$N(R$_2$)C(O)R$_8$, CH$_2$N(R$_2$)C(O)N(R$_2$)(R$_8$), 3-amino-1,2,4-oxadiazol-5-yl, and 3-methyl-1,2,4-oxadiazol-5-yl;

Z is —NR$_2$— or —O—;

W is selected from the group consisting of: hydrogen, —C(O)OR$_8$, —C$_2$OR$_2$—C(O)N(R$_2$)(R$_2$), —C(O)N(R$_2$)(R$_8$), 1H-tetrazol-5-yl, —CH$_2$N(R$_2$)C(O)R$_8$, CH$_2$N(R$_2$)C(O)N(R$_2$)(R$_8$), —(CH$_2$)$_r$OR$_2$, —CH(OH)R$_2$, 3-amino-1,2,4-oxadiazol-5-yl, and 3-methyl-1,2,4-oxadiazol-5-yl;

m is 0, 1, or 2;

n is 0 or 1;

r is 0, 1, 2, or 3;

v is 0, 1, or 2;

and pharmaceutically acceptable salts and individual diastereomers thereof.

4. The stereospecifically defined compound of claim 1 of the formula:

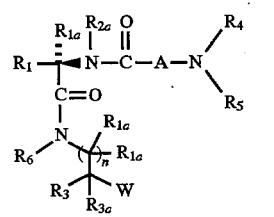

where R$_1$, R$_{1a}$, R$_{2a}$, R$_3$, R$_{3a}$, R$_4$, R$_5$, R$_6$, A, W and n are as defined above.

5. A compound which is selected from the group consisting of:

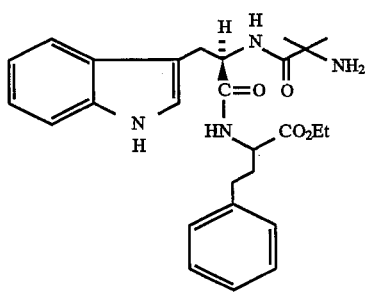

-continued

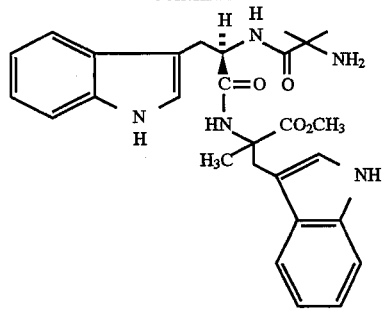

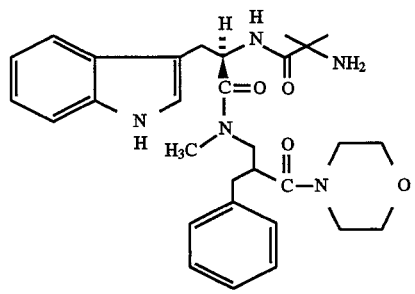

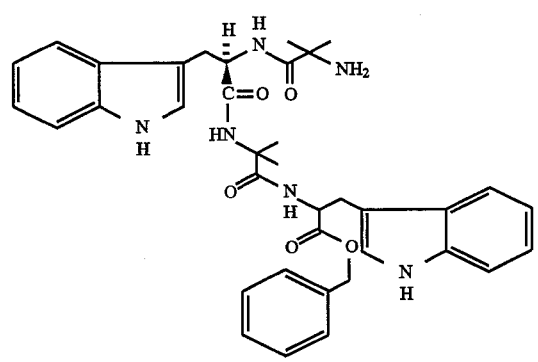

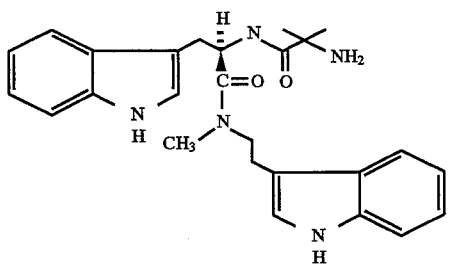

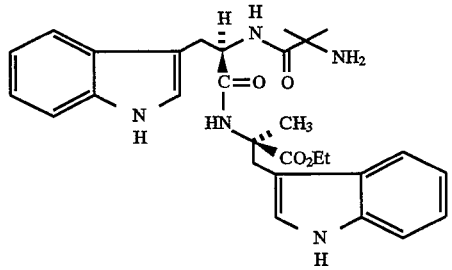

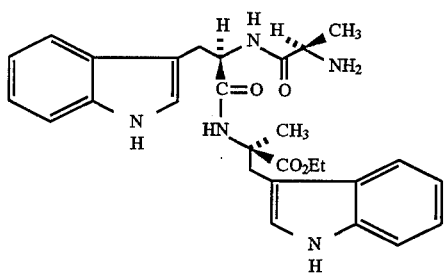
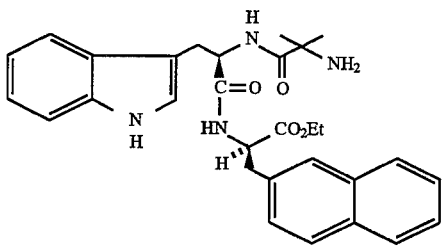
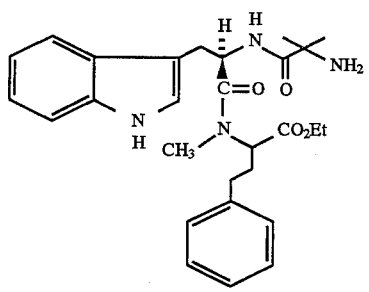
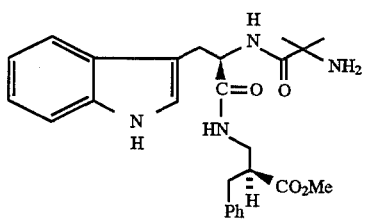
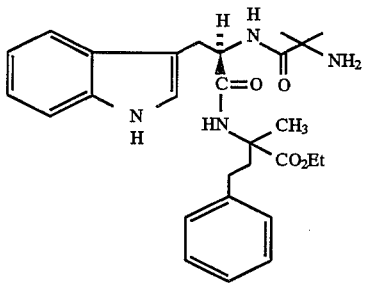
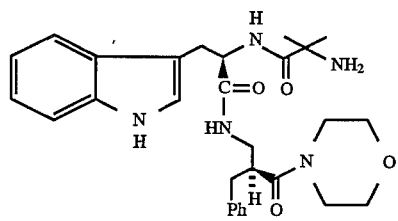
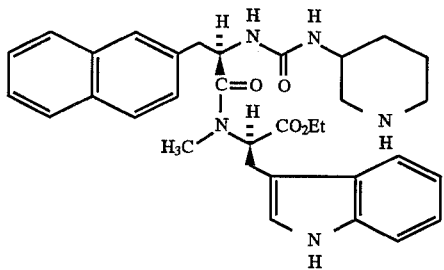
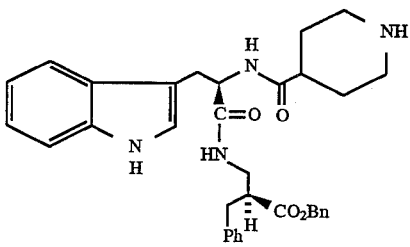
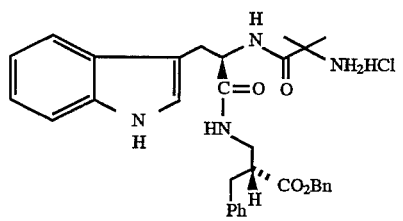
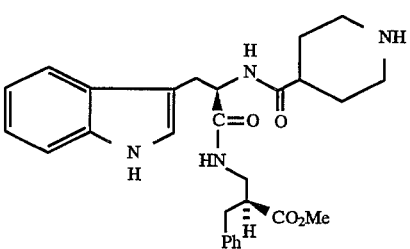
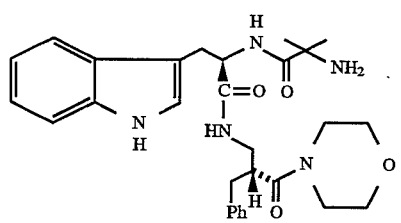
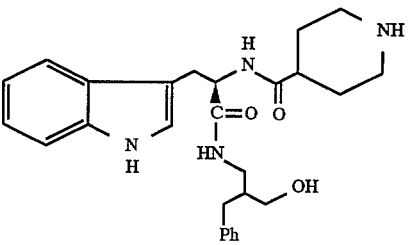

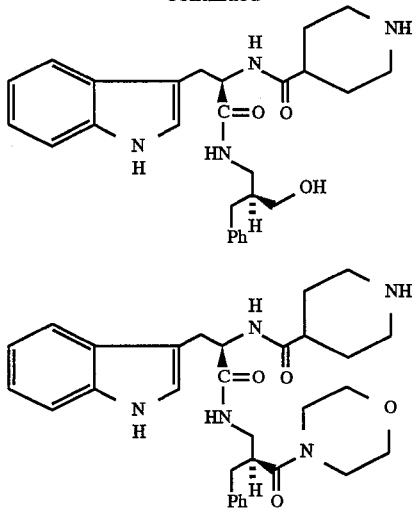

and the pharmaceutically acceptable salts and individual diasteromers thereof, where not otherwise specified.

6. A pharmaceutical composition which comprises an inert carrier and an effective amount of the compound of claim 1.

7. A method for increasing levels of endogenous growth hormone in a human or an animal which comprises administering to such human or animal an effective amount of the compound of claim 1.

8. A method for increasing feed efficiency, promoting growth, increasing milk production and improving the carcass quality of livestock which comprises administering to such livestock an effective amount of the compound of claim 1.

9. A method for the treatment of a disease or a condition which is benefited by the anabolic effects of enhanced growth hormone levels that comprises administering to a patient in need thereof an effective amount the compound of claim 1.

* * * * *